US012240879B2

(12) United States Patent
Zhong et al.

(10) Patent No.: US 12,240,879 B2
(45) Date of Patent: *Mar. 4, 2025

(54) INTERLEUKIN-22 FUSION PROTEINS, AND THEIR PHARMACEUTICAL COMPOSITIONS

(71) Applicant: Anwita Biosciences, Inc., San Carlos, CA (US)

(72) Inventors: Ziyang Zhong, Belmont, CA (US); Fan Ye, Mountain View, CA (US); Jianing Huang, San Mateo, CA (US); Matthew Siegel, Menlo Park, CA (US); Ji Wang, Castro Valley, CA (US)

(73) Assignee: Anwita Biosciences, Inc., San Carlos, CA (US)

( * ) Notice: Subject to any disclaimer, the term of this patent is extended or adjusted under 35 U.S.C. 154(b) by 607 days.

This patent is subject to a terminal disclaimer.

(21) Appl. No.: 17/388,129

(22) Filed: Jul. 29, 2021

(65) Prior Publication Data

US 2022/0033454 A1 Feb. 3, 2022

Related U.S. Application Data

(60) Provisional application No. 63/059,137, filed on Jul. 30, 2020.

(51) Int. Cl.
| | |
|---|---|
| *A61K 38/20* | (2006.01) |
| *C07K 14/54* | (2006.01) |
| *C07K 14/605* | (2006.01) |
| *C07K 14/65* | (2006.01) |
| *C07K 16/18* | (2006.01) |
| *A61K 38/00* | (2006.01) |

(52) U.S. Cl.
CPC ............ *C07K 14/54* (2013.01); *C07K 14/605* (2013.01); *C07K 14/65* (2013.01); *C07K 16/18* (2013.01); *A61K 38/00* (2013.01); *C07K 2317/565* (2013.01); *C07K 2317/569* (2013.01); *C07K 2319/30* (2013.01)

(58) Field of Classification Search
CPC .............. C07K 14/54; C07K 2317/565; C07K 2317/569; C07K 2319/00; A61K 38/20
See application file for complete search history.

(56) References Cited

U.S. PATENT DOCUMENTS

| | | | | |
|---|---|---|---|---|
| 2011/0305663 | A1* | 12/2011 | Gosselin ................ | A61K 47/62 514/6.9 |
| 2015/0202267 | A1* | 7/2015 | Yan ........................... | A61P 1/16 424/85.2 |
| 2019/0169250 | A1 | 6/2019 | Bootz et al. | |
| 2021/0002343 | A1 | 1/2021 | Karow et al. | |
| 2021/0230242 | A1 | 7/2021 | Zhong et al. | |
| 2021/0340272 | A1 | 11/2021 | Zhong et al. | |
| 2022/0195021 | A1 | 6/2022 | Zhong et al. | |

FOREIGN PATENT DOCUMENTS

| | | |
|---|---|---|
| WO | 2015179918 A1 | 12/2015 |
| WO | 2018151868 A2 | 8/2018 |
| WO | 2019246003 A1 | 12/2019 |
| WO | 2019246004 A1 | 12/2019 |
| WO | 2020172528 A1 | 8/2020 |
| WO | 2021102063 A1 | 5/2021 |

OTHER PUBLICATIONS

Van Faassen et al. Serum albumin-binding VHHs with variable pH sensitivities enable tailored half-life extension of biologics. FASEB J. Jun. 2020;34(6):8155-8171. Epub Apr. 28, 2020.*
Andoh et al., "Interleukin-22, a member of the IL-10 subfamily, induces inflammatory responses in colonic subepithelial myofibroblasts," Gastroenterology 2005, 129, 969-84.
Dudakov et al., "Interleukin-22 drives endogenous thymic regeneration in mice," Science 2012, 336, 91-5.
Dudakov et al., "Interleukin-22: immunobiology and pathology," Annu. Rev. Immunol. 2015, 33, 747-85.
Hernandez et al., "A catch-22: Interleukin-22 and cancer," Eur. J. Immunol. 2017, 48, 15-31.
Jones et al., "Structure of IL-22 bound to its high-affinity IL-22R1 chain," Structure 2008, 16, 1333-44.
Keir et al., "The role of IL-22 in intestinal health and disease," J. Exp. Med. 2020, 217, e20192195.
Leonard and Wan, "IL-21 signaling in immunity," F1000Res. 2016, 5(F1000 Faculty Rev), 224.
Li et al., "Role of interleukin-22 in inflammatory bowel disease," World J. Gastroenterol. 2014, 20, 18177-88.
Liao et al., "IL-2 family cytokines: new insights into the complex roles of IL-2 as a broad regulator of T helper cell differentiation," Curr. Opin. Immunol. 2011, 23, 598-604.
Mackall et al., "Harnessing the biology of IL-7 for therapeutic application," Nat. Rev. Immunol. 2011, 11, 330-42.
Martin et al., "Interleukin-22 binding protein (IL-22BP) is constitutively expressed by a subset of conventional dendritic cells and is strongly induced by retinoic acid," Mucosal Immunol. 2014, 7, 101-13.
Mizoguchi et al., "Clinical importance of IL-22 cascade in IBD," J. Gastroenterol. 2018, 53, 465-74.
Parks et al., "Interleukin-22 Signaling in the Regulation of Intestinal Health and Disease," Front. Cell Dev. Biol. 2016, 3, 85.
Pelczar et al., "A pathogenic role for T cell-derived IL-22BP in inflammatory bowel disease," Science 2016, 354, 358-62.
Sabat et al., "Therapeutic opportunities of the IL-22-IL-22R1 system," Nat. Rev. Drug Discov. 2014, 13, 21-38.
Sonnenberg et al., "Border patrol: regulation of immunity, inflammation and tissue homeostasis at barrier surfaces by IL-22," Nat. Immunol. 2011, 12, 383-90.
Spangler et al., "Insights into cytokine-receptor interactions from cytokine engineering," Annu. Rev. Immunol. 2015, 33, 139-67.

(Continued)

*Primary Examiner* — Dong Jiang
(74) *Attorney, Agent, or Firm* — Lin Yu, Esq.; Juniv LLP

(57) ABSTRACT

Provided herein are a fusion protein comprising an interleukin-22 domain and an albumin binding domain, and a pharmaceutical composition thereof. Also provided herein are methods of their use for treating, preventing, or ameliorating one or more symptoms of an inflammatory disease.

25 Claims, 4 Drawing Sheets

Specification includes a Sequence Listing.

(56) References Cited

OTHER PUBLICATIONS

Wolk et al., "IL-22 induces lipopolysaccharide-binding protein in hepatocytes: a potential systemic role of IL-22 in Crohn's disease," J. Immunol. 2007, 178, 5973-81.
Zenewicz et al., "Innate and adaptive interleukin-22 protects mice from inflammatory bowel disease," Immunity 2008, 29, 947-57.
Zenewicz, "IL-22: There is a gap in our knowledge," ImmunoHorizons 2018, 2, 198-207.

* cited by examiner

INTERLEUKIN-22 FUSION PROTEINS, AND THEIR PHARMACEUTICAL COMPOSITIONS

CROSS REFERENCE TO RELATED APPLICATION

This application claims the benefit of U.S. Provisional Application No. 63/059,137, filed Jul. 30, 2020; the disclosure of which is incorporated herein by reference in its entirety.

FIELD

Provided herein are a fusion protein comprising an interleukin-22 domain and an albumin binding domain, and a pharmaceutical composition thereof. Also provided herein are methods of their use for treating, preventing, or ameliorating one or more symptoms of an inflammatory disease.

REFERENCE TO A SEQUENCE LISTING

The present specification is being filed with a Sequence Listing in Computer Readable Form (CRF), which is entitled 216A008US01_SEQLIST_ST25 of 150,704 bytes in size and created Jul. 29, 2021; the content of which is incorporated herein by reference in its entirety.

BACKGROUND

Interleukin-22 (IL-22) is a critical cytokine in modulating tissue responses during inflammation. Sabat et al., *Nat. Rev. Drug Discov.* 2014, 13, 21-38; Zenewicz, *ImmunoHorizons* 2018, 2, 198-207. IL-22 is upregulated in many chronic inflammatory diseases, including inflammatory bowel disease (IBD). Andoh et al., *Gastroenterology* 2005, 129, 969-84; Zenewicz, *ImmunoHorizons* 2018, 2, 198-207. IL-22 mediates protection and regeneration of epithelial tissues. Sonnenberg et al., *Nat. Immunol.* 2011, 12, 383-90; Dudakov et al., *Science* 2012, 336, 91-5. IL-22 has been documented to safeguard the colonic epithelium in various experimental models of colonic inflammation. Hernandez et al., *Eur. J. Immunol.* 2017, 48, 15-31. In a dextran sulfate sodium (DSS)-induced colitis model and a Th2-mediated chronic colitis model, IL-22 has been shown to provide protection during inflammation. Zenewicz et al., *Immunity* 2008, 29, 947-57. However, there is currently no FDA-approved drug that directly targets IL-22. Zenewicz, *ImmunoHorizons* 2018, 2, 198-207. Therefore, there is a need for an effective immunotherapy for treating an inflammatory disease.

SUMMARY OF THE DISCLOSURE

Provided herein is a fusion protein comprising an interleukin-22 domain and an albumin binding domain, wherein the interleukin-22 domain and albumin binding domain are at the amino-terminus (N-terminus) and carboxy-terminus (C-terminus) of the fusion protein, respectively; or wherein the interleukin-22 domain and albumin binding domain are at the C-terminus and N-terminus of the fusion protein, respectively.

Also provided herein is a fusion protein comprising an interleukin-22 domain, a peptide domain, and an albumin binding domain, wherein the peptide domain is an interleukin-22 domain, a glucagon-like peptide-2 (GLP-2) domain, or an insulin-like growth factor 1 (IGF-1) domain.

Additionally, provided herein is a fusion protein comprising first and second interleukin-22 domains, and an albumin binding domain.

Furthermore, provided herein is a fusion protein comprising first and second interleukin-22 domains, a GLP-2 domain or an IGF-1 domain, and an albumin binding domain.

Provided herein is a fusion protein comprising first and second interleukin-22 domains, a GLP-2 domain, and an albumin binding domain.

Provided herein is a fusion protein comprising first and second interleukin-22 domains, an IGF-1 domain, and an albumin binding domain.

Provided herein is a fusion protein comprising the amino acid sequence of Formula (I):

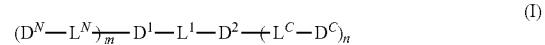

wherein:
D$^1$ is an interleukin-22 domain and D$^2$ is an albumin binding domain; or D$^1$ is an albumin binding domain and D$^2$ is an interleukin-22 domain;
D$^C$ and D$^N$ are each independently an interleukin-22 domain, a GLP-2 domain, or an IGF-1 domain;
L$^1$, L$^C$, and L$^N$ are each independently a bond or a peptide linker; and
m and n are each independently an integer of 0 or 1;
wherein D$^C$ and D$^N$ are at the C-terminus and N-terminus of the fusion protein, respectively.

Provided herein is a pharmaceutical composition comprising a fusion protein provided herein, e.g., a fusion protein comprising the amino acid sequence of Formula (I), and a pharmaceutically acceptable excipient.

Provided herein is a method of treating, preventing, or ameliorating one or more symptoms of an inflammatory disease in a subject, comprising administering to the subject in need thereof a therapeutically effective amount of a fusion protein provided herein, e.g., a fusion protein comprising the amino acid sequence of Formula (I).

(SEQ ID NO: 64) at a dose of 56 µg on the body weights of mice in a DSS-induced colitis model.

Figure 7:
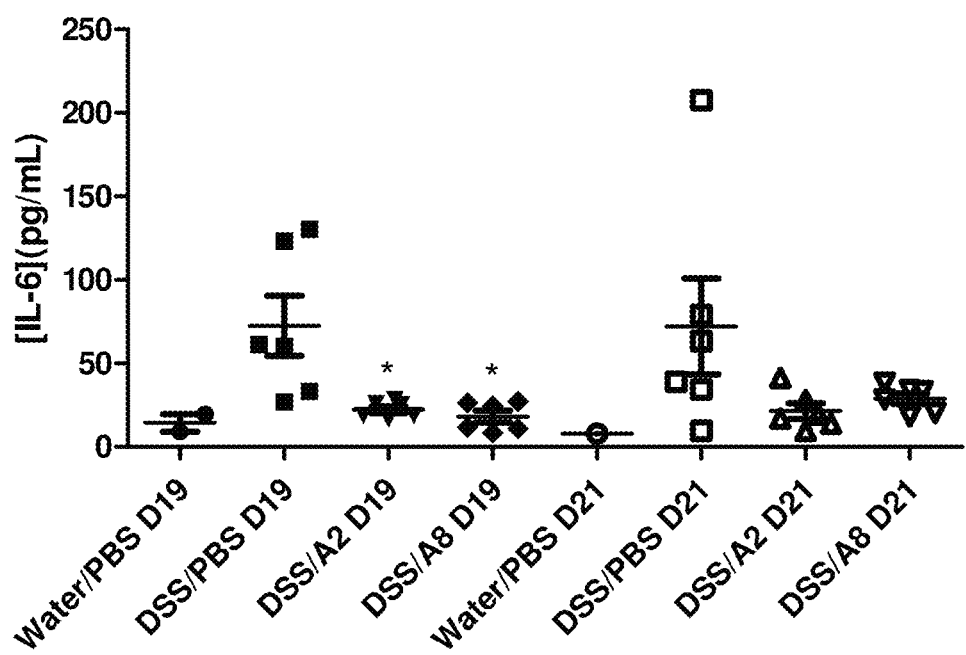

FIG. 7 shows the effect of IL-22 fusion protein A2 (SEQ ID NO: 58) at a dose of 10 or 35 µg and IL-22 fusion protein A8 (SEQ ID NO: 64) at a dose of 17 or 56 µg on the plasma IL-6 levels of mice in a DSS-induced colitis model.

DETAILED DESCRIPTION

To facilitate understanding of the disclosure set forth herein, a number of terms are defined below.

Generally, the nomenclature used herein and the laboratory procedures in biochemistry, biology, cell biology, immunology, molecular biology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, *Remington: The Science and Practice of Pharmacy,* 22nd ed.; Allen Ed.; The Pharmaceutical Press: 2012; *Handbook of Pharmaceutical Excipients,* 8th ed.; Sheskey et al., Eds.; The Pharmaceutical Press: 2017; *Handbook of Pharmaceutical Additives,* 3rd ed.; Ash and Ash Eds.; Synapse Information Resources, Inc.: 2007; *Pharmaceutical Preformulation and Formulation,* 2nd ed.; Gibson Ed.; CRC Press: 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "substantially pure" and "substantially homogeneous" mean sufficiently homogeneous to appear free of readily detectable impurities as determined by standard analytical methods used by one of ordinary skill in the art, including, but not limited to, gel electrophoresis, high performance liquid chromatography (HPLC), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% by weight of the molecules are a single compound as determined by standard analytical methods.

Interleukin-22 Fusion Proteins

In one embodiment, provided herein is a fusion protein comprising an interleukin-22 domain and an albumin binding domain, wherein the interleukin-22 domain and albumin binding domain are at the amino-terminus (N-terminus) and carboxy-terminus (C-terminus) of the fusion protein, respectively; or wherein the interleukin-22 domain and albumin binding domain are at the C-terminus and N-terminus of the fusion protein, respectively.

In one embodiment, the fusion protein provided herein comprises an interleukin-22 domain, an albumin binding domain, and optionally a peptide linker; wherein the C-terminus of the interleukin-22 domain is connected to an N-terminus of the albumin binding domain directly or via the peptide linker.

In another embodiment, the fusion protein provided herein comprises an interleukin-22 domain, an albumin binding domain, and optionally a peptide linker; wherein a C-terminus of the albumin binding domain is connected to the N-terminus of the interleukin-22 domain directly or via the peptide linker.

In another embodiment, provided herein is a fusion protein comprising an interleukin-22 domain, a peptide domain, and an albumin binding domain, wherein the peptide domain is an interleukin-22 domain, a glucagon-like peptide-2 (GLP-2) domain, or an insulin-like growth factor 1 (IGF-1) domain.

In one embodiment, the fusion protein provided herein comprises an interleukin-22 domain, a peptide domain, and an albumin binding domain; wherein the interleukin-22 domain is at the N-terminus of the fusion protein.

In another embodiment, the fusion protein provided herein comprises an interleukin-22 domain, a peptide domain, an albumin binding domain, and optionally first and second peptide linkers; wherein the C-terminus of the interleukin-22 domain is connected to the N-terminus of the peptide domain directly or via the first peptide linker, and the C-terminus of the peptide domain is connected to an N-terminus of the albumin binding domain directly or via the second peptide linker.

In yet another embodiment, the fusion protein provided herein comprises an interleukin-22 domain, a peptide domain, an albumin binding domain, and optionally first and second peptide linkers; wherein the C-terminus of the interleukin-22 domain is connected to an N-terminus of the albumin binding domain directly or via the first peptide linker, and a C-terminus of the albumin binding domain is connected to the N-terminus of the peptide domain directly or via the second peptide linker.

In yet another embodiment, the fusion protein provided herein comprises an interleukin-22 domain, a peptide domain, and an albumin binding domain; wherein the peptide domain is at the N-terminus of the fusion protein.

In yet another embodiment, the fusion protein provided herein comprises an interleukin-22 domain, a peptide domain, an albumin binding domain, and optionally first and second peptide linkers; wherein the C-terminus of the peptide domain is connected to the N-terminus of the interleukin-22 domain directly or via the first peptide linker, and the C-terminus of the interleukin-22 domain is connected to an N-terminus of the albumin binding domain directly or via the second peptide linker.

In yet another embodiment, the fusion protein provided herein comprises an interleukin-22 domain, a peptide domain, an albumin binding domain, and optionally first and second peptide linkers; wherein the C-terminus of the peptide domain is connected to an N-terminus of the albumin binding domain directly or via the first peptide linker, and a C-terminus of the albumin binding domain is connected to the N-terminus of the interleukin-22 domain directly or via the second peptide linker.

In yet another embodiment, the fusion protein provided herein comprises an interleukin-22 domain, a peptide domain, and an albumin binding domain; wherein the albumin binding domain is at the N-terminus of the fusion protein.

In yet another embodiment, the fusion protein provided herein comprises an interleukin-22 domain, a peptide domain, an albumin binding domain, and optionally first and second peptide linkers; wherein a C-terminus of the albumin binding domain is connected to the N-terminus of the interleukin-22 domain directly or via the first peptide linker, and the C-terminus of the interleukin-22 domain is connected to the N-terminus of the peptide domain directly or via the second peptide linker.

In still another embodiment, the fusion protein provided herein comprises an interleukin-22 domain, a peptide domain, an albumin binding domain, and optionally first and second peptide linkers; wherein a C-terminus of the albumin binding domain is connected to the N-terminus of the peptide domain directly or via the first peptide linker, and the C-terminus of the peptide domain is connected to the N-terminus of the interleukin-22 domain directly or via the second peptide linker.

In yet another embodiment, provided herein is a fusion protein comprising first and second interleukin-22 domains, and an albumin binding domain.

In one embodiment, the fusion protein provided herein comprises first and second interleukin-22 domains, and an albumin binding domain; wherein one of the interleukin-22 domains is at the N-terminus of the fusion protein.

In another embodiment, the fusion protein provided herein comprises first and second interleukin-22 domains, an albumin binding domain, and optionally first and second peptide linkers; wherein the C-terminus of the first interleukin-22 domain is connected to the N-terminus of the second interleukin-22 domain directly or via the first peptide linker, and the C-terminus of the second interleukin-22 domain is connected to an N-terminus of the albumin binding domain directly or via the second peptide linker.

In another embodiment, the fusion protein provided herein comprises first and second interleukin-22 domains, an albumin binding domain, and optionally first and second peptide linkers; wherein the C-terminus of the first interleukin-22 domain is connected to an N-terminus of the albumin binding domain directly or via the first peptide linker, and a C-terminus of the albumin binding domain is connected to the N-terminus of the second interleukin-22 domain directly or via the second peptide linker.

In yet another embodiment, the fusion protein provided herein comprises first and second interleukin-22 domains, and an albumin binding domain; wherein the albumin binding domain is at the N-terminus of the fusion protein.

In still another embodiment, the fusion protein provided herein comprises first and second interleukin-22 domains, an albumin binding domain, and optionally first and second peptide linkers; wherein a C-terminus of the albumin binding domain is connected to the N-terminus of the first interleukin-22 domain directly or via the first peptide linker, and the C-terminus of the first interleukin-22 domain is connected to the N-terminus of the second interleukin-22 domain directly or via the second peptide linker.

In yet another embodiment, provided herein is a fusion protein comprising an interleukin-22 domain, a GLP-2 domain, and an albumin binding domain.

In one embodiment, the fusion protein provided herein comprises an interleukin-22 domain, a GLP-2 domain, and an albumin binding domain; wherein the interleukin-22 domain is at the N-terminus of the fusion protein.

In another embodiment, the fusion protein provided herein comprises an interleukin-22 domain, a GLP-2 domain, an albumin binding domain, and optionally first and second peptide linkers; wherein the C-terminus of the interleukin-22 domain is connected to the N-terminus of the GLP-2 domain directly or via the first peptide linker, and the C-terminus of the GLP-2 domain is connected to an N-terminus of the albumin binding domain directly or via the second peptide linker.

In yet another embodiment, the fusion protein provided herein comprises an interleukin-22 domain, a GLP-2 domain, an albumin binding domain, and optionally first and second peptide linkers; wherein the C-terminus of the interleukin-22 domain is connected to an N-terminus of the albumin binding domain directly or via the first peptide linker, and a C-terminus of the albumin binding domain is connected to the N-terminus of the GLP-2 domain directly or via the second peptide linker.

In one embodiment, the fusion protein provided herein comprises an interleukin-22 domain, a GLP-2 domain, and an albumin binding domain; wherein the GLP-2 domain is at the N-terminus of the fusion protein.

In yet another embodiment, the fusion protein provided herein comprises an interleukin-22 domain, a GLP-2 domain, an albumin binding domain, and optionally first and second peptide linkers; wherein the C-terminus of the GLP-2 domain is connected to the N-terminus of the interleukin-22 domain directly or via the first peptide linker, and the C-terminus of the interleukin-22 domain is connected to an N-terminus of the albumin binding domain directly or via the second peptide linker.

In yet another embodiment, the fusion protein provided herein comprises an interleukin-22 domain, a GLP-2 domain, an albumin binding domain, and optionally first and second peptide linkers; wherein the C-terminus of the GLP-2 domain is connected to an N-terminus of the albumin binding domain directly or via the first peptide linker, and a C-terminus of the albumin binding domain is connected to the N-terminus of the interleukin-22 domain directly or via the second peptide linker.

In one embodiment, the fusion protein provided herein comprises an interleukin-22 domain, a GLP-2 domain, and an albumin binding domain; wherein the albumin binding domain is at the N-terminus of the fusion protein.

In yet another embodiment, the fusion protein provided herein comprises an interleukin-22 domain, a GLP-2 domain, an albumin binding domain, and optionally first and second peptide linkers; wherein a C-terminus of the albumin binding domain is connected to the N-terminus of the interleukin-22 domain directly or via the first peptide linker; and the C-terminus of the interleukin-22 domain is connected to the N-terminus of the GLP-2 domain directly or via the second peptide linker.

In still another embodiment, the fusion protein provided herein comprises an interleukin-22 domain, a GLP-2 domain, an albumin binding domain, and optionally first and second peptide linkers; wherein a C-terminus of the albumin binding domain is connected to the N-terminus of the GLP-2 domain directly or via the first peptide linker, and the C-terminus of the GLP-2 domain is connected to the N-terminus of the interleukin-22 domain directly or via the second peptide linker.

In yet another embodiment, provided herein is a fusion protein comprising an interleukin-22 domain, an IGF-1 domain, and an albumin binding domain.

In one embodiment, the fusion protein provided herein comprises an interleukin-22 domain, an IGF-1 domain, and an albumin binding domain; wherein the interleukin-22 domain is at the N-terminus of the fusion protein.

In another embodiment, the fusion protein provided herein comprises an interleukin-22 domain, an IGF-1 domain, an albumin binding domain, and optionally first and second peptide linkers; wherein the C-terminus of the interleukin-22 domain is connected to the N-terminus of the IGF-1 domain directly or via the first peptide linker, and the C-terminus of the IGF-1 domain is connected to an N-terminus of the albumin binding domain directly or via the second peptide linker.

In yet another embodiment, the fusion protein provided herein comprises an interleukin-22 domain, an IGF-1 domain, an albumin binding domain, and optionally first and second peptide linkers; wherein the C-terminus of the interleukin-22 domain is connected to an N-terminus of the albumin binding domain directly or via the first peptide linker, and a C-terminus of the albumin binding domain is connected to the N-terminus of the IGF-1 domain directly or via the second peptide linker.

In yet another embodiment, the fusion protein provided herein comprises an interleukin-22 domain, an IGF-1 domain, and an albumin binding domain; wherein the IGF-1 domain is at the N-terminus of the fusion protein.

In yet another embodiment, the fusion protein provided herein comprises an interleukin-22 domain, an IGF-1 domain, an albumin binding domain, and optionally first and second peptide linkers; wherein the C-terminus of the IGF-1 domain is connected to the N-terminus of the interleukin-22 domain directly or via the first peptide linker, and the C-terminus of the interleukin-22 domain is connected to an N-terminus of the albumin binding domain directly or via the second peptide linker.

In yet another embodiment, the fusion protein provided herein comprises an interleukin-22 domain, an IGF-1 domain, an albumin binding domain, and optionally first and second peptide linkers; wherein the C-terminus of the IGF-1 domain is connected to an N-terminus of the albumin binding domain directly or via the first peptide linker, and a C-terminus of the albumin binding domain is connected to the N-terminus of the interleukin-22 domain directly or via the second peptide linker.

In yet another embodiment, the fusion protein provided herein comprises an interleukin-22 domain, an IGF-1 domain, and an albumin binding domain; wherein the albumin binding domain is at the N-terminus of the fusion protein.

In yet another embodiment, the fusion protein provided herein comprises an interleukin-22 domain, an IGF-1 domain, an albumin binding domain, and optionally first and second peptide linkers; wherein a C-terminus of the albumin binding domain is connected to the N-terminus of the interleukin-22 domain directly or via the first peptide linker, and the C-terminus of the interleukin-22 domain is connected to the N-terminus of the IGF-1 domain directly or via the second peptide linker.

In still another embodiment, the fusion protein provided herein comprises an interleukin-22 domain, an IGF-1 domain, an albumin binding domain, and optionally first and second peptide linkers; wherein a C-terminus of the albumin binding domain is connected to the N-terminus of the IGF-1 domain directly or via the first peptide linker, and the C-terminus of the IGF-1 domain is connected to the N-terminus of the interleukin-22 domain directly or via the second peptide linker.

In still another embodiment, provided herein is a fusion protein comprising first and second interleukin-22 domains, a GLP-2 domain or an IGF-1 domain, and an albumin binding domain.

In one embodiment, the fusion protein provided herein comprises first and second interleukin-22 domains, a GLP-2 domain, and an albumin binding domain.

In another embodiment, the fusion protein provided herein comprises first and second interleukin-22 domains, a GLP-2 domain, and an albumin binding domain; wherein one of the interleukin-22 domains is at the N-terminus of the fusion protein.

In yet another embodiment, the fusion protein provided herein comprises first and second interleukin-22 domains, a GLP-2 domain, and an albumin binding domain; wherein the GLP-2 domain is at the N-terminus of the fusion protein.

In yet another embodiment, the fusion protein provided herein comprises first and second interleukin-22 domains, a GLP-2 domain, and an albumin binding domain; wherein the albumin binding domain is at the N-terminus of the fusion protein.

In yet another embodiment, the fusion protein provided herein comprises first and second interleukin-22 domains, a GLP-2 domain, and an albumin binding domain; wherein one of the interleukin-22 domains is at the C-terminus of the fusion protein.

In yet another embodiment, the fusion protein provided herein comprises first and second interleukin-22 domains, a GLP-2 domain, and an albumin binding domain; wherein the GLP-2 domain is at the C-terminus of the fusion protein.

In still another embodiment, the fusion protein provided herein comprises first and second interleukin-22 domains, a GLP-2 domain, and an albumin binding domain; wherein the albumin binding domain is at the C-terminus of the fusion protein.

In one embodiment, the fusion protein provided herein comprises first and second interleukin-22 domains, an IGF-1 domain, and an albumin binding domain.

In another embodiment, the fusion protein provided herein comprises first and second interleukin-22 domains, an IGF-1 domain, and an albumin binding domain; wherein one of the interleukin-22 domains is at the N-terminus of the fusion protein.

In yet another embodiment, the fusion protein provided herein comprises first and second interleukin-22 domains, an IGF-1 domain, and an albumin binding domain; wherein the IGF-1 domain is at the N-terminus of the fusion protein.

In yet another embodiment, the fusion protein provided herein comprises first and second interleukin-22 domains, an IGF-1 domain, and an albumin binding domain; wherein the albumin binding domain is at the N-terminus of the fusion protein.

In yet another embodiment, the fusion protein provided herein comprises first and second interleukin-22 domains, an IGF-1 domain, and an albumin binding domain; wherein one of the interleukin-22 domains is at the C-terminus of the fusion protein.

In yet another embodiment, the fusion protein provided herein comprises first and second interleukin-22 domains, an IGF-1 domain, and an albumin binding domain; wherein the IGF-1 domain is at the C-terminus of the fusion protein.

In still another embodiment, the fusion protein provided herein comprises first and second interleukin-22 domains, an IGF-1 domain, and an albumin binding domain; wherein the albumin binding domain is at the C-terminus of the fusion protein.

In one embodiment, provided herein is a fusion protein comprising the amino acid sequence of Formula (I):

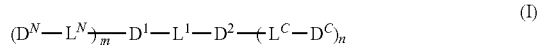
$$(D^N-L^N)_m-D^1-L^1-D^2-(L^C-D^C)_n \tag{I}$$

wherein:
- $D^1$ is an interleukin-22 domain and $D^2$ is an albumin binding domain; or $D^1$ is an albumin binding domain and $D^2$ is an interleukin-22 domain;
- $D^C$ and $D^N$ are each independently an interleukin-22 domain, a GLP-2 domain, or an IGF-1 domain;
- $L^1$, $L^C$, and $L^N$ are each independently a bond or a peptide linker; and
- m and n are each independently an integer of 0 or 1;
- wherein $D^C$ and $D^N$ are at the C-terminus and N-terminus of the fusion protein, respectively.

In certain embodiments, the amino acid sequence of the fusion protein provided herein is the amino acid sequence of Formula (I).

In another embodiment, provided herein is a fusion protein comprising the amino acid sequence of Formula (II):

$$D^1-L^1-D^2 \tag{II}$$

wherein:
- $D^1$ is an interleukin-22 domain and $D^2$ is an albumin binding domain; or $D^1$ is an albumin binding domain and $D^2$ is an interleukin-22 domain; and
- $L^1$ is a bond or a peptide linker;
- wherein $D^1$ and $D^2$ are at the N-terminus and C-terminus of the fusion protein, respectively.

In certain embodiments, the amino acid sequence of the fusion protein provided herein is the amino acid sequence of Formula (II).

In one embodiment, in Formula (II), $D^1$ is an interleukin-22 domain and $D^2$ is an albumin binding domain. In another embodiment, in Formula (II), $D^1$ is an albumin binding domain and $D^2$ is an interleukin-22 domain.

In yet another embodiment, provided herein is a fusion protein comprising the amino acid sequence of Formula (III):

$$D^N-L^N-D^1-L^1-D^2 \tag{III}$$

wherein:
- $D^1$ is an interleukin-22 domain and $D^2$ is an albumin binding domain; or $D^1$ is an albumin binding domain and $D^2$ is an interleukin-22 domain;
- $D^N$ is an interleukin-22 domain, a GLP-2 domain, or an IGF-1 domain; and
- $L^1$ and $L^N$ are each independently a bond or a peptide linker;
- wherein $D^2$ and $D^N$ are at the C-terminus and N-terminus of the fusion protein, respectively.

In certain embodiments, the amino acid sequence of the fusion protein provided herein is the amino acid sequence of Formula (III).

In one embodiment, in Formula (III), $D^1$ is an interleukin-22 domain, $D^2$ is an albumin binding domain, and $D^N$ is an interleukin-22 domain. In another embodiment, in Formula (III), $D^1$ is an interleukin-22 domain, $D^2$ is an albumin binding domain, and $D^N$ is a GLP-2 domain. In yet another embodiment, in Formula (III), $D^1$ is an interleukin-22 domain, $D^2$ is an albumin binding domain, and $D^N$ is an IGF-1 domain.

In one embodiment, in Formula (III), $D^1$ is an albumin binding domain, $D^2$ is an interleukin-22 domain, and $D^N$ is an interleukin-22 domain. In another embodiment, in Formula (III), $D^1$ is an albumin binding domain, $D^2$ is an interleukin-22 domain, and $D^N$ is a GLP-2 domain. In yet another embodiment, in Formula (III), $D^1$ is an albumin binding domain, $D^2$ is an interleukin-22 domain, and $D^N$ is an IGF-1 domain.

In yet another embodiment, provided herein is a fusion protein comprising the amino acid sequence of Formula (IV):

$$D^1-L^1-D^2-L^C-D^C \tag{IV}$$

wherein:
- $D^1$ is an interleukin-22 domain and $D^2$ is an albumin binding domain; or $D^1$ is an albumin binding domain and $D^2$ is an interleukin-22 domain;
- $D^C$ is a GLP-2 domain or an IGF-1 domain; and
- $L^1$ and $L^C$ are each independently a bond or a peptide linker;

wherein D¹ and D^C are at the N-terminus and C-terminus of the fusion protein, respectively.

In certain embodiments, the amino acid sequence of the fusion protein provided herein is the amino acid sequence of Formula (IV).

In one embodiment, in Formula (IV), D¹ is an interleukin-22 domain, D² is an albumin binding domain, and D^C is a GLP-2 domain. In another embodiment, in Formula (IV), D¹ is an interleukin-22 domain, D² is an albumin binding domain, and D^C is an IGF-1 domain.

In one embodiment, in Formula (IV), D¹ is an albumin binding domain, D² is an interleukin-22 domain, and D^C is a GLP-2 domain. In another embodiment, in Formula (IV), D¹ is an albumin binding domain, D² is an interleukin-22 domain, and D^C is an IGF-1 domain.

In still another embodiment, provided herein is a fusion protein comprising the amino acid sequence of Formula (V):

(V)

wherein:
D¹ is an interleukin-22 domain and D² is an albumin binding domain; or D¹ is an albumin binding domain and D² is an interleukin-22 domain;
D^C is an interleukin-22 domain, and D^N is a GLP-2 domain or an IGF-1 domain; or D^C is a GLP-2 domain or an IGF-1 domain, and D^N is an interleukin-22 domain; and
L¹, L^C, and L^N are each independently a bond or a peptide linker;
wherein D^C and D^N are at the C-terminus and N-terminus of the fusion protein, respectively.

In certain embodiments, the amino acid sequence of the fusion protein provided herein is the amino acid sequence of Formula (V).

In one embodiment, in Formula (V), D¹ is an interleukin-22 domain, D² is an albumin binding domain, D^C is an interleukin-22 domain, and D^N is a GLP-2 domain. In another embodiment, in Formula (V), D¹ is an interleukin-22 domain, D² is an albumin binding domain, D^C is an interleukin-22 domain, and D^N is an IGF-1 domain. In yet another embodiment, in Formula (V), D¹ is an interleukin-22 domain, D² is an albumin binding domain, D^C is a GLP-2 domain, and D^N is an interleukin-22 domain. In still another embodiment, in Formula (V), D¹ is an interleukin-22 domain, D² is an albumin binding domain, D^C is an IGF-1 domain, and D^N is an interleukin-22 domain.

In one embodiment, in Formula (V), D¹ is an albumin binding domain, D² is an interleukin-22 domain, D^C is an interleukin-22 domain, and D^N is a GLP-2 domain. In another embodiment, in Formula (V), D¹ is an albumin binding domain, D² is an interleukin-22 domain, D^C is an interleukin-22 domain, and D^N is an IGF-1 domain. In yet another embodiment, in Formula (V), D¹ is an albumin binding domain, D² is an interleukin-22 domain, D^C is a GLP-2 domain, and D^N is an interleukin-22 domain. In still another embodiment, in Formula (V), D¹ is an albumin binding domain, D² is an interleukin-22 domain, D^C is an IGF-1 domain, and D^N is an interleukin-22 domain.

In certain embodiments, the albumin binding domain extends the half-life of the interleukin-22 domain in vivo as compared to the corresponding free interleukin-22, e.g., interleukin-22 of SEQ ID NO: 1, 2, 3, or 4. In certain embodiments, the albumin binding domain extends the half-life of the GLP-2 domain in vivo as compared to the corresponding free GLP-2, e.g., GLP-2 of SEQ ID NO: 5, 6, or 7. In certain embodiments, the albumin binding domain extends the half-life of the IGF-1 domain in vivo as compared to the corresponding free IGF-1, e.g., IGF-1 of SEQ ID NO: 8 or 9.

In one embodiment, each interleukin-22 domain in the fusion protein provided herein independently comprises the amino acid sequence of a wide-type interleukin-22, or a variant, fragment, or mutein thereof. In another embodiment, each interleukin-22 domain in the fusion protein provided herein independently comprises the amino acid sequence of a wild-type human interleukin-22, or a variant, fragment, or mutein thereof.

In one embodiment, each interleukin-22 domain in the fusion protein provided herein independently comprises the amino acid sequence of SEQ ID NO: 1, 2, 3, or 4. In another embodiment, each interleukin-22 domain in the fusion protein provided herein comprises the amino acid sequence of SEQ ID NO: 1. In yet another embodiment, each interleukin-22 domain in the fusion protein provided herein comprises the amino acid sequence of SEQ ID NO: 2. In yet another embodiment, each interleukin-22 domain in the fusion protein provided herein comprises the amino acid sequence of SEQ ID NO: 3. In still another embodiment, each interleukin-22 domain in the fusion protein provided herein comprises the amino acid sequence of SEQ ID NO: 4.

In certain embodiments, each interleukin-22 domain in the fusion protein provided herein independently comprises an amino acid sequence that is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to the amino acid sequence of SEQ ID NO: 1.

In certain embodiments, each interleukin-22 domain in the fusion protein provided herein independently comprises an amino acid sequence that is no less than about 70% identical to the amino acid sequence of SEQ ID NO: 1. In certain embodiments, each interleukin-22 domain in the fusion protein provided herein independently comprises an amino acid sequence that is no less than about 75% identical to the amino acid sequence of SEQ ID NO: 1. In certain embodiments, each interleukin-22 domain in the fusion protein provided herein independently comprises an amino acid sequence that is no less than about 80% identical to the amino acid sequence of SEQ ID NO: 1. In certain embodiments, each interleukin-22 domain in the fusion protein provided herein independently comprises an amino acid sequence that is no less than about 85% identical to the amino acid sequence of SEQ ID NO: 1. In certain embodiments, each interleukin-22 domain in the fusion protein provided herein independently comprises an amino acid sequence that is no less than about 90% identical to the amino acid sequence of SEQ ID NO: 1. In certain embodiments, each interleukin-22 domain in the fusion protein provided herein independently comprises an amino acid sequence that is no less than about 91% identical to the amino acid sequence of SEQ ID NO: 1. In certain embodiments, each interleukin-22 domain in the fusion protein provided herein independently comprises an amino acid sequence that is no less than about 92% identical to the amino acid sequence of SEQ ID NO: 1. In certain embodiments, each interleukin-22 domain in the fusion protein provided herein independently comprises an amino acid sequence that is no less than about 93% identical to the amino acid sequence of SEQ ID NO: 1. In certain embodiments, each interleukin-22 domain in the fusion protein provided herein independently comprises an amino acid sequence that is no less than about 94% identical to the amino acid sequence of SEQ ID NO: 1. In certain embodiments, each interleukin-22 domain in the fusion protein provided herein independently comprises an amino acid sequence that is no less than about 95% identical to the amino acid sequence of SEQ ID NO: 1. In certain embodiments, each interleukin-22 domain in the fusion protein provided herein independently comprises an amino acid sequence that is no less than about 96% identical to the amino acid sequence of SEQ ID NO: 1. In certain embodiments, each interleukin-22 domain in the fusion protein provided herein independently comprises an amino acid sequence that is no less than about 97% identical to the amino acid sequence of SEQ ID NO: 1. In certain embodiments, each interleukin-22 domain in the fusion protein provided herein independently comprises an amino acid sequence that is no less than about 98% identical to the amino acid sequence of SEQ ID NO: 1. In certain embodiments, each interleukin-22 domain in the fusion protein provided herein independently comprises an amino acid sequence that is no less than about 99% identical to the amino acid sequence of SEQ ID NO: 1.

In certain embodiments, each interleukin-22 domain in the fusion protein provided herein independently comprises an amino acid sequence that is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to the amino acid sequence of SEQ ID NO: 2.

In certain embodiments, each interleukin-22 domain in the fusion protein provided herein independently comprises an amino acid sequence that is no less than about 70% identical to the amino acid sequence of SEQ ID NO: 2. In certain embodiments, each interleukin-22 domain in the fusion protein provided herein independently comprises an amino acid sequence that is no less than about 75% identical to the amino acid sequence of SEQ ID NO: 2. In certain embodiments, each interleukin-22 domain in the fusion protein provided herein independently comprises an amino acid sequence that is no less than about 80% identical to the amino acid sequence of SEQ ID NO: 2. In certain embodiments, each interleukin-22 domain in the fusion protein provided herein independently comprises an amino acid sequence that is no less than about 85% identical to the amino acid sequence of SEQ ID NO: 2. In certain embodiments, each interleukin-22 domain in the fusion protein provided herein independently comprises an amino acid sequence that is no less than about 90% identical to the amino acid sequence of SEQ ID NO: 2. In certain embodiments, each interleukin-22 domain in the fusion protein provided herein independently comprises an amino acid sequence that is no less than about 91% identical to the amino acid sequence of SEQ ID NO: 2. In certain embodiments, each interleukin-22 domain in the fusion protein provided herein independently comprises an amino acid sequence that is no less than about 92% identical to the amino acid sequence of SEQ ID NO: 2. In certain embodiments, each interleukin-22 domain in the fusion protein provided herein independently comprises an amino acid sequence that is no less than about 93% identical to the amino acid sequence of SEQ ID NO: 2. In certain embodiments, each interleukin-22 domain in the fusion protein provided herein independently comprises an amino acid sequence that is no less than about 94% identical to the amino acid sequence of SEQ ID NO: 2. In certain embodiments, each interleukin-22 domain in the fusion protein provided herein independently comprises an amino acid sequence that is no less than about 95% identical to the amino acid sequence of SEQ ID NO: 2. In certain embodiments, each interleukin-22 domain in the fusion protein provided herein independently comprises an amino acid sequence that is no less than about 96% identical to the amino acid sequence of SEQ ID NO: 2. In certain embodiments, each interleukin-22 domain in the fusion protein provided herein independently comprises an amino acid sequence that is no less than about 97% identical to the amino acid sequence of SEQ ID NO: 2. In certain embodiments, each interleukin-22 domain in the fusion protein provided herein independently comprises an amino acid sequence that is no less than about 98% identical to the amino acid sequence of SEQ ID NO: 2. In certain embodiments, each interleukin-22 domain in the fusion protein provided herein independently comprises an amino acid sequence that is no less than about 99% identical to the amino acid sequence of SEQ ID NO: 2.

In certain embodiments, each interleukin-22 domain in the fusion protein provided herein independently comprises an amino acid sequence that is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to the amino acid sequence of SEQ ID NO: 3.

In certain embodiments, each interleukin-22 domain in the fusion protein provided herein independently comprises an amino acid sequence that is no less than about 70% identical to the amino acid sequence of SEQ ID NO: 3. In certain embodiments, each interleukin-22 domain in the fusion protein provided herein independently comprises an amino acid sequence that is no less than about 75% identical to the amino acid sequence of SEQ ID NO: 3. In certain embodiments, each interleukin-22 domain in the fusion protein provided herein independently comprises an amino acid sequence that is no less than about 80% identical to the amino acid sequence of SEQ ID NO: 3. In certain embodiments, each interleukin-22 domain in the fusion protein provided herein independently comprises an amino acid sequence that is no less than about 85% identical to the amino acid sequence of SEQ ID NO: 3. In certain embodiments, each interleukin-22 domain in the fusion protein provided herein independently comprises an amino acid sequence that is no less than about 90% identical to the amino acid sequence of SEQ ID NO: 3. In certain embodiments, each interleukin-22 domain in the fusion protein provided herein independently comprises an amino acid sequence that is no less than about 91% identical to the amino acid sequence of SEQ ID NO: 3. In certain embodiments, each interleukin-22 domain in the fusion protein provided herein independently comprises an amino acid sequence that is no less than about 92% identical to the amino acid sequence of SEQ ID NO: 3. In certain embodiments, each interleukin-22 domain in the fusion protein provided herein independently comprises an amino acid sequence that is no less than about 93% identical to the amino acid sequence of SEQ ID NO: 3. In certain embodiments, each interleukin-22 domain in the fusion protein provided herein independently comprises an amino acid sequence that is no less than about 94% identical to the amino acid sequence of SEQ ID NO: 3. In certain embodiments, each interleukin-22 domain in the fusion protein provided herein independently comprises an amino acid sequence that is no less than about 95% identical to the amino acid sequence of SEQ ID NO: 3. In certain embodiments, each interleukin-22 domain in the fusion protein provided herein independently comprises an amino acid sequence that is no less than about 96% identical to the amino acid sequence of SEQ ID NO: 3. In certain embodiments, each interleukin-22 domain in the fusion protein provided herein independently comprises an amino acid sequence that is no less than about 97% identical to the amino acid sequence of SEQ ID NO: 3. In certain embodiments, each interleukin-22 domain in the fusion protein provided herein independently comprises an amino acid sequence that is no less than about 98% identical to the amino acid sequence of SEQ ID NO: 3. In certain embodiments, each interleukin-22 domain in the fusion protein provided herein independently comprises an amino acid sequence that is no less than about 99% identical to the amino acid sequence of SEQ ID NO: 3.

In certain embodiments, each interleukin-22 domain in the fusion protein provided herein independently comprises an amino acid sequence that is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to the amino acid sequence of SEQ ID NO: 4.

In certain embodiments, each interleukin-22 domain in the fusion protein provided herein independently comprises an amino acid sequence that is no less than about 70% identical to the amino acid sequence of SEQ ID NO: 4. In certain embodiments, each interleukin-22 domain in the fusion protein provided herein independently comprises an amino acid sequence that is no less than about 75% identical to the amino acid sequence of SEQ ID NO: 4. In certain embodiments, each interleukin-22 domain in the fusion protein provided herein independently comprises an amino acid sequence that is no less than about 80% identical to the amino acid sequence of SEQ ID NO: 4. In certain embodiments, each interleukin-22 domain in the fusion protein provided herein independently comprises an amino acid sequence that is no less than about 85% identical to the amino acid sequence of SEQ ID NO: 4. In certain embodiments, each interleukin-22 domain in the fusion protein provided herein independently comprises an amino acid sequence that is no less than about 90% identical to the amino acid sequence of SEQ ID NO: 4. In certain embodiments, each interleukin-22 domain in the fusion protein provided herein independently comprises an amino acid sequence that is no less than about 91% identical to the amino acid sequence of SEQ ID NO: 4. In certain embodiments, each interleukin-22 domain in the fusion protein provided herein independently comprises an amino acid sequence that is no less than about 92% identical to the amino acid sequence of SEQ ID NO: 4. In certain embodiments, each interleukin-22 domain in the fusion protein provided herein independently comprises an amino acid sequence that is no less than about 93% identical to the amino acid sequence of SEQ ID NO: 4. In certain embodiments, each interleukin-22 domain in the fusion protein provided herein independently comprises an amino acid sequence that is no less than about 94% identical to the amino acid sequence of SEQ ID NO: 4. In certain embodiments, each interleukin-22 domain in the fusion protein provided herein independently comprises an amino acid sequence that is no less than about 95% identical to the amino acid sequence of SEQ ID NO: 4. In certain embodiments, each interleukin-22 domain in the fusion protein provided herein independently comprises an amino acid sequence that is no less than about 96% identical to the amino acid sequence of SEQ ID NO: 4. In certain embodiments, each interleukin-22 domain in the fusion protein provided herein independently comprises an amino acid sequence that is no less than about 97% identical to the amino acid sequence of SEQ ID NO: 4. In certain embodiments, each interleukin-22 domain in the fusion protein provided herein independently comprises an amino acid sequence that is no less than about 98% identical to the amino acid sequence of SEQ ID NO: 4. In certain embodiments, each interleukin-22 domain in the fusion protein provided herein independently comprises an amino acid sequence that is no less than about 99% identical to the amino acid sequence of SEQ ID NO: 4.

In one embodiment, the GLP-2 domain in the fusion protein provided herein comprises the amino acid sequence of a wide-type GLP-2, or a variant, fragment, or mutein thereof. In another embodiment, the GLP-2 domain in the fusion protein provided herein comprises the amino acid sequence of a wild-type human GLP-2, or a variant, fragment, or mutein thereof.

In one embodiment, the GLP-2 domain comprises the amino acid sequence of SEQ ID NO: 5, 6, or 7. In another embodiment, the GLP-2 domain comprises the amino acid sequence of SEQ ID NO: 5. In yet another embodiment, the GLP-2 domain comprises the amino acid sequence of SEQ ID NO: 6. In still another embodiment, the GLP-2 domain comprises the amino acid sequence of SEQ ID NO: 7.

In certain embodiments, the GLP-2 domain in the fusion protein provided herein comprises an amino acid sequence that is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to the amino acid sequence of SEQ ID NO: 5.

In certain embodiments, the GLP-2 domain in the fusion protein provided herein comprises an amino acid sequence that is no less than about 70% identical to the amino acid sequence of SEQ ID NO: 5. In certain embodiments, the GLP-2 domain in the fusion protein provided herein comprises an amino acid sequence that is no less than about 75% identical to the amino acid sequence of SEQ ID NO: 5. In certain embodiments, the GLP-2 domain in the fusion protein provided herein comprises an amino acid sequence that is no less than about 80% identical to the amino acid sequence of SEQ ID NO: 5. In certain embodiments, the GLP-2 domain in the fusion protein provided herein comprises an amino acid sequence that is no less than about 85% identical to the amino acid sequence of SEQ ID NO: 5. In certain embodiments, the GLP-2 domain in the fusion protein provided herein comprises an amino acid sequence that is no less than about 90% identical to the amino acid sequence of SEQ ID NO: 5. In certain embodiments, the GLP-2 domain in the fusion protein provided herein comprises an amino acid sequence that is no less than about 91% identical to the amino acid sequence of SEQ ID NO: 5. In certain embodiments, the GLP-2 domain in the fusion protein provided herein comprises an amino acid sequence that is no less than about 92% identical to the amino acid sequence of SEQ ID NO: 5. In certain embodiments, the GLP-2 domain in the fusion protein provided herein comprises an amino acid sequence that is no less than about 93% identical to the amino acid sequence of SEQ ID NO: 5. In certain embodiments, the GLP-2 domain in the fusion protein provided herein comprises an amino acid sequence that is no less than about 94% identical to the amino acid sequence of SEQ ID NO: 5. In certain embodiments, the GLP-2 domain in the fusion protein provided herein comprises an amino acid sequence that is no less than about 95% identical to the amino acid sequence of SEQ ID NO: 5. In certain embodiments, the GLP-2 domain in the fusion protein provided herein comprises an amino acid sequence that is no less than about 96% identical to the amino acid sequence of SEQ ID NO: 5. In certain embodiments, the GLP-2 domain in the fusion protein provided herein comprises an amino acid sequence that is no less than about 97% identical to the amino acid sequence of SEQ ID NO: 5. In certain embodiments, the GLP-2 domain in the fusion protein provided herein comprises an amino acid sequence that is no less than about 98% identical to the amino acid sequence of SEQ ID NO: 5. In certain embodiments, the GLP-2 domain in the fusion protein provided herein comprises an amino acid sequence that is no less than about 99% identical to the amino acid sequence of SEQ ID NO: 5.

In certain embodiments, the GLP-2 domain in the fusion protein provided herein comprises an amino acid sequence that is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to the amino acid sequence of SEQ ID NO: 6.

In certain embodiments, the GLP-2 domain in the fusion protein provided herein comprises an amino acid sequence that is no less than about 70% identical to the amino acid sequence of SEQ ID NO: 6. In certain embodiments, the GLP-2 domain in the fusion protein provided herein comprises an amino acid sequence that is no less than about 75% identical to the amino acid sequence of SEQ ID NO: 6. In certain embodiments, the GLP-2 domain in the fusion protein provided herein comprises an amino acid sequence that is no less than about 80% identical to the amino acid sequence of SEQ ID NO: 6. In certain embodiments, the GLP-2 domain in the fusion protein provided herein comprises an amino acid sequence that is no less than about 85% identical to the amino acid sequence of SEQ ID NO: 6. In certain embodiments, the GLP-2 domain in the fusion protein provided herein comprises an amino acid sequence that is no less than about 90% identical to the amino acid sequence of SEQ ID NO: 6. In certain embodiments, the GLP-2 domain in the fusion protein provided herein comprises an amino acid sequence that is no less than about 91% identical to the amino acid sequence of SEQ ID NO: 6. In certain embodiments, the GLP-2 domain in the fusion protein provided herein comprises an amino acid sequence that is no less than about 92% identical to the amino acid sequence of SEQ ID NO: 6. In certain embodiments, the GLP-2 domain in the fusion protein provided herein comprises an amino acid sequence that is no less than about 93% identical to the amino acid sequence of SEQ ID NO: 6. In certain embodiments, the GLP-2 domain in the fusion protein provided herein comprises an amino acid sequence that is no less than about 94% identical to the amino acid sequence of SEQ ID NO: 6. In certain embodiments, the GLP-2 domain in the fusion protein provided herein comprises an amino acid sequence that is no less than about 95% identical to the amino acid sequence of SEQ ID NO: 6. In certain embodiments, the GLP-2 domain in the fusion protein provided herein comprises an amino acid sequence that is no less than about 96% identical to the amino acid sequence of SEQ ID NO: 6. In certain embodiments, the GLP-2 domain in the fusion protein provided herein comprises an amino acid sequence that is no less than about 97% identical to the amino acid sequence of SEQ ID NO: 6. In certain embodiments, the GLP-2 domain in the fusion protein provided herein comprises an amino acid sequence that is no less than about 98% identical to the amino acid sequence of SEQ ID NO: 6. In certain embodiments, the GLP-2 domain in the fusion protein provided herein comprises an amino acid sequence that is no less than about 99% identical to the amino acid sequence of SEQ ID NO: 6.

In certain embodiments, the GLP-2 domain in the fusion protein provided herein comprises an amino acid sequence that is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to the amino acid sequence of SEQ ID NO: 7.

In certain embodiments, the GLP-2 domain in the fusion protein provided herein comprises an amino acid sequence that is no less than about 70% identical to the amino acid sequence of SEQ ID NO: 7. In certain embodiments, the GLP-2 domain in the fusion protein provided herein comprises an amino acid sequence that is no less than about 75% identical to the amino acid sequence of SEQ ID NO: 7. In certain embodiments, the GLP-2 domain in the fusion protein provided herein comprises an amino acid sequence that is no less than about 80% identical to the amino acid sequence of SEQ ID NO: 7. In certain embodiments, the GLP-2 domain in the fusion protein provided herein comprises an amino acid sequence that is no less than about 85% identical to the amino acid sequence of SEQ ID NO: 7. In certain embodiments, the GLP-2 domain in the fusion protein provided herein comprises an amino acid sequence that is no less than about 90% identical to the amino acid sequence of SEQ ID NO: 7. In certain embodiments, the GLP-2 domain in the fusion protein provided herein comprises an amino acid sequence that is no less than about 91% identical to the amino acid sequence of SEQ ID NO: 7. In certain embodiments, the GLP-2 domain in the fusion protein provided herein comprises an amino acid sequence that is no less than about 92% identical to the amino acid sequence of SEQ ID NO: 7. In certain embodiments, the GLP-2 domain in the fusion protein provided herein comprises an amino acid sequence that is no less than about 93% identical to the amino acid sequence of SEQ ID NO: 7. In certain embodiments, the GLP-2 domain in the fusion protein provided herein comprises an amino acid sequence that is no less than about 94% identical to the amino acid sequence of SEQ ID NO: 7. In certain embodiments, the GLP-2 domain in the fusion protein provided herein comprises an amino acid sequence that is no less than about 95% identical to the amino acid sequence of SEQ ID NO: 7. In certain embodiments, the GLP-2 domain in the fusion protein provided herein comprises an amino acid sequence that is no less than about 96% identical to the amino acid sequence of SEQ ID NO: 7. In certain embodiments, the GLP-2 domain in the fusion protein provided herein comprises an amino acid sequence that is no less than about 97% identical to the amino acid sequence of SEQ ID NO: 7. In certain embodiments, the GLP-2 domain in the fusion protein provided herein comprises an amino acid sequence that is no less than about 98% identical to the amino acid sequence of SEQ ID NO: 7. In certain embodiments, the GLP-2 domain in the fusion protein provided herein comprises an amino acid sequence that is no less than about 99% identical to the amino acid sequence of SEQ ID NO: 7.

In one embodiment, the IGF-1 domain in the fusion protein provided herein comprises the amino acid sequence of a wide-type IGF-1, or a variant, fragment, or mutein thereof. In another embodiment, the IGF-1 domain in the fusion protein provided herein comprises the amino acid sequence of a wild-type human IGF-1, or a variant, fragment, or mutein thereof.

In one embodiment, the IGF-1 domain in the fusion protein provided herein comprises the amino acid sequence of SEQ ID NO: 8 or 9. In another embodiment, the IGF-1 domain in the fusion protein provided herein comprises the amino acid sequence of SEQ ID NO: 8. In another embodiment, the IGF-1 domain in the fusion protein provided herein comprises the amino acid sequence of SEQ ID NO: 9.

In certain embodiments, the IGF-1 domain in the fusion protein provided herein comprises an amino acid sequence that is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to the amino acid sequence of SEQ ID NO: 8.

In certain embodiments, the IGF-1 domain in the fusion protein provided herein comprises an amino acid sequence that is no less than about 70% identical to the amino acid sequence of SEQ ID NO: 8. In certain embodiments, the IGF-1 domain in the fusion protein provided herein comprises an amino acid sequence that is no less than about 75% identical to the amino acid sequence of SEQ ID NO: 8. In certain embodiments, the IGF-1 domain in the fusion protein provided herein comprises an amino acid sequence that is no less than about 80% identical to the amino acid sequence of SEQ ID NO: 8. In certain embodiments, the IGF-1 domain in the fusion protein provided herein comprises an amino acid sequence that is no less than about 85% identical to the amino acid sequence of SEQ ID NO: 8. In certain embodiments, the IGF-1 domain in the fusion protein provided herein comprises an amino acid sequence that is no less than about 90% identical to the amino acid sequence of SEQ ID NO: 8. In certain embodiments, the IGF-1 domain in the fusion protein provided herein comprises an amino acid sequence that is no less than about 91% identical to the amino acid sequence of SEQ ID NO: 8. In certain embodiments, the IGF-1 domain in the fusion protein provided herein comprises an amino acid sequence that is no less than about 92% identical to the amino acid sequence of SEQ ID NO: 8. In certain embodiments, the IGF-1 domain in the fusion protein provided herein comprises an amino acid sequence that is no less than about 93% identical to the amino acid sequence of SEQ ID NO: 8. In certain embodiments, the IGF-1 domain in the fusion protein provided herein comprises an amino acid sequence that is no less than about 94% identical to the amino acid sequence of SEQ ID NO: 8. In certain embodiments, the IGF-1 domain in the fusion protein provided herein comprises an amino acid sequence that is no less than about 95% identical to the amino acid sequence of SEQ ID NO: 8. In certain embodiments, the IGF-1 domain in the fusion protein provided herein comprises an amino acid sequence that is no less than about 96% identical to the amino acid sequence of SEQ ID NO: 8. In certain embodiments, the IGF-1 domain in the fusion protein provided herein comprises an amino acid sequence that is no less than about 97% identical to the amino acid sequence of SEQ ID NO: 8. In certain embodiments, the IGF-1 domain in the fusion protein provided herein comprises an amino acid sequence that is no less than about 98% identical to the amino acid sequence of SEQ ID NO: 8. In certain embodiments, the IGF-1 domain in the fusion protein provided herein comprises an amino acid sequence that is no less than about 99% identical to the amino acid sequence of SEQ ID NO: 8.

In certain embodiments, the IGF-1 domain in the fusion protein provided herein comprises an amino acid sequence that is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to the amino acid sequence of SEQ ID NO: 9.

In certain embodiments, the IGF-1 domain in the fusion protein provided herein comprises an amino acid sequence that is no less than about 70% identical to the amino acid sequence of SEQ ID NO: 9. In certain embodiments, the IGF-1 domain in the fusion protein provided herein comprises an amino acid sequence that is no less than about 75% identical to the amino acid sequence of SEQ ID NO: 9. In certain embodiments, the IGF-1 domain in the fusion protein provided herein comprises an amino acid sequence that is no less than about 80% identical to the amino acid sequence of SEQ ID NO: 9. In certain embodiments, the IGF-1 domain in the fusion protein provided herein comprises an amino acid sequence that is no less than about 85% identical to the amino acid sequence of SEQ ID NO: 9. In certain embodiments, the IGF-1 domain in the fusion protein provided herein comprises an amino acid sequence that is no less than about 90% identical to the amino acid sequence of SEQ ID NO: 9. In certain embodiments, the IGF-1 domain in the fusion protein provided herein comprises an amino acid sequence that is no less than about 91% identical to the amino acid sequence of SEQ ID NO: 9. In certain embodiments, the IGF-1 domain in the fusion protein provided herein comprises an amino acid sequence that is no less than about 92% identical to the amino acid sequence of SEQ ID NO: 9. In certain embodiments, the IGF-1 domain in the fusion protein provided herein comprises an amino acid sequence that is no less than about 93% identical to the amino acid sequence of SEQ ID NO: 9. In certain embodiments, the IGF-1 domain in the fusion protein provided herein comprises an amino acid sequence that is no less than about 94% identical to the amino acid sequence of SEQ ID NO: 9. In certain embodiments, the IGF-1 domain in the fusion protein provided herein comprises an amino acid sequence that is no less than about 95% identical to the amino acid sequence of SEQ ID NO: 9. In certain embodiments, the IGF-1 domain in the fusion protein provided herein comprises an amino acid sequence that is no less than about 96% identical to the amino acid sequence of SEQ ID NO: 9. In certain embodiments, the IGF-1 domain in the fusion protein provided herein comprises an amino acid sequence that is no less than about 97% identical to the amino acid sequence of SEQ ID NO: 9. In certain embodiments, the IGF-1 domain in the fusion protein provided herein comprises an amino acid sequence that is no less than about 98% identical to the amino acid sequence of SEQ ID NO: 9. In certain embodiments, the IGF-1 domain in the fusion protein provided herein comprises an amino acid sequence that is no less than about 99% identical to the amino acid sequence of SEQ ID NO: 9.

In one embodiment, the albumin binding domain comprises an amino acid sequence of an antibody or a fragment thereof that binds to an albumin. In another embodiment, the albumin binding domain comprises an amino acid sequence of an antibody or a fragment thereof that binds to a human serum albumin (HSA).

In certain embodiments, the fusion protein provided herein comprising an albumin binding domain binds to an HSA with a $K_d$ ranging from about 10 pM to about 1,000 nM. In certain embodiments, the fusion protein provided herein comprising an albumin binding domain binds to an HSA with a $K_d$ ranging from about 1 nM to about 500 nM. In certain embodiments, the fusion protein provided herein comprising an albumin binding domain binds to an HSA with a $K_d$ ranging from about 1 nM to about 200 nM. In certain embodiments, the fusion protein provided herein comprising an albumin binding domain binds to an HSA with a $K_d$ ranging from about 1 nM to about 100 nM.

In one embodiment, the albumin binding domain comprises (i) a complementarity determining region 1 (CDR1) of SEQ ID NO: 10, a complementarity determining region 2 (CDR2) of SEQ ID NO: 11, and a complementarity determining region 3 (CDR3) of SEQ ID NO: 12; or (ii) a CDR1 of SEQ ID NO: 18, a CDR2 of SEQ ID NO: 19, and a CDR3 of SEQ ID NO: 20. In another embodiment, the albumin binding domain comprises a CDR1 of SEQ ID NO: 10, a CDR2 of SEQ ID NO: 11, and a CDR3 of SEQ ID NO: 12. In yet another embodiment, the albumin binding domain comprises a CDR1 of SEQ ID NO: 18, a CDR2 of SEQ ID NO: 19, and a CDR3 of SEQ ID NO: 20. In yet another embodiment, the albumin binding domain comprises the amino acid sequence of SEQ ID NO: 17 or 24. In yet another embodiment, the albumin binding domain comprises the amino acid sequence of SEQ ID NO: 17. In still another embodiment, the albumin binding domain comprises the amino acid sequence of SEQ ID NO: 24.

In certain embodiments, the albumin binding domain comprises an amino acid sequence of a human anti-HSA antibody or a fragment thereof. In certain embodiments, the albumin binding domain comprises an amino acid sequence of a humanized anti-HSA antibody.

In certain embodiments, the albumin binding domain is an anti-HSA antibody disclosed in WO 2019/246004 A1 or WO 2020/172528 A1, the disclosure of each of which is incorporated herein by reference in its entirety.

In another embodiment, the albumin binding domain comprises an amino acid sequence of a single domain antibody (sdAb) that binds to an albumin. In certain embodiments, the albumin binding domain comprises an amino acid sequence of an sdAb that binds to an HSA.

In certain embodiments, the sdAb binds to an HSA with a $K_d$ ranging from about 10 pM to about 1,000 nM. In certain embodiments, the sdAb binds to an HSA with a $K_d$ ranging from about 1 nM to about 500 nM. In certain embodiments, the sdAb binds to an HSA with a $K_d$ ranging from about 1 nM to about 200 nM. In certain embodiments, the sdAb binds to an HSA with a $K_d$ ranging from about 1 nM to about 100 nM.

In one embodiment, the albumin binding domain is an sdAb domain. In another embodiment, the sdAb domain comprises (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20. In yet another embodiment, the sdAb domain comprises a CDR1 of SEQ ID NO: 10, a CDR2 of SEQ ID NO: 11, and a CDR3 of SEQ ID NO: 12. In yet another embodiment, the sdAb domain comprises a CDR1 of SEQ ID NO: 18, a CDR2 of SEQ ID NO: 19, and a CDR3 of SEQ ID NO: 20.

In one embodiment, the sdAb domain has the structure of FR1-CDR1-FR2-CDR2-FR3-CDR3-FR4, wherein:
  CDR1, CDR2, and CDR3 are:
    (i) CDR1 of SEQ ID NO: 10, CDR2 of SEQ ID NO: 11, and CDR3 of SEQ ID NO: 12; or
    (ii) CDR1 of SEQ ID NO: 18, CDR2 of SEQ ID NO: 19, and CDR3 of SEQ ID NO: 20;
  FR1 is the amino acid sequence of SEQ ID NO: 13 or 21;
  FR2 is the amino acid sequence of SEQ ID NO: 14 or 22;
  FR3 is the amino acid sequence of SEQ ID NO: 15; and
  FR4 is the amino acid sequence of SEQ ID NO: 16 or 23;
wherein FR1 and FR4 are at the N-terminus and C-terminus of the sdAb domain, respectively.

In another embodiment, the sdAb domain has the structure of FR1-CDR1-FR2-CDR2-FR3-CDR3-FR4, wherein:
  CDR1, CDR2, and CDR3 are:
    (i) CDR1 of SEQ ID NO: 10, CDR2 of SEQ ID NO: 11, and CDR3 of SEQ ID NO: 12; or
    (ii) CDR1 of SEQ ID NO: 18, CDR2 of SEQ ID NO: 19, and CDR3 of SEQ ID NO: 20;
  FR1 is the amino acid sequence of SEQ ID NO: 13;
  FR2 is the amino acid sequence of SEQ ID NO: 14;
  FR3 is the amino acid sequence of SEQ ID NO: 15; and
  FR3 is the amino acid sequence of SEQ ID NO: 16;
wherein FR1 and FR4 are at the N-terminus and C-terminus of the sdAb domain, respectively.

In yet another embodiment, the sdAb domain has the structure of FR1-CDR1-FR2-CDR2-FR3-CDR3-FR4, wherein:
  CDR1, CDR2, and CDR3 are:
    (i) CDR1 of SEQ ID NO: 10, CDR2 of SEQ ID NO: 11, and CDR3 of SEQ ID NO: 12; or
    (ii) CDR1 of SEQ ID NO: 18, CDR2 of SEQ ID NO: 19, and CDR3 of SEQ ID NO: 20;
  FR1 is the amino acid sequence of SEQ ID NO: 21;
  FR2 is the amino acid sequence of SEQ ID NO: 22;
  FR3 is the amino acid sequence of SEQ ID NO: 15; and
  FR3 is the amino acid sequence of SEQ ID NO: 23;
wherein FR1 and FR4 are at the N-terminus and C-terminus of the sdAb domain, respectively.

In one embodiment, the sdAb domain comprises the amino acid sequence of SEQ ID NO: 17 or 24. In another embodiment, the sdAb domain comprises the amino acid sequence of SEQ ID NO: 17. In yet another embodiment, the sdAb domain comprises the amino acid sequence of SEQ ID NO: 24.

In certain embodiments, the sdAb domain comprises an amino acid sequence of a human anti-HSA antibody. In certain embodiments, the sdAb domain has tan amino acid sequence of a humanized anti-HSA antibody.

In one embodiment, provided herein is a fusion protein comprising an interleukin-22 domain and an sdAb domain, wherein the interleukin-22 domain and sdAb domain are at the N-terminus and C-terminus of the fusion protein, respectively; or wherein the interleukin-22 domain and sdAb domain are at the C-terminus and N-terminus of the fusion protein, respectively.

In one embodiment, the fusion protein provided herein comprises an interleukin-22 domain, an sdAb domain, and optionally a peptide linker; wherein the C-terminus of the interleukin-22 domain is connected to the N-terminus of the sdAb domain directly or via the peptide linker.

In another embodiment, the fusion protein provided herein comprises an interleukin-22 domain, an sdAb domain, and optionally a peptide linker; wherein the C-terminus of the sdAb domain is connected to the N-terminus of the interleukin-22 domain directly or via the peptide linker.

In another embodiment, provided herein is a fusion protein comprising an interleukin-22 domain, a peptide domain, and an sdAb domain, wherein the peptide domain is a second interleukin-22 domain, a GLP-2 domain, or an IGF-1 domain.

In one embodiment, the fusion protein provided herein comprises an interleukin-22 domain, a peptide domain, and an sdAb domain; wherein the interleukin-22 domain is at the N-terminus of the fusion protein.

In another embodiment, the fusion protein provided herein comprises an interleukin-22 domain, a peptide domain, an sdAb domain, and optionally first and second peptide linkers; wherein the C-terminus of the interleukin-22 domain is connected to the N-terminus of the peptide domain directly or via the first peptide linker, and the C-terminus of the peptide domain is connected to the N-terminus of the sdAb domain directly or via the second peptide linker.

In yet another embodiment, the fusion protein provided herein comprises an interleukin-22 domain, a peptide domain, an sdAb domain, and optionally first and second peptide linkers; wherein the C-terminus of the interleukin-22 domain is connected to the N-terminus of the sdAb domain directly or via the first peptide linker, and the C-terminus of the sdAb domain is connected to the N-terminus of the peptide domain directly or via the second peptide linker.

In yet another embodiment, the fusion protein provided herein comprises an interleukin-22 domain, a peptide domain, and an sdAb domain; wherein the peptide domain is at the N-terminus of the fusion protein.

In yet another embodiment, the fusion protein provided herein comprises an interleukin-22 domain, a peptide domain, an sdAb domain, and optionally first and second peptide linkers; wherein the C-terminus of the peptide domain is connected to the N-terminus of the interleukin-22 domain directly or via the first peptide linker, and the C-terminus of the interleukin-22 domain is connected to the N-terminus of the sdAb domain directly or via the second peptide linker.

In yet another embodiment, the fusion protein provided herein comprises an interleukin-22 domain, a peptide domain, an sdAb domain, and optionally first and second peptide linkers; wherein the C-terminus of the peptide domain is connected to the N-terminus of the sdAb domain directly or via the first peptide linker, and the C-terminus of the sdAb domain is connected to the N-terminus of the interleukin-22 domain directly or via the second peptide linker.

In yet another embodiment, the fusion protein provided herein comprises an interleukin-22 domain, a peptide domain, and an sdAb domain; wherein the sdAb domain is at the N-terminus of the fusion protein.

In yet another embodiment, the fusion protein provided herein comprises an interleukin-22 domain, a peptide domain, an sdAb domain, and optionally first and second peptide linkers; wherein the C-terminus of the sdAb domain is connected to the N-terminus of the interleukin-22 domain directly or via the first peptide linker, and the C-terminus of the interleukin-22 domain is connected to the N-terminus of the peptide domain directly or via the second peptide linker.

In still another embodiment, the fusion protein provided herein comprises an interleukin-22 domain, a peptide domain, an sdAb domain, and optionally first and second peptide linkers; wherein the C-terminus of the sdAb domain is connected to the N-terminus of the peptide domain directly or via the first peptide linker, and the C-terminus of the peptide domain is connected to the N-terminus of the interleukin-22 domain directly or via the second peptide linker.

In yet another embodiment, provided herein is a fusion protein comprising first and second interleukin-22 domains, and an sdAb domain.

In one embodiment, the fusion protein provided herein comprises first and second interleukin-22 domains, and an sdAb domain; wherein one of the interleukin-22 domains is at the N-terminus of the fusion protein.

In another embodiment, the fusion protein provided herein comprises first and second interleukin-22 domains, an sdAb domain, and optionally first and second peptide linkers; wherein the C-terminus of the first interleukin-22 domain is connected to the N-terminus of the second interleukin-22 domain directly or via the first peptide linker, and the C-terminus of the second interleukin-22 domain is connected to the N-terminus of the sdAb domain directly or via the second peptide linker.

In another embodiment, the fusion protein provided herein comprises first and second interleukin-22 domains, an sdAb domain, and optionally first and second peptide linkers; wherein the C-terminus of the first interleukin-22 domain is connected to the N-terminus of the sdAb domain directly or via the first peptide linker, and the C-terminus of the sdAb domain is connected to the N-terminus of the second interleukin-22 domain directly or via the second peptide linker.

In yet another embodiment, the fusion protein provided herein comprises first and second interleukin-22 domains, and an sdAb domain; wherein the sdAb domain is at the N-terminus of the fusion protein.

In still another embodiment, the fusion protein provided herein comprises first and second interleukin-22 domains, an sdAb domain, and optionally first and second peptide linkers; wherein the C-terminus of the sdAb domain is connected to the N-terminus of the first interleukin-22 domain directly or via the first peptide linker, and the C-terminus of the first interleukin-22 domain is connected to the N-terminus of the second interleukin-22 domain directly or via the second peptide linker.

In yet another embodiment, provided herein is a fusion protein comprising an interleukin-22 domain, a GLP-2 domain, and an sdAb domain.

In one embodiment, the fusion protein provided herein comprises an interleukin-22 domain, a GLP-2 domain, and an sdAb domain; wherein the interleukin-22 domain is at the N-terminus of the fusion protein.

In another embodiment, the fusion protein provided herein comprises an interleukin-22 domain, a GLP-2 domain, an sdAb domain, and optionally first and second peptide linkers; wherein the C-terminus of the interleukin-22 domain is connected to the N-terminus of the GLP-2 domain directly or via the first peptide linker, and the C-terminus of the GLP-2 domain is connected to the N-terminus of the sdAb domain directly or via the second peptide linker.

In yet another embodiment, the fusion protein provided herein comprises an interleukin-22 domain, a GLP-2 domain, an sdAb domain, and optionally first and second peptide linkers; wherein the C-terminus of the interleukin-22 domain is connected to the N-terminus of the sdAb domain directly or via the first peptide linker, and the C-terminus of the sdAb domain is connected to the N-terminus of the GLP-2 domain directly or via the second peptide linker.

In one embodiment, the fusion protein provided herein comprises an interleukin-22 domain, a GLP-2 domain, and an sdAb domain; wherein the GLP-2 domain is at the N-terminus of the fusion protein.

In yet another embodiment, the fusion protein provided herein comprises an interleukin-22 domain, a GLP-2 domain, an sdAb domain, and optionally first and second peptide linkers; wherein the C-terminus of the GLP-2 domain is connected to the N-terminus of the interleukin-22 domain directly or via the first peptide linker, and the C-terminus of the interleukin-22 domain is connected to the N-terminus of the sdAb domain directly or via the second peptide linker.

In yet another embodiment, the fusion protein provided herein comprises an interleukin-22 domain, a GLP-2 domain, an sdAb domain, and optionally first and second peptide linkers; wherein the C-terminus of the GLP-2 domain is connected to the N-terminus of the sdAb domain directly or via the first peptide linker, and the C-terminus of the sdAb domain is connected to the N-terminus of the interleukin-22 domain directly or via the second peptide linker.

In one embodiment, the fusion protein provided herein comprises an interleukin-22 domain, a GLP-2 domain, and an sdAb domain; wherein the sdAb domain is at the N-terminus of the fusion protein.

In yet another embodiment, the fusion protein provided herein comprises an interleukin-22 domain, a GLP-2 domain, an sdAb domain, and optionally first and second peptide linkers; wherein the C-terminus of the sdAb domain is connected to the N-terminus of the interleukin-22 domain directly or via the first peptide linker, and the C-terminus of the interleukin-22 domain is connected to the N-terminus of the GLP-2 domain directly or via the second peptide linker.

In still another embodiment, the fusion protein provided herein comprises an interleukin-22 domain, a GLP-2 domain, an sdAb domain, and optionally first and second peptide linkers; wherein the C-terminus of the sdAb domain is connected to the N-terminus of the GLP-2 domain directly or via the first peptide linker, and the C-terminus of the GLP-2 domain is connected to the N-terminus of the interleukin-22 domain directly or via the second peptide linker.

In yet another embodiment, provided herein is a fusion protein comprising an interleukin-22 domain, an IGF-1 domain, and an sdAb domain.

In one embodiment, the fusion protein provided herein comprises an interleukin-22 domain, an IGF-1 domain, and an sdAb domain; wherein the interleukin-22 domain is at the N-terminus of the fusion protein.

In another embodiment, the fusion protein provided herein comprises an interleukin-22 domain, an IGF-1 domain, an sdAb domain, and optionally first and second peptide linkers; wherein the C-terminus of the interleukin-22 domain is connected to the N-terminus of the IGF-1 domain directly or via the first peptide linker, and the C-terminus of the IGF-1 domain is connected to the N-terminus of the sdAb domain directly or via the second peptide linker.

In yet another embodiment, the fusion protein provided herein comprises an interleukin-22 domain, an IGF-1 domain, an sdAb domain, and optionally first and second peptide linkers; wherein the C-terminus of the interleukin-22 domain is connected to the N-terminus of the sdAb domain directly or via the first peptide linker, and the C-terminus of the sdAb domain is connected to the N-terminus of the IGF-1 domain directly or via the second peptide linker.

In yet another embodiment, the fusion protein provided herein comprises an interleukin-22 domain, an IGF-1 domain, and an sdAb domain; wherein the IGF-1 domain is at the N-terminus of the fusion protein.

In yet another embodiment, the fusion protein provided herein comprises an interleukin-22 domain, an IGF-1 domain, an sdAb domain, and optionally first and second peptide linkers; wherein the C-terminus of the IGF-1 domain is connected to the N-terminus of the interleukin-22 domain directly or via the first peptide linker, and the C-terminus of the interleukin-22 domain is connected to the N-terminus of the sdAb domain directly or via the second peptide linker.

In yet another embodiment, the fusion protein provided herein comprises an interleukin-22 domain, an IGF-1 domain, an sdAb domain, and optionally first and second peptide linkers; wherein the C-terminus of the IGF-1 domain is connected to the N-terminus of the sdAb domain directly or via the first peptide linker, and the C-terminus of the sdAb domain is connected to the N-terminus of the interleukin-22 domain directly or via the second peptide linker.

In yet another embodiment, the fusion protein provided herein comprises an interleukin-22 domain, an IGF-1 domain, and an sdAb domain; wherein the sdAb domain is at the N-terminus of the fusion protein.

In yet another embodiment, the fusion protein provided herein comprises an interleukin-22 domain, an IGF-1 domain, an sdAb domain, and optionally first and second peptide linkers; wherein the C-terminus of the sdAb domain is connected to the N-terminus of the interleukin-22 domain directly or via the first peptide linker, and the C-terminus of the interleukin-22 domain is connected to the N-terminus of the IGF-1 domain directly or via the second peptide linker.

In still another embodiment, the fusion protein provided herein comprises an interleukin-22 domain, an IGF-1 domain, an sdAb domain, and optionally first and second peptide linkers; wherein the C-terminus of the sdAb domain is connected to the N-terminus of the IGF-1 domain directly or via the first peptide linker, and the C-terminus of the IGF-1 domain is connected to the N-terminus of the interleukin-22 domain directly or via the second peptide linker.

In still another embodiment, provided herein is a fusion protein comprising first and second interleukin-22 domains, a GLP-2 domain or an IGF-1 domain, and an sdAb domain.

In one embodiment, the fusion protein provided herein comprises first and second interleukin-22 domains, a GLP-2 domain, and an sdAb domain.

In another embodiment, the fusion protein provided herein comprises first and second interleukin-22 domains, a GLP-2 domain, and an sdAb domain; wherein one of the interleukin-22 domains is at the N-terminus of the fusion protein.

In yet another embodiment, the fusion protein provided herein comprises first and second interleukin-22 domains, a GLP-2 domain, and an sdAb domain; wherein the GLP-2 domain is at the N-terminus of the fusion protein.

In yet another embodiment, the fusion protein provided herein comprises first and second interleukin-22 domains, a GLP-2 domain, and an sdAb domain; wherein the sdAb domain is at the N-terminus of the fusion protein.

In yet another embodiment, the fusion protein provided herein comprises first and second interleukin-22 domains, a GLP-2 domain, and an sdAb domain; wherein one of the interleukin-22 domains is at the C-terminus of the fusion protein.

In yet another embodiment, the fusion protein provided herein comprises first and second interleukin-22 domains, a GLP-2 domain, and an sdAb domain; wherein the GLP-2 domain is at the C-terminus of the fusion protein.

In still another embodiment, the fusion protein provided herein comprises first and second interleukin-22 domains, a GLP-2 domain, and an sdAb domain; wherein the sdAb domain is at the C-terminus of the fusion protein.

In one embodiment, the fusion protein provided herein comprises first and second interleukin-22 domains, an IGF-1 domain, and an sdAb domain.

In another embodiment, the fusion protein provided herein comprises first and second interleukin-22 domains, an IGF-1 domain, and an sdAb domain; wherein one of the interleukin-22 domains is at the N-terminus of the fusion protein.

In yet another embodiment, the fusion protein provided herein comprises first and second interleukin-22 domains, an IGF-1 domain, and an sdAb domain; wherein the IGF-1 domain is at the N-terminus of the fusion protein.

In yet another embodiment, the fusion protein provided herein comprises first and second interleukin-22 domains, an IGF-1 domain, and an sdAb domain; wherein the sdAb domain is at the N-terminus of the fusion protein.

In yet another embodiment, the fusion protein provided herein comprises first and second interleukin-22 domains, an IGF-1 domain, and an sdAb domain; wherein one of the interleukin-22 domains is at the C-terminus of the fusion protein.

In yet another embodiment, the fusion protein provided herein comprises first and second interleukin-22 domains, an IGF-1 domain, and an sdAb domain; wherein the IGF-1 domain is at the C-terminus of the fusion protein.

In still another embodiment, the fusion protein provided herein comprises first and second interleukin-22 domains, an IGF-1 domain, and an sdAb domain; wherein the sdAb domain is at the C-terminus of the fusion protein.

In one embodiment, in Formula (II), $D^1$ is an interleukin-22 domain and $D^2$ is an sdAb domain. In another embodiment, in Formula (II), $D^1$ is an sdAb domain and $D^2$ is an interleukin-22 domain.

In one embodiment, in Formula (III), $D^1$ is an interleukin-22 domain, $D^2$ is an sdAb domain, and $D^N$ is an interleukin-22 domain. In another embodiment, in Formula (III), $D^1$ is an interleukin-22 domain, $D^2$ is an sdAb domain, and $D^N$ is a GLP-2 domain. In yet another embodiment, in Formula (III), $D^1$ is an interleukin-22 domain, $D^2$ is an sdAb domain, and $D^N$ is an IGF-1 domain.

In one embodiment, in Formula (III), $D^1$ is an sdAb domain, $D^2$ is an interleukin-22 domain, and $D^N$ is an interleukin-22 domain. In another embodiment, in Formula (III), $D^1$ is an sdAb domain, $D^2$ is an interleukin-22 domain, and $D^N$ is a GLP-2 domain. In yet another embodiment, in Formula (III), $D^1$ is an sdAb domain, $D^2$ is an interleukin-22 domain, and $D^N$ is an IGF-1 domain.

In one embodiment, in Formula (IV), $D^1$ is an interleukin-22 domain, $D^2$ is an sdAb domain, and $D^C$ is a GLP-2 domain. In another embodiment, in Formula (IV), $D^1$ is an interleukin-22 domain, $D^2$ is an sdAb domain, and $D^C$ is an IGF-1 domain.

In one embodiment, in Formula (IV), $D^1$ is an sdAb domain, $D^2$ is an interleukin-22 domain, and $D^C$ is a GLP-2 domain. In another embodiment, in Formula (IV), $D^1$ is an sdAb domain, $D^2$ is an interleukin-22 domain, and $D^C$ is an IGF-1 domain.

In one embodiment, in Formula (V), $D^1$ is an interleukin-22 domain, $D^2$ is an sdAb domain, $D^C$ is an interleukin-22 domain, and $D^N$ is a GLP-2 domain. In another embodiment, in Formula (V), $D^1$ is an interleukin-22 domain, $D^2$ is an sdAb domain, $D^C$ is an interleukin-22 domain, and $D^N$ is an IGF-1 domain. In yet another embodiment, in Formula (V), $D^1$ is an interleukin-22 domain, $D^2$ is an sdAb domain, $D^C$ is a GLP-2 domain, and $D^N$ is an interleukin-22 domain. In still another embodiment, in Formula (V), $D^1$ is an interleukin-22 domain, $D^2$ is an sdAb domain, $D^C$ is an IGF-1 domain, and $D^N$ is an interleukin-22 domain.

In one embodiment, in Formula (V), $D^1$ is an sdAb domain, $D^2$ is an interleukin-22 domain, $D^C$ is an interleukin-22 domain, and $D^N$ is a GLP-2 domain. In another embodiment, in Formula (V), $D^1$ is an sdAb domain, $D^2$ is an interleukin-22 domain, $D^C$ is an interleukin-22 domain, and $D^N$ is an IGF-1 domain. In yet another embodiment, in Formula (V), $D^1$ is an sdAb domain, $D^2$ is an interleukin-22 domain, $D^C$ is a GLP-2 domain, and $D^N$ is an interleukin-22 domain. In still another embodiment, in Formula (V), $D^1$ is an sdAb domain, $D^2$ is an interleukin-22 domain, $D^C$ is an IGF-1 domain, and $D^N$ is an interleukin-22 domain.

In yet another embodiment, the albumin binding domain has an amino acid sequence of a $V_HH$ single domain antibody ("$V_HH$ antibody") that binds to an albumin. In certain embodiments, the albumin binding domain has an amino acid sequence of a $V_HH$ antibody that binds to an HSA.

In certain embodiments, the $V_HH$ antibody binds to an HSA with a $K_d$ ranging from about 10 pM to about 1,000 nM. In certain embodiments, the $V_HH$ antibody binds to an HSA with a $K_d$ ranging from about 1 nM to about 500 nM. In certain embodiments, the $V_HH$ antibody binds to an HSA with a $K_d$ ranging from about 1 nM to about 200 nM. In certain embodiments, the $V_HH$ antibody binds to an HSA with a $K_d$ ranging from about 1 nM to about 100 nM.

In one embodiment, the albumin binding domain is a domain of a $V_HH$ antibody ("$V_HH$ antibody domain"). In another embodiment, the $V_HH$ antibody domain comprises (i) a heavy chain CDR1 of SEQ ID NO: 10, a heavy chain CDR2 of SEQ ID NO: 11, and a heavy chain CDR3 of SEQ ID NO: 12; or (ii) a heavy chain CDR1 of SEQ ID NO: 18, a heavy chain CDR2 of SEQ ID NO: 19, and a heavy chain CDR3 of SEQ ID NO: 20. In another embodiment, the $V_HH$ antibody domain comprises a heavy chain CDR1 of SEQ ID NO: 10, a heavy chain CDR2 of SEQ ID NO: 11, and a heavy chain CDR3 of SEQ ID NO: 12. In yet another embodiment, the $V_HH$ antibody domain comprises a heavy chain CDR1 of SEQ ID NO: 18, a heavy chain CDR2 of SEQ ID NO: 19, and a heavy chain CDR3 of SEQ ID NO: 20.

In one embodiment, the $V_HH$ antibody domain has the structure of FR1-CDR1-FR2-CDR2-FR3-CDR3-FR4, wherein:
  CDR1, CDR2, and CDR3 are:
    (i) CDR1 of SEQ ID NO: 10, CDR2 of SEQ ID NO: 11, and CDR3 of SEQ ID NO: 12; or
    (ii) CDR1 of SEQ ID NO: 18, CDR2 of SEQ ID NO: 19, and CDR3 of SEQ ID NO: 20;
  FR1 is the amino acid sequence of SEQ ID NO: 13 or 21;
  FR2 is the amino acid sequence of SEQ ID NO: 14 or 22;
  FR3 is the amino acid sequence of SEQ ID NO: 15; and
  FR4 is the amino acid sequence of SEQ ID NO: 16 or 23;
  wherein FR1 and FR4 are at the N-terminus and C-terminus of the $V_HH$ antibody domain, respectively.

In another embodiment, the $V_HH$ antibody domain has the structure of FR1-CDR1-FR2-CDR2-FR3-CDR3-FR4, wherein:

CDR1, CDR2, and CDR3 are:
(i) CDR1 of SEQ ID NO: 10, CDR2 of SEQ ID NO: 11, and CDR3 of SEQ ID NO: 12; or
(ii) CDR1 of SEQ ID NO: 18, CDR2 of SEQ ID NO: 19, and CDR3 of SEQ ID NO: 20;
FR1 is the amino acid sequence of SEQ ID NO: 13;
FR2 is the amino acid sequence of SEQ ID NO: 14;
FR3 is the amino acid sequence of SEQ ID NO: 15; and
FR4 is the amino acid sequence of SEQ ID NO: 16;
wherein FR1 and FR4 are at the N-terminus and C-terminus of the $V_HH$ antibody domain, respectively.

In yet another embodiment, the $V_HH$ antibody domain has the structure of FR1-CDR1-FR2-CDR2-FR3-CDR3-FR4, wherein:
CDR1, CDR2, and CDR3 are:
(i) CDR1 of SEQ ID NO: 10, CDR2 of SEQ ID NO: 11, and CDR3 of SEQ ID NO: 12; or
(ii) CDR1 of SEQ ID NO: 18, CDR2 of SEQ ID NO: 19, and CDR3 of SEQ ID NO: 20;
FR1 is the amino acid sequence of SEQ ID NO: 21;
FR2 is the amino acid sequence of SEQ ID NO: 22;
FR3 is the amino acid sequence of SEQ ID NO: 15; and
FR4 is the amino acid sequence of SEQ ID NO: 23;
wherein FR1 and FR4 are at the N-terminus and C-terminus of the $V_HH$ antibody domain, respectively.

In one embodiment, the $V_HH$ antibody domain comprises the amino acid sequence of SEQ ID NO: 17 or 24. In another embodiment, the $V_HH$ antibody domain comprises the amino acid sequence of SEQ ID NO: 17. In yet another embodiment, the $V_HH$ antibody domain comprises the amino acid sequence of SEQ ID NO: 24.

In certain embodiments, the $V_HH$ antibody domain has an amino acid sequence of a human anti-HSA antibody. In certain embodiments, the $V_HH$ antibody domain has an amino acid sequence of a humanized anti-HSA antibody.

In one embodiment, provided herein is a fusion protein comprising an interleukin-22 domain and a $V_HH$ antibody domain, wherein the interleukin-22 domain and $V_HH$ antibody domain are at the N-terminus and C-terminus of the fusion protein, respectively; or wherein the interleukin-22 domain and $V_HH$ antibody domain are at the C-terminus and N-terminus of the fusion protein, respectively.

In one embodiment, the fusion protein provided herein comprises an interleukin-22 domain, a $V_HH$ antibody domain, and optionally a peptide linker; wherein the C-terminus of the interleukin-22 domain is connected to the N-terminus of the $V_HH$ antibody domain directly or via the peptide linker.

In another embodiment, the fusion protein provided herein comprises an interleukin-22 domain, a $V_HH$ antibody domain, and optionally a peptide linker; wherein the C-terminus of the $V_HH$ antibody domain is connected to the N-terminus of the interleukin-22 domain directly or via the peptide linker.

In another embodiment, provided herein is a fusion protein comprising an interleukin-22 domain, a peptide domain, and a $V_HH$ antibody domain, wherein the peptide domain is a second interleukin-22 domain, a GLP-2 domain, or an IGF-1 domain.

In one embodiment, the fusion protein provided herein comprises an interleukin-22 domain, a peptide domain, and a $V_HH$ antibody domain; wherein the interleukin-22 domain is at the N-terminus of the fusion protein.

In another embodiment, the fusion protein provided herein comprises an interleukin-22 domain, a peptide domain, a $V_HH$ antibody domain, and optionally first and second peptide linkers; wherein the C-terminus of the interleukin-22 domain is connected to the N-terminus of the peptide domain directly or via the first peptide linker, and the C-terminus of the peptide domain is connected to the N-terminus of the $V_HH$ antibody domain directly or via the second peptide linker.

In yet another embodiment, the fusion protein provided herein comprises an interleukin-22 domain, a peptide domain, a $V_HH$ antibody domain, and optionally first and second peptide linkers; wherein the C-terminus of the interleukin-22 domain is connected to the N-terminus of the $V_HH$ antibody domain directly or via the first peptide linker, and the C-terminus of the $V_HH$ antibody domain is connected to the N-terminus of the peptide domain directly or via the second peptide linker.

In yet another embodiment, the fusion protein provided herein comprises an interleukin-22 domain, a peptide domain, and a $V_HH$ antibody domain; wherein the peptide domain is at the N-terminus of the fusion protein.

In yet another embodiment, the fusion protein provided herein comprises an interleukin-22 domain, a peptide domain, a $V_HH$ antibody domain, and optionally first and second peptide linkers; wherein the C-terminus of the peptide domain is connected to the N-terminus of the interleukin-22 domain directly or via the first peptide linker, and the C-terminus of the interleukin-22 domain is connected to the N-terminus of the $V_HH$ antibody domain directly or via the second peptide linker.

In yet another embodiment, the fusion protein provided herein comprises an interleukin-22 domain, a peptide domain, a $V_HH$ antibody domain, and optionally first and second peptide linkers; wherein the C-terminus of the peptide domain is connected to the N-terminus of the $V_HH$ antibody domain directly or via the first peptide linker, and the C-terminus of the $V_HH$ antibody domain is connected to the N-terminus of the interleukin-22 domain directly or via the second peptide linker.

In yet another embodiment, the fusion protein provided herein comprises an interleukin-22 domain, a peptide domain, and a $V_HH$ antibody domain; wherein the $V_HH$ antibody domain is at the N-terminus of the fusion protein.

In yet another embodiment, the fusion protein provided herein comprises an interleukin-22 domain, a peptide domain, a $V_HH$ antibody domain, and optionally first and second peptide linkers; wherein the C-terminus of the $V_HH$ antibody domain is connected to the N-terminus of the interleukin-22 domain directly or via the first peptide linker, and the C-terminus of the interleukin-22 domain is connected to the N-terminus of the peptide domain directly or via the second peptide linker.

In still another embodiment, the fusion protein provided herein comprises an interleukin-22 domain, a peptide domain, a $V_HH$ antibody domain, and optionally first and second peptide linkers; wherein the C-terminus of the $V_HH$ antibody domain is connected to the N-terminus of the peptide domain directly or via the first peptide linker, and the C-terminus of the peptide domain is connected to the N-terminus of the interleukin-22 domain directly or via the second peptide linker.

In yet another embodiment, provided herein is a fusion protein comprising first and second interleukin-22 domains, and a $V_HH$ antibody domain.

In one embodiment, the fusion protein provided herein comprises first and second interleukin-22 domains, and a $V_HH$ antibody domain; wherein one of the interleukin-22 domains is at the N-terminus of the fusion protein.

In another embodiment, the fusion protein provided herein comprises first and second interleukin-22 domains, a $V_HH$ antibody domain, and optionally first and second peptide linkers; wherein the C-terminus of the first interleukin-22 domain is connected to the N-terminus of the second interleukin-22 domain directly or via the first peptide linker, and the C-terminus of the second interleukin-22 domain is connected to the N-terminus of the $V_HH$ antibody domain directly or via the second peptide linker.

In another embodiment, the fusion protein provided herein comprises first and second interleukin-22 domains, a $V_HH$ antibody domain, and optionally first and second peptide linkers; wherein the C-terminus of the first interleukin-22 domain is connected to the N-terminus of the $V_HH$ antibody domain directly or via the first peptide linker, and the C-terminus of the $V_HH$ antibody domain is connected to the N-terminus of the second interleukin-22 domain directly or via the second peptide linker.

In yet another embodiment, the fusion protein provided herein comprises first and second interleukin-22 domains, and a $V_HH$ antibody domain; wherein the $V_HH$ antibody domain is at the N-terminus of the fusion protein.

In still another embodiment, the fusion protein provided herein comprises first and second interleukin-22 domains, a $V_HH$ antibody domain, and optionally first and second peptide linkers; wherein the C-terminus of the $V_HH$ antibody domain is connected to the N-terminus of the first interleukin-22 domain directly or via the first peptide linker, and the C-terminus of the first interleukin-22 domain is connected to the N-terminus of the second interleukin-22 domain directly or via the second peptide linker.

In yet another embodiment, provided herein is a fusion protein comprising an interleukin-22 domain, a GLP-2 domain, and a $V_HH$ antibody domain.

In one embodiment, the fusion protein provided herein comprises an interleukin-22 domain, a GLP-2 domain, and a $V_HH$ antibody domain; wherein the interleukin-22 domain is at the N-terminus of the fusion protein.

In another embodiment, the fusion protein provided herein comprises an interleukin-22 domain, a GLP-2 domain, a $V_HH$ antibody domain, and optionally first and second peptide linkers; wherein the C-terminus of the interleukin-22 domain is connected to the N-terminus of the GLP-2 domain directly or via the first peptide linker, and the C-terminus of the GLP-2 domain is connected to the N-terminus of the $V_HH$ antibody domain directly or via the second peptide linker.

In yet another embodiment, the fusion protein provided herein comprises an interleukin-22 domain, a GLP-2 domain, a $V_HH$ antibody domain, and optionally first and second peptide linkers; wherein the C-terminus of the interleukin-22 domain is connected to the N-terminus of the $V_HH$ antibody domain directly or via the first peptide linker, and the C-terminus of the $V_HH$ antibody domain is connected to the N-terminus of the GLP-2 domain directly or via the second peptide linker.

In one embodiment, the fusion protein provided herein comprises an interleukin-22 domain, a GLP-2 domain, and a $V_HH$ antibody domain; wherein the GLP-2 domain is at the N-terminus of the fusion protein.

In yet another embodiment, the fusion protein provided herein comprises an interleukin-22 domain, a GLP-2 domain, a $V_HH$ antibody domain, and optionally first and second peptide linkers; wherein the C-terminus of the GLP-2 domain is connected to the N-terminus of the interleukin-22 domain directly or via the first peptide linker, and the C-terminus of the interleukin-22 domain is connected to the N-terminus of the $V_HH$ antibody domain directly or via the second peptide linker.

In yet another embodiment, the fusion protein provided herein comprises an interleukin-22 domain, a GLP-2 domain, a $V_HH$ antibody domain, and optionally first and second peptide linkers; wherein the C-terminus of the GLP-2 domain is connected to the N-terminus of the $V_HH$ antibody domain directly or via the first peptide linker, and the C-terminus of the $V_HH$ antibody domain is connected to the N-terminus of the interleukin-22 domain directly or via the second peptide linker.

In one embodiment, the fusion protein provided herein comprises an interleukin-22 domain, a GLP-2 domain, and a $V_HH$ antibody domain; wherein the $V_HH$ antibody domain is at the N-terminus of the fusion protein.

In yet another embodiment, the fusion protein provided herein comprises an interleukin-22 domain, a GLP-2 domain, a $V_HH$ antibody domain, and optionally first and second peptide linkers; wherein the C-terminus of the $V_HH$ antibody domain is connected to the N-terminus of the interleukin-22 domain directly or via the first peptide linker, and the C-terminus of the interleukin-22 domain is connected to the N-terminus of the GLP-2 domain directly or via the second peptide linker.

In still another embodiment, the fusion protein provided herein comprises an interleukin-22 domain, a GLP-2 domain, and a $V_HH$ antibody domain; wherein the C-terminus of the $V_HH$ antibody domain is connected to the N-terminus of the GLP-2 domain directly or via the first peptide linker, and the C-terminus of the GLP-2 domain is connected to the N-terminus of the interleukin-22 domain directly or via the second peptide linker.

In yet another embodiment, provided herein is a fusion protein comprising an interleukin-22 domain, an IGF-1 domain, and a $V_HH$ antibody domain.

In one embodiment, the fusion protein provided herein comprises an interleukin-22 domain, an IGF-1 domain, and a $V_HH$ antibody domain; wherein the interleukin-22 domain is at the N-terminus of the fusion protein.

In another embodiment, the fusion protein provided herein comprises an interleukin-22 domain, an IGF-1 domain, a $V_HH$ antibody domain, and optionally first and second peptide linkers; wherein the C-terminus of the interleukin-22 domain is connected to the N-terminus of the IGF-1 domain directly or via the first peptide linker, and the C-terminus of the IGF-1 domain is connected to the N-terminus of the $V_HH$ antibody domain directly or via the second peptide linker.

In yet another embodiment, the fusion protein provided herein comprises an interleukin-22 domain, an IGF-1 domain, a $V_HH$ antibody domain, and optionally first and second peptide linkers; wherein the C-terminus of the interleukin-22 domain is connected to the N-terminus of the $V_HH$ antibody domain directly or via the first peptide linker, and the C-terminus of the $V_HH$ antibody domain is connected to the N-terminus of the IGF-1 domain directly or via the second peptide linker.

In yet another embodiment, the fusion protein provided herein comprises an interleukin-22 domain, an IGF-1 domain, and a $V_HH$ antibody domain; wherein the IGF-1 domain is at the N-terminus of the fusion protein.

In yet another embodiment, the fusion protein provided herein comprises an interleukin-22 domain, an IGF-1 domain, a $V_HH$ antibody domain, and optionally first and second peptide linkers; wherein the C-terminus of the IGF-1 domain is connected to the N-terminus of the interleukin-22 domain directly or via the first peptide linker, and the C-terminus of the interleukin-22 domain is connected to the N-terminus of the $V_HH$ antibody domain directly or via the second peptide linker.

In yet another embodiment, the fusion protein provided herein comprises an interleukin-22 domain, an IGF-1 domain, a $V_HH$ antibody domain, and optionally first and second peptide linkers; wherein the C-terminus of the IGF-1 domain is connected to the N-terminus of the $V_HH$ antibody domain directly or via the first peptide linker, and the C-terminus of the $V_HH$ antibody domain is connected to the N-terminus of the interleukin-22 domain directly or via the second peptide linker.

In yet another embodiment, the fusion protein provided herein comprises an interleukin-22 domain, an IGF-1 domain, and a $V_HH$ antibody domain; wherein the $V_HH$ antibody domain is at the N-terminus of the fusion protein.

In yet another embodiment, the fusion protein provided herein comprises an interleukin-22 domain, an IGF-1 domain, a $V_HH$ antibody domain, and optionally first and second peptide linkers; wherein the C-terminus of the $V_HH$ antibody domain is connected to the N-terminus of the interleukin-22 domain directly or via the first peptide linker, and the C-terminus of the interleukin-22 domain is connected to the N-terminus of the IGF-1 domain directly or via the second peptide linker.

In still another embodiment, the fusion protein provided herein comprises an interleukin-22 domain, an IGF-1 domain, a $V_HH$ antibody domain, and optionally first and second peptide linkers; wherein the C-terminus of the $V_HH$ antibody domain is connected to the N-terminus of the IGF-1 domain directly or via the first peptide linker, and the C-terminus of the IGF-1 domain is connected to the N-terminus of the interleukin-22 domain directly or via the second peptide linker.

In still another embodiment, provided herein is a fusion protein comprising first and second interleukin-22 domains, a GLP-2 domain or an IGF-1 domain, and a $V_HH$ antibody domain.

In one embodiment, the fusion protein provided herein comprises first and second interleukin-22 domains, a GLP-2 domain, and a $V_HH$ antibody domain.

In another embodiment, the fusion protein provided herein comprises first and second interleukin-22 domains, a GLP-2 domain, and a $V_HH$ antibody domain; wherein one of the interleukin-22 domains is at the N-terminus of the fusion protein.

In yet another embodiment, the fusion protein provided herein comprises first and second interleukin-22 domains, a GLP-2 domain, and a $V_HH$ antibody domain; wherein the GLP-2 domain is at the N-terminus of the fusion protein.

In yet another embodiment, the fusion protein provided herein comprises first and second interleukin-22 domains, a GLP-2 domain, and a $V_HH$ antibody domain; wherein the $V_HH$ antibody domain is at the N-terminus of the fusion protein.

In yet another embodiment, the fusion protein provided herein comprises first and second interleukin-22 domains, a GLP-2 domain, and a $V_HH$ antibody domain; wherein one of the interleukin-22 domains is at the C-terminus of the fusion protein.

In yet another embodiment, the fusion protein provided herein comprises first and second interleukin-22 domains, a GLP-2 domain, and a $V_HH$ antibody domain; wherein the GLP-2 domain is at the C-terminus of the fusion protein.

In still another embodiment, the fusion protein provided herein comprises first and second interleukin-22 domains, a GLP-2 domain, and a $V_HH$ antibody domain; wherein the $V_HH$ antibody domain is at the C-terminus of the fusion protein.

In one embodiment, the fusion protein provided herein comprises first and second interleukin-22 domains, an IGF-1 domain, and a $V_HH$ antibody domain.

In another embodiment, the fusion protein provided herein comprises first and second interleukin-22 domains, an IGF-1 domain, and a $V_HH$ antibody domain; wherein one of the interleukin-22 domains is at the N-terminus of the fusion protein.

In yet another embodiment, the fusion protein provided herein comprises first and second interleukin-22 domains, an IGF-1 domain, and a $V_HH$ antibody domain; wherein the IGF-1 domain is at the N-terminus of the fusion protein.

In yet another embodiment, the fusion protein provided herein comprises first and second interleukin-22 domains, an IGF-1 domain, and a $V_HH$ antibody domain; wherein the $V_HH$ antibody domain is at the N-terminus of the fusion protein.

In yet another embodiment, the fusion protein provided herein comprises first and second interleukin-22 domains, an IGF-1 domain, and a $V_HH$ antibody domain; wherein one of the interleukin-22 domains is at the C-terminus of the fusion protein.

In yet another embodiment, the fusion protein provided herein comprises first and second interleukin-22 domains, an IGF-1 domain, and a $V_HH$ antibody domain; wherein the IGF-1 domain is at the C-terminus of the fusion protein.

In still another embodiment, the fusion protein provided herein comprises first and second interleukin-22 domains, an IGF-1 domain, and a $V_HH$ antibody domain; wherein the $V_HH$ antibody domain is at the C-terminus of the fusion protein.

In one embodiment, in Formula (II), $D^1$ is an interleukin-22 domain and $D^2$ is a $V_HH$ antibody domain. In another embodiment, in Formula (II), $D^1$ is a $V_HH$ antibody domain and $D^2$ is an interleukin-22 domain.

In one embodiment, in Formula (III), $D^1$ is an interleukin-22 domain, $D^2$ is a $V_HH$ antibody domain, and $D^N$ is an interleukin-22 domain. In another embodiment, in Formula (III), $D^1$ is an interleukin-22 domain, $D^2$ is a $V_HH$ antibody domain, and $D^N$ is a GLP-2 domain. In yet another embodiment, in Formula (III), $D^1$ is an interleukin-22 domain, $D^2$ is a $V_HH$ antibody domain, and $D^N$ is an IGF-1 domain.

In one embodiment, in Formula (III), $D^1$ is a $V_HH$ antibody domain, $D^2$ is an interleukin-22 domain, and $D^N$ is an interleukin-22 domain. In another embodiment, in Formula (III), $D^1$ is a $V_HH$ antibody domain, $D^2$ is an interleukin-22 domain, and $D^N$ is a GLP-2 domain. In yet another embodiment, in Formula (III), $D^1$ is a $V_HH$ antibody domain, $D^2$ is an interleukin-22 domain, and $D^N$ is an IGF-1 domain.

In one embodiment, in Formula (IV), $D^1$ is an interleukin-22 domain, $D^2$ is a $V_HH$ antibody domain, and $D^C$ is a GLP-2 domain. In another embodiment, in Formula (IV), $D^1$ is an interleukin-22 domain, $D^2$ is a $V_HH$ antibody domain, and $D^C$ is an IGF-1 domain.

In one embodiment, in Formula (IV), $D^1$ is a $V_HH$ antibody domain, $D^2$ is an interleukin-22 domain, and $D^C$ is a GLP-2 domain. In another embodiment, in Formula (IV), $D^1$ is a $V_HH$ antibody domain, $D^2$ is an interleukin-22 domain, and $D^C$ is an IGF-1 domain.

In one embodiment, in Formula (V), $D^1$ is an interleukin-22 domain, $D^2$ is a $V_HH$ antibody domain, $D^C$ is an interleukin-22 domain, and $D^N$ is a GLP-2 domain. In another embodiment, in Formula (V), $D^1$ is an interleukin-22 domain, $D^2$ is a $V_HH$ antibody domain, $D^C$ is an interleukin-22 domain, and $D^N$ is an IGF-1 domain. In yet another embodiment, in Formula (V), $D^1$ is an interleukin-22 domain, $D^2$ is a $V_HH$ antibody domain, $D^C$ is a GLP-2 domain, and $D^N$ is an interleukin-22 domain. In still another embodiment, in Formula (V), $D^1$ is an interleukin-22 domain, $D^2$ is a $V_HH$ antibody domain, $D^C$ is an IGF-1 domain, and $D^N$ is an interleukin-22 domain.

In one embodiment, in Formula (V), $D^1$ is a $V_HH$ antibody domain, $D^2$ is an interleukin-22 domain, $D^C$ is an interleukin-22 domain, and $D^N$ is a GLP-2 domain. In another embodiment, in Formula (V), $D^1$ is a $V_HH$ antibody domain, $D^2$ is an interleukin-22 domain, $D^C$ is an interleukin-22 domain, and $D^N$ is an IGF-1 domain. In yet another embodiment, in Formula (V), $D^1$ is a $V_HH$ antibody domain, $D^2$ is an interleukin-22 domain, $D^C$ is a GLP-2 domain, and $D^N$ is an interleukin-22 domain. In still another embodiment, in Formula (V), $D^1$ is a $V_HH$ antibody domain, $D^2$ is an interleukin-22 domain, $D^C$ is an IGF-1 domain, and $D^N$ is an interleukin-22 domain.

In one embodiment, each peptide linker in the fusion protein provided herein independently comprises a peptide linker having an amino acid sequence of GSG or one of SEQ ID NOs: 25 to 56.

In one embodiment, each peptide linker in the fusion protein provided herein independently comprises a GSG linker having an amino acid sequence of GSG or SEQ ID NO: 25, 26, or 27. In another embodiment, each peptide linker in the fusion protein provided herein independently comprises a G3S linker having the amino acid sequence of SEQ ID NO: 28, 29, 30, or 31. In yet another embodiment, each peptide linker in the fusion protein provided herein independently comprises a G4S linker having the amino acid sequence of SEQ ID NO: 32, 33, 34, or 35. In yet another embodiment, each peptide linker in the fusion protein provided herein independently comprises an SGSG linker having the amino acid sequence of SEQ ID NO: 36, 37, 38, or 39. In yet another embodiment, each peptide linker in the fusion protein provided herein independently comprises an SG3S linker having the amino acid sequence of SEQ ID NO: 40, 41, 42, or 43. In yet another embodiment, each peptide linker in the fusion protein provided herein independently comprises an SG4S linker having the amino acid sequence of SEQ ID NO: 44, 45, 46, or 47. In yet another embodiment, each peptide linker in the fusion protein provided herein independently comprises an EAAAK linker having the amino acid sequence of SEQ ID NO: 48, 49, 50, or 51. In yet another embodiment, each peptide linker in the fusion protein provided herein independently comprises a PAPAP linker having the amino acid sequence of SEQ ID NO: 52, 53, 54, or 55. In still another embodiment, each peptide linker in the fusion protein provided herein independently comprises a VLVH linker having the amino acid sequence of SEQ ID NO: 56.

In one embodiment, the first peptide linker in the fusion protein provided herein independently comprises a peptide linker having an amino acid sequence of GSG or one of SEQ ID NOs: 25 to 56.

In one embodiment, the first peptide linker in the fusion protein provided herein independently comprises a GSG linker having an amino acid sequence of GSG or SEQ ID NO: 25, 26, or 27. In another embodiment, the first peptide linker in the fusion protein provided herein independently comprises a G3S linker having the amino acid sequence of SEQ ID NO: 28, 29, 30, or 31. In yet another embodiment, the first peptide linker in the fusion protein provided herein independently comprises a G4S linker having the amino acid sequence of SEQ ID NO: 32, 33, 34, or 35. In yet another embodiment, the first peptide linker in the fusion protein provided herein independently comprises an SGSG linker having the amino acid sequence of SEQ ID NO: 36, 37, 38, or 39. In yet another embodiment, the first peptide linker in the fusion protein provided herein independently comprises an SG3S linker having the amino acid sequence of SEQ ID NO: 40, 41, 42, or 43. In yet another embodiment, the first peptide linker in the fusion protein provided herein independently comprises an SG4S linker having the amino acid sequence of SEQ ID NO: 44, 45, 46, or 47. In yet another embodiment, the first peptide linker in the fusion protein provided herein independently comprises an EAAAK linker having the amino acid sequence of SEQ ID NO: 48, 49, 50, or 51. In yet another embodiment, the first peptide linker in the fusion protein provided herein independently comprises a PAPAP linker having the amino acid sequence of SEQ ID NO: 52, 53, 54, or 55. In still another embodiment, the first peptide linker in the fusion protein provided herein independently comprises a VLVH linker having the amino acid sequence of SEQ ID NO: 56.

In one embodiment, the second peptide linker in the fusion protein provided herein independently comprises a peptide linker having an amino acid sequence of GSG or one of SEQ ID NOs: 25 to 56.

In one embodiment, the second peptide linker in the fusion protein provided herein independently comprises a GSG linker having an amino acid sequence of GSG or SEQ ID NO: 25, 26, or 27. In yet another embodiment, the second peptide linker in the fusion protein provided herein independently comprises a G3S linker having the amino acid sequence of SEQ ID NO: 28, 29, 30, or 31. In yet another embodiment, the second peptide linker in the fusion protein provided herein independently comprises a G4S linker having the amino acid sequence of SEQ ID NO: 32, 33, 34, or 35. In yet another embodiment, the second peptide linker in the fusion protein provided herein independently comprises an SGSG linker having the amino acid sequence of SEQ ID NO: 36, 37, 38, or 39. In yet another embodiment, the second peptide linker in the fusion protein independently comprises an SG3S linker having the amino acid sequence of SEQ ID NO: 40, 41, 42, or 43. In yet another embodiment, the second peptide linker in the fusion protein provided herein independently comprises an SG4S linker having the amino acid sequence of SEQ ID NO: 44, 45, 46, or 47. In yet another embodiment, the second peptide linker in the fusion protein provided herein independently comprises an EAAAK linker having the amino acid sequence of SEQ ID NO: 48, 49, 50, or 51. In yet another embodiment, the second peptide linker in the fusion protein provided herein independently comprises a PAPAP linker having the amino acid sequence of SEQ ID NO: 52, 53, 54, or 55. In still another embodiment, the second peptide linker in the fusion protein provided herein independently comprises a VLVH linker having the amino acid sequence of SEQ ID NO: 56.

In one embodiment, in Formula (I), (II), (III), (IV), or (V), $L^1$, $L^C$, and $L^N$ are each independently a bond or a peptide linker having an amino acid sequence of GSG or one of SEQ ID NOs: 25 to 56. In another embodiment, in Formula (I), (II), (III), (IV), or (V), $L^1$ is a bond or a peptide linker having an amino acid sequence of GSG or one of SEQ ID NOs: 25 to 56. In yet another embodiment, in Formula (I), (II), (III), (IV), or (V), $L^C$ is a bond or a peptide linker having an amino acid sequence of GSG or one of SEQ ID NOs: 25 to 56. In still another embodiment, in Formula (I), (II), (III), (IV), or (V), $L^C$ is a bond or a peptide linker having an amino acid sequence of GSG or one of SEQ ID NOs: 25 to 56.

In one embodiment, $L^1$ is a bond. In another embodiment, $L^1$ is a GSG linker having an amino acid sequence of GSG or SEQ ID NO: 25, 26, or 27. In yet another embodiment, $L^1$ is a G3S linker having the amino acid sequence of SEQ ID NO: 28, 29, 30, or 31. In yet another embodiment, $L^1$ is a G4S linker having the amino acid sequence of SEQ ID NO: 32, 33, 34, or 35. In yet another embodiment, $L^1$ is an SGSG linker having the amino acid sequence of SEQ ID NO: 36, 37, 38, or 39. In yet another embodiment, $L^1$ is an SG3S linker having the amino acid sequence of SEQ ID NO: 40, 41, 42, or 43. In yet another embodiment, $L^1$ is an SG4S linker having the amino acid sequence of SEQ ID NO: 44, 45, 46, or 47. In yet another embodiment, $L^1$ is an EAAAK linker having the amino acid sequence of SEQ ID NO: 48, 49, 50, or 51. In yet another embodiment, $L^1$ is a PAPAP linker having the amino acid sequence of SEQ ID NO: 52, 53, 54, or 55. In still another embodiment, $L^1$ is a VLVH linker having the amino acid sequence of SEQ ID NO: 56.

In one embodiment, $L^C$ is a bond. In another embodiment, $L^C$ is a GSG linker having an amino acid sequence of GSG or SEQ ID NO: 25, 26, or 27. In yet another embodiment, $L^C$ is a G3S linker having the amino acid sequence of SEQ ID NO: 28, 29, 30, or 31. In yet another embodiment, $L^C$ is a G4S linker having the amino acid sequence of SEQ ID NO: 32, 33, 34, or 35. In yet another embodiment, $L^C$ is an SGSG linker having the amino acid sequence of SEQ ID NO: 36, 37, 38, or 39. In yet another embodiment, $L^C$ is an SG3S linker having the amino acid sequence of SEQ ID NO: 40, 41, 42, or 43. In yet another embodiment, $L^C$ is an SG4S linker having the amino acid sequence of SEQ ID NO: 44, 45, 46, or 47. In yet another embodiment, $L^C$ is an EAAAK linker having the amino acid sequence of SEQ ID NO: 48, 49, 50, or 51. In yet another embodiment, $L^C$ is a PAPAP linker having the amino acid sequence of SEQ ID NO: 52, 53, 54, or 55. In still another embodiment, $L^C$ is a VLVH linker having the amino acid sequence of SEQ ID NO: 56.

In one embodiment, $L^N$ is a bond. In another embodiment, $L^N$ is a GSG linker having an amino acid sequence of GSG or SEQ ID NO: 25, 26, or 27. In yet another embodiment, $L^N$ is a G3S linker having the amino acid sequence of SEQ ID NO: 28, 29, 30, or 31. In yet another embodiment, $L^N$ is a G4S linker having the amino acid sequence of SEQ ID NO: 32, 33, 34, or 35. In yet another embodiment, $L^N$ is an SGSG linker having the amino acid sequence of SEQ ID NO: 36, 37, 38, or 39. In yet another embodiment, $L^N$ is an SG3S linker having the amino acid sequence of SEQ ID NO: 40, 41, 42, or 43. In yet another embodiment, $L^N$ is an SG4S linker having the amino acid sequence of SEQ ID NO: 44, 45, 46, or 47. In yet another embodiment, $L^N$ is an EAAAK linker having the amino acid sequence of SEQ ID NO: 48, 49, 50, or 51. In yet another embodiment, $L^N$ is a PAPAP linker having the amino acid sequence of SEQ ID NO: 52, 53, 54, or 55. In still another embodiment, $L^N$ is a VLVH linker having the amino acid sequence of SEQ ID NO: 56.

In one embodiment, provided herein is a fusion protein comprising:
- an interleukin-22 domain comprising the amino acid sequence of SEQ ID NO: 1, 2, 3, or 4;
- a $V_HH$ antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and
- a peptide linker comprising an amino acid sequence of GSG or any one of SEQ ID NOs: 25 to 56.

In another embodiment, provided herein is a fusion protein comprising:
- an interleukin-22 domain comprising the amino acid sequence of SEQ ID NO: 2 or 4;
- a $V_HH$ antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and
- a peptide linker comprising an amino acid sequence of GSG or any one of SEQ ID NOs: 28 to 35 and 44 to 47;
- wherein the C-terminus of the interleukin-22 domain is connected to the N-terminus of the $V_HH$ antibody domain via the peptide linker; or wherein the N-terminus of the interleukin-22 domain is connected to the C-terminus of the $V_HH$ antibody domain via the peptide linker.

In yet another embodiment, provided herein is a fusion protein comprising:
- an interleukin-22 domain comprising the amino acid sequence of SEQ ID NO: 2;
- a $V_HH$ antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and
- a peptide linker comprising an amino acid sequence of GSG or any one of SEQ ID NOs: 28 to 35 and 44 to 47;
- wherein the C-terminus of the interleukin-22 domain is connected to the N-terminus of the $V_HH$ antibody domain via the peptide linker; or wherein the N-terminus of the interleukin-22 domain is connected to the C-terminus of the $V_HH$ antibody domain via the peptide linker.

In yet another embodiment, provided herein is a fusion protein comprising an interleukin-22 domain comprising the amino acid sequence of SEQ ID NO: 1, 2, 3, or 4; a $V_HH$ antibody domain comprising the amino acid sequence of SEQ ID NO: 17 or 24; and a peptide linker comprising an amino acid sequence of GSG or any one of SEQ ID NOs: 25 to 56.

In yet another embodiment, provided herein is a fusion protein comprising an interleukin-22 domain comprising the amino acid sequence of SEQ ID NO: 2 or 4; a $V_HH$ antibody domain comprising the amino acid sequence of SEQ ID NO: 17 or 24; and a peptide linker comprising an amino acid sequence of any one of SEQ ID NOs: 28 to 35 and 44 to 47; wherein the C-terminus of the interleukin-22 domain is connected to the N-terminus of the $V_HH$ antibody domain via the peptide linker; or wherein the N-terminus of the interleukin-22 domain is connected to the C-terminus of the $V_HH$ antibody domain via the peptide linker.

In yet another embodiment, provided herein is a fusion protein comprising an interleukin-22 domain, a $V_HH$ antibody domain, and a peptide linker; wherein the fusion protein comprises an amino acid sequence of any one of SEQ ID NOs: 57 to 63.

In still another embodiment, provided herein is a fusion protein comprising an interleukin-22 domain, a $V_HH$ antibody domain, and a peptide linker; wherein the fusion protein comprises an amino acid sequence of SEQ ID NO: 57, 61, 62, or 63.

In one embodiment, provided herein is a fusion protein comprising:
- first and second interleukin-22 domains, each independently comprising the amino acid sequence of SEQ ID NO: 1, 2, 3, or 4;

a V$_H$H antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and first and second peptide linkers, each independently comprising an amino acid sequence of GSG or any one of SEQ ID NOs: 25 to 56.

In another embodiment, provided herein is a fusion protein comprising:

first and second interleukin-22 domains, each independently comprising the amino acid sequence of SEQ ID NO: 2 or 4;

a V$_H$H antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and first and second peptide linkers, each independently comprising an amino acid sequence of GSG or any one of SEQ ID NOs: 28 to 35 and 44 to 47;

wherein the C-terminus of the first interleukin-22 domain is connected to the N-terminus of the V$_H$H antibody domain via the first peptide linker, and the C-terminus of the V$_H$H antibody domain is connected to the N-terminus of the second interleukin-22 domain via the second peptide linker; or wherein the C-terminus of the first interleukin-22 domain is connected to the N-terminus of the second interleukin-22 domain via the first peptide linker, and the C-terminus of the second interleukin-22 domain is connected to the N-terminus of the V$_H$H antibody domain via the second peptide linker; or wherein the C-terminus of the V$_H$H antibody domain is connected to the N-terminus of the first interleukin-22 domain via the first peptide linker, and the C-terminus of the first interleukin-22 domain is connected to the N-terminus of the second interleukin-22 domain via the second peptide linker.

In yet another embodiment, provided herein is a fusion protein comprising:

first and second interleukin-22 domains, each comprising the amino acid sequence of SEQ ID NO: 2;

a V$_H$H antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and first and second peptide linkers, each independently comprising an amino acid sequence of GSG or any one of SEQ ID NOs: 28 to 35 and 44 to 47;

wherein the C-terminus of the first interleukin-22 domain is connected to the N-terminus of the V$_H$H antibody domain via the first peptide linker, and the C-terminus of the V$_H$H antibody domain is connected to the N-terminus of the second interleukin-22 domain via the second peptide linker; or wherein the C-terminus of the first interleukin-22 domain is connected to the N-terminus of the second interleukin-22 domain via the first peptide linker, and the C-terminus of the second interleukin-22 domain is connected to the N-terminus of the V$_H$H antibody domain via the second peptide linker; or wherein the C-terminus of the V$_H$H antibody domain is connected to the N-terminus of the first interleukin-22 domain via the first peptide linker, and the C-terminus of the first interleukin-22 domain is connected to the N-terminus of the second interleukin-22 domain via the second peptide linker.

In yet another embodiment, provided herein is a fusion protein comprising:

first and second interleukin-22 domains, each independently comprising the amino acid sequence of SEQ ID NO: 1, 2, 3, or 4;

a V$_H$H antibody domain comprising the amino acid sequence of SEQ ID NO: 17 or 24; and first and second peptide linkers, each independently comprising an amino acid sequence of GSG or any one of SEQ ID NOs: 25 to 56.

In yet another embodiment, provided herein is a fusion protein comprising:

first and second interleukin-22 domains, each independently comprising the amino acid sequence of SEQ ID NO: 2 or 4;

a V$_H$H antibody domain comprising the amino acid sequence of SEQ ID NO: 17 or 24; and first and second peptide linkers, each independently comprising an amino acid sequence of GSG or any one of SEQ ID NOs: 25 to 56;

wherein the C-terminus of the first interleukin-22 domain is connected to the N-terminus of the V$_H$H antibody domain via the first peptide linker, and the C-terminus of the V$_H$H antibody domain is connected to the N-terminus of the second interleukin-22 domain via the second peptide linker; or wherein the C-terminus of the first interleukin-22 domain is connected to the N-terminus of the second interleukin-22 domain via the first peptide linker, and the C-terminus of the second interleukin-22 domain is connected to the N-terminus of the V$_H$H antibody domain via the second peptide linker; or wherein the C-terminus of the V$_H$H antibody domain is connected to the N-terminus of the first interleukin-22 domain via the first peptide linker, and the C-terminus of the first interleukin-22 domain is connected to the N-terminus of the second interleukin-22 domain via the second peptide linker.

In yet another embodiment, provided herein is a fusion protein comprising:

first and second interleukin-22 domains, each comprising the amino acid sequence of SEQ ID NO: 2;

a V$_H$H antibody domain comprising the amino acid sequence of SEQ ID NO: 17 or 24; and first and second peptide linkers, each independently comprising an amino acid sequence of GSG or any one of SEQ ID NOs: 25 to 56;

wherein the C-terminus of the first interleukin-22 domain is connected to the N-terminus of the V$_H$H antibody domain via the first peptide linker, and the C-terminus of the V$_H$H antibody domain is connected to the N-terminus of the second interleukin-22 domain via the second peptide linker; or wherein the C-terminus of the first interleukin-22 domain is connected to the N-terminus of the second interleukin-22 domain via the first peptide linker, and the C-terminus of the second interleukin-22 domain is connected to the N-terminus of the V$_H$H antibody domain via the second peptide linker; or wherein the C-terminus of the V$_H$H antibody domain is connected to the N-terminus of the first interleukin-22 domain via the first peptide linker, and the C-terminus of the first interleukin-22 domain is connected to the N-terminus of the second interleukin-22 domain via the second peptide linker.

In yet another embodiment, provided herein is a fusion protein comprising first and second interleukin-22 domains, one V$_H$H antibody domain, and first and second peptide linkers; wherein the fusion protein comprises an amino acid sequence of any one of SEQ ID NOs: 64 to 70.

In still another embodiment, provided herein is a fusion protein comprising first and second interleukin-22 domains, one V$_H$H antibody domain, and first and second peptide linkers; wherein the fusion protein comprises an amino acid sequence of SEQ ID NO: 67, 68, 69, or 70.

In one embodiment, provided herein is a fusion protein comprising:
- an interleukin-22 domain comprising the amino acid sequence of SEQ ID NO: 1, 2, 3, or 4;
- a GLP-2 domain comprising the amino acid sequence of SEQ ID NO: 5, 6, or 7;
- a V$_H$H antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and
- first and second peptide linkers, each independently comprising an amino acid sequence of GSG or any one of SEQ ID NOs: 25 to 56.

In another embodiment, provided herein is a fusion protein comprising:
- an interleukin-22 domain comprising the amino acid sequence of SEQ ID NO: 2 or 4;
- a GLP-2 domain comprising the amino acid sequence of SEQ ID NO: 6 or 7;
- a V$_H$H antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and
- first and second peptide linkers, each independently comprising an amino acid sequence of GSG or any one of SEQ ID NOs: 28 to 35 and 44 to 47;
- wherein the C-terminus of the GLP-2 domain is connected to the N-terminus of the interleukin-22 domain via the first peptide linker, and the C-terminus of the interleukin-22 domain is connected to the N-terminus of the V$_H$H antibody domain via the second peptide linker; or
- wherein the C-terminus of the GLP-2 domain is connected to the N-terminus of the V$_H$H antibody domain via the first peptide linker, and the C-terminus of the V$_H$H antibody domain is connected to the N-terminus of the interleukin-22 domain via the second peptide linker; or
- wherein the C-terminus of the interleukin-22 domain is connected to the N-terminus of the V$_H$H antibody domain via the first peptide linker, and the C-terminus of the V$_H$H antibody domain is connected to the N-terminus of the GLP-2 domain via the second peptide linker; or
- wherein the C-terminus of the V$_H$H antibody domain is connected to the N-terminus of the interleukin-22 domain via the first peptide linker, and the C-terminus of the interleukin-22 domain is connected to the N-terminus of the GLP-2 domain via the second peptide linker.

In yet another embodiment, provided herein is a fusion protein comprising:
- an interleukin-22 domain comprising the amino acid sequence of SEQ ID NO: 2;
- a GLP-2 domain comprising the amino acid sequence of SEQ ID NO: 6 or 7;
- a V$_H$H antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and
- first and second peptide linkers, each independently comprising an amino acid sequence of GSG or any one of SEQ ID NOs: 28 to 35 and 44 to 47;
- wherein the C-terminus of the GLP-2 domain is connected to the N-terminus of the interleukin-22 domain via the first peptide linker, and the C-terminus of the interleukin-22 domain is connected to the N-terminus of the V$_H$H antibody domain via the second peptide linker; or
- wherein the C-terminus of the GLP-2 domain is connected to the N-terminus of the V$_H$H antibody domain via the first peptide linker, and the C-terminus of the V$_H$H antibody domain is connected to the N-terminus of the interleukin-22 domain via the second peptide linker; or
- wherein the C-terminus of the interleukin-22 domain is connected to the N-terminus of the V$_H$H antibody domain via the first peptide linker, and the C-terminus of the V$_H$H antibody domain is connected to the N-terminus of the GLP-2 domain via the second peptide linker; or
- wherein the C-terminus of the V$_H$H antibody domain is connected to the N-terminus of the interleukin-22 domain via the first peptide linker, and the C-terminus of the interleukin-22 domain is connected to the N-terminus of the GLP-2 domain via the second peptide linker.

In yet another embodiment, provided herein is a fusion protein comprising:
- an interleukin-22 domain comprising the amino acid sequence of SEQ ID NO: 1, 2, 3, or 4;
- a GLP-2 domain comprising the amino acid sequence of SEQ ID NO: 5, 6, or 7;
- a V$_H$H antibody domain comprising the amino acid sequence of SEQ ID NO: 17 or 24; and
- first and second peptide linkers, each independently comprising an amino acid sequence of GSG or any one of SEQ ID NOs: 25 to 56.

In yet another embodiment, provided herein is a fusion protein comprising:
- an interleukin-22 domain comprising the amino acid sequence of SEQ ID NO: 2 or 4;
- a GLP-2 domain comprising the amino acid sequence of SEQ ID NO: 6 or 7;
- a V$_H$H antibody domain comprising the amino acid sequence of SEQ ID NO: 17 or 24; and
- first and second peptide linkers, each independently comprising an amino acid sequence of GSG or any one of SEQ ID NOs: 25 to 56;
- wherein the C-terminus of the GLP-2 domain is connected to the N-terminus of the interleukin-22 domain via the first peptide linker, and the C-terminus of the interleukin-22 domain is connected to the N-terminus of the V$_H$H antibody domain via the second peptide linker; or wherein the C-terminus of the GLP-2 domain is connected to the N-terminus of the V$_H$H antibody domain via the first peptide linker, and the C-terminus of the V$_H$H antibody domain is connected to the N-terminus of the interleukin-22 domain via the second peptide linker; or wherein the C-terminus of the interleukin-22 domain is connected to the N-terminus of the V$_H$H antibody domain via the first peptide linker, and the C-terminus of the V$_H$H antibody domain is connected to the N-terminus of the GLP-2 domain via the second peptide linker; or wherein the C-terminus of the V$_H$H antibody domain is connected to the N-terminus of the interleukin-22 domain via the first peptide linker, and the C-terminus of the interleukin-22 domain is connected to the N-terminus of the GLP-2 domain via the second peptide linker.

In yet another embodiment, provided herein is a fusion protein comprising:
an interleukin-22 domain comprising the amino acid sequence of SEQ ID NO: 2;
a GLP-2 domain comprising the amino acid sequence of SEQ ID NO: 6 or 7;
a V$_H$H antibody domain comprising the amino acid sequence of SEQ ID NO: 17 or 24; and
first and second peptide linkers, each independently comprising an amino acid sequence of GSG or any one of SEQ ID NOs: 25 to 56;
wherein the C-terminus of the GLP-2 domain is connected to the N-terminus of the interleukin-22 domain via the first peptide linker, and the C-terminus of the interleukin-22 domain is connected to the N-terminus of the V$_H$H antibody domain via the second peptide linker; or
wherein the C-terminus of the GLP-2 domain is connected to the N-terminus of the V$_H$H antibody domain via the first peptide linker, and the C-terminus of the V$_H$H antibody domain is connected to the N-terminus of the interleukin-22 domain via the second peptide linker; or
wherein the C-terminus of the interleukin-22 domain is connected to the N-terminus of the V$_H$H antibody domain via the first peptide linker, and the C-terminus of the V$_H$H antibody domain is connected to the N-terminus of the GLP-2 domain via the second peptide linker; or
wherein the C-terminus of the V$_H$H antibody domain is connected to the N-terminus of the interleukin-22 domain via the first peptide linker, and the C-terminus of the interleukin-22 domain is connected to the N-terminus of the GLP-2 domain via the second peptide linker.

In yet another embodiment, provided herein is a fusion protein comprising an interleukin-22 domain, a GLP-2 domain, a V$_H$H antibody domain, and first and second peptide linkers; wherein the fusion protein comprises an amino acid sequence of any one of SEQ ID NOs: 71 to 78.

In still another embodiment, provided herein is a fusion protein comprising an interleukin-22 domain, a GLP-2 domain, a V$_H$H antibody domain, and first and second peptide linkers; wherein the fusion protein comprises an amino acid sequence of SEQ ID NO: 72, 73, 74, 76, 77, or 78.

In one embodiment, provided herein is a fusion protein comprising:
an interleukin-22 domain comprising the amino acid sequence of SEQ ID NO: 1, 2, 3, or 4;
an IGF-1 domain comprising the amino acid sequence of SEQ ID NO: 8 or 9;
a V$_H$H antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and
first and second peptide linkers, each independently comprising an amino acid sequence of GSG or any one of SEQ ID NOs: 25 to 56.

In another embodiment, provided herein is a fusion protein comprising:
an interleukin-22 domain comprising the amino acid sequence of SEQ ID NO: 2 or 4;
an IGF-1 domain comprising the amino acid sequence of SEQ ID NO: 9;
a V$_H$H antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and
first and second peptide linkers, each independently comprising an amino acid sequence of GSG or any one of SEQ ID NOs: 28 to 35 and 44 to 47;
wherein the C-terminus of the IGF-1 domain is connected to the N-terminus of the interleukin-22 domain via the first peptide linker, and the C-terminus of the interleukin-22 domain is connected to the N-terminus of the V$_H$H antibody domain via the second peptide linker; or
wherein the C-terminus of the IGF-1 domain is connected to the N-terminus of the V$_H$H antibody domain via the first peptide linker, and the C-terminus of the V$_H$H antibody domain is connected to the N-terminus of the interleukin-22 domain via the second peptide linker; or
wherein the C-terminus of the interleukin-22 domain is connected to the N-terminus of the V$_H$H antibody domain via the first peptide linker, and the C-terminus of the V$_H$H antibody domain is connected to the N-terminus of the IGF-1 domain via the second peptide linker; or
wherein the C-terminus of the V$_H$H antibody domain is connected to the N-terminus of the interleukin-22 domain via the first peptide linker, and the C-terminus of the interleukin-22 domain is connected to the N-terminus of the IGF-1 domain via the second peptide linker.

In yet another embodiment, provided herein is a fusion protein comprising:
an interleukin-22 domain comprising the amino acid sequence of SEQ ID NO: 2;
an IGF-1 domain comprising the amino acid sequence of SEQ ID NO: 9;
a V$_H$H antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and
first and second peptide linkers, each independently comprising an amino acid sequence of GSG or any one of SEQ ID NOs: 28 to 35 and 44 to 47;
wherein the C-terminus of the IGF-1 domain is connected to the N-terminus of the interleukin-22 domain via the first peptide linker, and the C-terminus of the interleukin-22 domain is connected to the N-terminus of the V$_H$H antibody domain via the second peptide linker; or wherein the C-terminus of the IGF-1 domain is connected to the N-terminus of the V$_H$H antibody domain via the first peptide linker, and the C-terminus of the V$_H$H antibody domain is connected to the N-terminus of the interleukin-22 domain via the second peptide linker; or wherein the C-terminus of the interleukin-22 domain is connected to the N-terminus of the V$_H$H antibody domain via the first peptide linker, and the C-terminus of the V$_H$H antibody domain is connected to the N-terminus of the IGF-1 domain via the second peptide linker; or wherein the C-terminus of the V$_H$H antibody domain is connected to the N-terminus of the interleukin-22 domain via the first peptide linker, and the C-terminus of the interleukin-22 domain is connected to the N-terminus of the IGF-1 domain via the second peptide linker.

In yet another embodiment, provided herein is a fusion protein comprising:
- an interleukin-22 domain comprising the amino acid sequence of SEQ ID NO: 1, 2, 3, or 4;
- an IGF-1 domain comprising the amino acid sequence of SEQ ID NO: 8 or 9;
- a V$_H$H antibody domain comprising the amino acid sequence of SEQ ID NO: 17 or 24; and
- first and second peptide linkers, each independently comprising an amino acid sequence of GSG or any one of SEQ ID NOs: 25 to 56.

In yet another embodiment, provided herein is a fusion protein comprising:
- an interleukin-22 domain comprising the amino acid sequence of SEQ ID NO: 2 or 4;
- an IGF-1 domain comprising the amino acid sequence of SEQ ID NO: 9;
- a V$_H$H antibody domain comprising the amino acid sequence of SEQ ID NO: 17 or 24; and
- first and second peptide linkers, each independently comprising an amino acid sequence of GSG or any one of SEQ ID NOs: 25 to 56;

wherein the C-terminus of the IGF-1 domain is connected to the N-terminus of the interleukin-22 domain via the first peptide linker, and the C-terminus of the interleukin-22 domain is connected to the N-terminus of the V$_H$H antibody domain via the second peptide linker; or wherein the C-terminus of the IGF-1 domain is connected to the N-terminus of the V$_H$H antibody domain via the first peptide linker, and the C-terminus of the V$_H$H antibody domain is connected to the N-terminus of the interleukin-22 domain via the second peptide linker; or wherein the C-terminus of the interleukin-22 domain is connected to the N-terminus of the V$_H$H antibody domain via the first peptide linker, and the C-terminus of the V$_H$H antibody domain is connected to the N-terminus of the IGF-1 domain via the second peptide linker; or wherein the C-terminus of the V$_H$H antibody domain is connected to the N-terminus of the interleukin-22 domain via the first peptide linker, and the C-terminus of the interleukin-22 domain is connected to the N-terminus of the IGF-1 domain via the second peptide linker.

In yet another embodiment, provided herein is a fusion protein comprising:
- an interleukin-22 domain comprising the amino acid sequence of SEQ ID NO: 2;
- an IGF-1 domain comprising the amino acid sequence of SEQ ID NO: 9;
- a V$_H$H antibody domain comprising the amino acid sequence of SEQ ID NO: 17 or 24; and
- first and second peptide linkers, each independently comprising an amino acid sequence of GSG or any one of SEQ ID NOs: 25 to 56;

wherein the C-terminus of the IGF-1 domain is connected to the N-terminus of the interleukin-22 domain via the first peptide linker, and the C-terminus of the interleukin-22 domain is connected to the N-terminus of the V$_H$H antibody domain via the second peptide linker; or wherein the C-terminus of the IGF-1 domain is connected to the N-terminus of the V$_H$H antibody domain via the first peptide linker, and the C-terminus of the V$_H$H antibody domain is connected to the N-terminus of the interleukin-22 domain via the second peptide linker; or wherein the C-terminus of the interleukin-22 domain is connected to the N-terminus of the V$_H$H antibody domain via the first peptide linker, and the C-terminus of the V$_H$H antibody domain is connected to the N-terminus of the IGF-1 domain via the second peptide linker; or wherein the C-terminus of the V$_H$H antibody domain is connected to the N-terminus of the interleukin-22 domain via the first peptide linker, and the C-terminus of the interleukin-22 domain is connected to the N-terminus of the IGF-1 domain via the second peptide linker.

In yet another embodiment, provided herein is a fusion protein comprising an interleukin-22 domain, an IGF-1 domain, a V$_H$H antibody domain, and first and second peptide linkers; wherein the fusion protein comprises an amino acid sequence of any one of SEQ ID NOs: 79 to 86.

In still another embodiment, provided herein is a fusion protein comprising an interleukin-22 domain, an IGF-1 domain, a V$_H$H antibody domain, and first and second peptide linkers; wherein the fusion protein comprises an amino acid sequence of SEQ ID NO: 80, 81, 82, 84, 85, or 86.

In one embodiment, provided herein is a fusion protein comprising:
- first and second interleukin-22 domains, each independently comprising the amino acid sequence of SEQ ID NO: 1, 2, 3, or 4;
- a GLP-2 domain comprising the amino acid sequence of SEQ ID NO: 5, 6, or 7;
- a V$_H$H antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and
- first and second peptide linkers, each independently comprising an amino acid sequence of GSG or any one of SEQ ID NOs: 25 to 56.

In another embodiment, provided herein is a fusion protein comprising:
- first and second interleukin-22 domains, each independently comprising the amino acid sequence of SEQ ID NO: 2 or 4;
- a GLP-2 domain comprising the amino acid sequence of SEQ ID NO: 6 or 7;
- a V$_H$H antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and first, second, and third peptide linkers, each independently comprising an amino acid sequence of GSG or any one of SEQ ID NOs: 28 to 35 and 44 to 47;

wherein the C-terminus of the GLP-2 domain is connected to the N-terminus of the first interleukin-22 domain via the first peptide linker; the C-terminus of the first interleukin-22 domain is connected to the N-terminus of the V$_H$H antibody domain via the second peptide linker, and the C-terminus of the V$_H$H antibody domain is connected to the N-terminus of the second interleukin-22 domain via the third peptide linker; or wherein the C-terminus of the first interleukin-22 domain is connected to the N-terminus of the V$_H$H antibody domain via the first peptide linker; the C-terminus of the V$_H$H antibody domain is connected to the N-terminus of the second interleukin-22 domain via the second peptide linker; the C-terminus of the second interleukin-22 domain is connected to the N-terminus of the GLP-2 domain via the third peptide linker.

In yet another embodiment, provided herein is a fusion protein comprising:
first and second interleukin-22 domains, each comprising the amino acid sequence of SEQ ID NO: 2;
a GLP-2 domain comprising the amino acid sequence of SEQ ID NO: 6 or 7;
a V$_H$H antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and
first, second, and third peptide linkers, each independently comprising an amino acid sequence of GSG or any one of SEQ ID NOs: 28 to 35 and 44 to 47;
wherein the C-terminus of the GLP-2 domain is connected to the N-terminus of the first interleukin-22 domain via the first peptide linker; the C-terminus of the first interleukin-22 domain is connected to the N-terminus of the V$_H$H antibody domain via the second peptide linker, and the C-terminus of the V$_H$H antibody domain is connected to the N-terminus of the second interleukin-22 domain via the third peptide linker; or
wherein the C-terminus of the first interleukin-22 domain is connected to the N-terminus of the V$_H$H antibody domain via the first peptide linker; the C-terminus of the V$_H$H antibody domain is connected to the N-terminus of the second interleukin-22 domain via the second peptide linker; the C-terminus of the second interleukin-22 domain is connected to the N-terminus of the GLP-2 domain via the third peptide linker.

In yet another embodiment, provided herein is a fusion protein comprising:
first and second interleukin-22 domains, each independently comprising the amino acid sequence of SEQ ID NO: 1, 2, 3, or 4;
a GLP-2 domain comprising the amino acid sequence of SEQ ID NO: 5, 6, or 7;
a V$_H$H antibody domain comprising the amino acid sequence of SEQ ID NO: 17 or 24; and
first, second, and third peptide linkers, each independently comprising an amino acid sequence of GSG or any one of SEQ ID NOs: 25 to 56.

In yet another embodiment, provided herein is a fusion protein comprising:
first and second interleukin-22 domains, each independently comprising the amino acid sequence of SEQ ID NO: 2 or 4;

a GLP-2 domain comprising the amino acid sequence of SEQ ID NO: 6 or 7;
a V$_H$H antibody domain comprising the amino acid sequence of SEQ ID NO: 17 or 24; and
first, second, and third peptide linkers, each independently comprising an amino acid sequence of GSG or any one of SEQ ID NOs: 25 to 56;
wherein the C-terminus of the GLP-2 domain is connected to the N-terminus of the first interleukin-22 domain via the first peptide linker; the C-terminus of the first interleukin-22 domain is connected to the N-terminus of the V$_H$H antibody domain via the second peptide linker, and the C-terminus of the V$_H$H antibody domain is connected to the N-terminus of the second interleukin-22 domain via the third peptide linker; or
wherein the C-terminus of the first interleukin-22 domain is connected to the N-terminus of the V$_H$H antibody domain via the first peptide linker; the C-terminus of the V$_H$H antibody domain is connected to the N-terminus of the second interleukin-22 domain via the second peptide linker; the C-terminus of the second interleukin-22 domain is connected to the N-terminus of the GLP-2 domain via the third peptide linker.

In yet another embodiment, provided herein is a fusion protein comprising:
first and second interleukin-22 domains, each comprising the amino acid sequence of SEQ ID NO: 2;
a GLP-2 domain comprising the amino acid sequence of SEQ ID NO: 6 or 7;
a V$_H$H antibody domain comprising the amino acid sequence of SEQ ID NO: 17 or 24; and
first, second, and third peptide linkers, each independently comprising an amino acid sequence of GSG or any one of SEQ ID NOs: 25 to 56;
wherein the C-terminus of the GLP-2 domain is connected to the N-terminus of the first interleukin-22 domain via the first peptide linker; the C-terminus of the first interleukin-22 domain is connected to the N-terminus of the V$_H$H antibody domain via the second peptide linker, and the C-terminus of the V$_H$H antibody domain is connected to the N-terminus of the second interleukin-22 domain via the third peptide linker; or
wherein the C-terminus of the first interleukin-22 domain is connected to the N-terminus of the V$_H$H antibody domain via the first peptide linker; the C-terminus of the V$_H$H antibody domain is connected to the N-terminus of the second interleukin-22 domain via the second peptide linker; the C-terminus of the second interleukin-22 domain is connected to the N-terminus of the GLP-2 domain via the third peptide linker.

In yet another embodiment, provided herein is a fusion protein comprising first and second interleukin-22 domains, a GLP-2 domain, a V$_H$H antibody domain, and first, second, and third peptide linkers; wherein the fusion protein comprises an amino acid sequence of any one of SEQ ID NOs: 87 to 90.

In still another embodiment, provided herein is a fusion protein comprising first and second interleukin-22 domains, a GLP-2 domain, a V$_H$H antibody domain, and first, second, and third peptide linkers; wherein the fusion protein comprises an amino acid sequence of SEQ ID NO: 88 or 90.

In one embodiment, provided herein is a fusion protein comprising:
first and second interleukin-22 domains, each independently comprising the amino acid sequence of SEQ ID NO: 1, 2, 3, or 4;

an IGF-1 domain comprising the amino acid sequence of SEQ ID NO: 8 or 9;
a V$_H$H antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and
first and second peptide linkers, each independently comprising an amino acid sequence of GSG or any one of SEQ ID NOs: 25 to 56.

In another embodiment, provided herein is a fusion protein comprising:
first and second interleukin-22 domains, each independently comprising the amino acid sequence of SEQ ID NO: 2 or 4;
an IGF-1 domain comprising the amino acid sequence of SEQ ID NO: 8 or 9;
a V$_H$H antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and
first, second, and third peptide linkers, each independently comprising an amino acid sequence of GSG or any one of SEQ ID NOs: 28 to 35 and 44 to 47;
wherein the C-terminus of the IGF-1 domain is connected to the N-terminus of the first interleukin-22 domain via the first peptide linker; the C-terminus of the first interleukin-22 domain is connected to the N-terminus of the V$_H$H antibody domain via the second peptide linker, and the C-terminus of the V$_H$H antibody domain is connected to the N-terminus of the second interleukin-22 domain via the third peptide linker; or
wherein the C-terminus of the first interleukin-22 domain is connected to the N-terminus of the V$_H$H antibody domain via the first peptide linker; the C-terminus of the V$_H$H antibody domain is connected to the N-terminus of the second interleukin-22 domain via the second peptide linker; the C-terminus of the second interleukin-22 domain is connected to the N-terminus of the IGF-1 domain via the third peptide linker.

In yet another embodiment, provided herein is a fusion protein comprising:
first and second interleukin-22 domains, each comprising the amino acid sequence of SEQ ID NO: 2;
an IGF-1 domain comprising the amino acid sequence of SEQ ID NO: 9;
a V$_H$H antibody domain comprising (i) a CDR1 of SEQ ID NO: 10, a CDR2 of SEQ ID NO: 11, and a CDR3 of SEQ ID NO: 12; or (ii) a CDR1 of SEQ ID NO: 18, a CDR2 of SEQ ID NO: 19, and a CDR3 of SEQ ID NO: 20; and
first, second, and third peptide linkers, each independently comprising an amino acid sequence of GSG or any one of SEQ ID NOs: 28 to 35 and 44 to 47;
wherein the C-terminus of the IGF-1 domain is connected to the N-terminus of the first interleukin-22 domain via the first peptide linker; the C-terminus of the first interleukin-22 domain is connected to the N-terminus of the V$_H$H antibody domain via the second peptide linker, and the C-terminus of the V$_H$H antibody domain is connected to the N-terminus of the second interleukin-22 domain via the third peptide linker; or
wherein the C-terminus of the first interleukin-22 domain is connected to the N-terminus of the V$_H$H antibody domain via the first peptide linker; the C-terminus of the V$_H$H antibody domain is connected to the N-terminus of the second interleukin-22 domain via the second peptide linker; the C-terminus of the second interleukin-22 domain is connected to the N-terminus of the IGF-1 domain via the third peptide linker.

In yet another embodiment, provided herein is a fusion protein comprising:
first and second interleukin-22 domains, each independently comprising the amino acid sequence of SEQ ID NO: 1, 2, 3, or 4;
an IGF-1 domain comprising the amino acid sequence of SEQ ID NO: 8 or 9;
a V$_H$H antibody domain comprising the amino acid sequence of SEQ ID NO: 17 or 24; and
first, second, and third peptide linkers, each independently comprising an amino acid sequence of GSG or any one of SEQ ID NOs: 25 to 56.

In yet another embodiment, provided herein is a fusion protein comprising:
first and second interleukin-22 domains, each independently comprising the amino acid sequence of SEQ ID NO: 2 or 4;
an IGF-1 domain comprising the amino acid sequence of SEQ ID NO: 9;
a V$_H$H antibody domain comprising the amino acid sequence of SEQ ID NO: 17 or 24; and
first, second, and third peptide linkers, each independently comprising an amino acid sequence of GSG or any one of SEQ ID NOs: 25 to 56;
wherein the C-terminus of the IGF-1 domain is connected to the N-terminus of the first interleukin-22 domain via the first peptide linker; the C-terminus of the first interleukin-22 domain is connected to the N-terminus of the V$_H$H antibody domain via the second peptide linker, and the C-terminus of the V$_H$H antibody domain is connected to the N-terminus of the second interleukin-22 domain via the third peptide linker; or
wherein the C-terminus of the first interleukin-22 domain is connected to the N-terminus of the V$_H$H antibody domain via the first peptide linker; the C-terminus of the V$_H$H antibody domain is connected to the N-terminus of the second interleukin-22 domain via the second peptide linker; the C-terminus of the second interleukin-22 domain is connected to the N-terminus of the IGF-1 domain via the third peptide linker.

In yet another embodiment, provided herein is a fusion protein comprising:
first and second interleukin-22 domains, each comprising the amino acid sequence of SEQ ID NO: 2;
an IGF-1 domain comprising the amino acid sequence of SEQ ID NO: 9;
a V$_H$H antibody domain comprising the amino acid sequence of SEQ ID NO: 17 or 24; and
first, second, and third peptide linkers, each independently comprising an amino acid sequence of GSG or any one of SEQ ID NOs: 25 to 56;
wherein the C-terminus of the IGF-1 domain is connected to the N-terminus of the first interleukin-22 domain via the first peptide linker; the C-terminus of the first interleukin-22 domain is connected to the N-terminus of the V$_H$H antibody domain via the second peptide linker, and the C-terminus of the V$_H$H antibody domain is connected to the N-terminus of the second interleukin-22 domain via the third peptide linker; or
wherein the C-terminus of the first interleukin-22 domain is connected to the N-terminus of the V$_H$H antibody domain via the first peptide linker; the C-terminus of the V$_H$H antibody domain is connected to the N-terminus of the second interleukin-22 domain via the second peptide linker; the C-terminus of the second interleukin-22 domain is connected to the N-terminus of the IGF-1 domain via the third peptide linker.

In yet another embodiment, provided herein is a fusion protein comprising first and second interleukin-22 domains, an IGF-1 domain, a $V_HH$ antibody domain, and first, second, and third peptide linkers; wherein the fusion protein comprises an amino acid sequence of any one of SEQ ID NOs: 91 to 94.

In still another embodiment, provided herein is a fusion protein comprising first and second interleukin-22 domains, an IGF-1 domain, a $V_HH$ antibody domain, and first, second, and third peptide linkers; wherein the fusion protein comprises an amino acid sequence of SEQ ID NOs: 92 or 94.

In one embodiment, the fusion protein provided herein is produced from a yeast cell, insect cell, mammalian cell, human cell, or plant cell. In another embodiment, the fusion protein provided herein is produced from a yeast cell. In yet another embodiment, the fusion protein provided herein is produced from an insect cell. In yet another embodiment, the fusion protein provided herein is produced from a mammalian cell. In yet another embodiment, the fusion protein provided herein is produced from a CHO cell. In yet another embodiment, the fusion protein provided herein is produced from a human cell. In yet another embodiment, the fusion protein provided herein is produced from a plant cell.

Pharmaceutical Compositions

In one embodiment, provided herein is a pharmaceutical composition comprising a fusion protein provided herein and a pharmaceutically acceptable excipient.

In one embodiment, the pharmaceutical composition is formulated as single dosage form.

In one embodiment, the pharmaceutical composition provided herein is a solid formulation. In another embodiment, the pharmaceutical composition provided herein is a lyophilized solid formulation. In yet another embodiment, the pharmaceutical composition provided herein is a solution. In still another embodiment, the pharmaceutical composition provided herein is an aqueous solution.

In one embodiment, the pharmaceutical composition provided herein is formulated in a dosage form for parenteral administration. In another embodiment, the pharmaceutical composition provided herein is formulated in a dosage form for intravenous administration. In yet another embodiment, the pharmaceutical composition provided herein is formulated in a dosage form for intramuscular administration. In yet another embodiment, the pharmaceutical composition provided herein is formulated in a dosage form for subcutaneous administration. In still another embodiment, the pharmaceutical composition provided herein is formulated in a dosage form for intratumural administration.

Methods of Use

In one embodiment, provided herein is a method for treating, preventing, or ameliorating an inflammatory disease in a subject, comprising administering to the subject in need thereof a therapeutically effective amount of a fusion protein provided herein.

In one embodiment, the inflammatory disease is inflammatory bowel disease. In another embodiment, the inflammatory bowel disease is Crohn's disease. In yet another embodiment, the inflammatory bowel disease is ulcerative colitis.

In certain embodiments, the therapeutically effective amount is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day.

In certain embodiments, the subject is a mammal. In certain embodiments, the subject is a human.

The disclosure will be further understood by the following non-limiting examples.

EXAMPLES

Example 1

Cloning, Expression, and Purification of IL-22 Fusion Proteins

The deoxyoligonucleotide sequences encoding an IL-22 and an anti-HSA $V_HH$ antibody, a GLP-2 or a mutein thereof, and an IGF-1 or a variant thereof were seamlessly assembled together by homology assembly cloning with commercially available kits according to the design of a fusion protein. The oligonucleotide of the fusion protein was inserted into a UCOE® expression vector CET1019-AS-Puro for CHO cell expression.

The oligonucleotide sequence encoding the fusion protein was transiently expressed in EXPICHO™ cells. Briefly, on Day −1, EXPICHO-S™ cells were seeded at 3-4×10⁶ cells/mL with the EXPICHO™ expression medium in a vented Erlenmeyer shake flask. The flask was placed on a 125 rpm orbital shaker in a 37° C. incubator with 8% $CO_2$. On Day 0, plasmid DNA was mixed with the EXPIFECTAMINE™ CHO reagent. The mixture was then slowly added to the cells. After 16 hours, the cells were transferred to a 32° C. incubator with 5% $CO_2$. The cells were fed twice on Day 1 and Day 5 with the EXPICHO™ feed. The CHO cells were harvested on Day 8-12.

The fusion protein produced in the CHO cells was purified by a two-step purification process comprising protein A affinity chromatography using protein A (e.g., AMSPHERE™ A3) resin and ion exchange chromatography (e.g., CAPTO™ S ImpAct).

For the protein A affinity chromatography, a protein A affinity column was loaded with a clarified CHO medium and then washed twice with 20 mM sodium phosphate and once with 20 mM sodium phosphate with 0.5 M NaCl at pH 7.5. The fusion protein was eluted with 50 mM sodium acetate at pH 3.0 supplied with 1% isopropanol by volume.

The purified fusion protein was then buffer exchanged into 20 mM sodium phosphate at pH 6.0 in preparation of AKTA™ purification. The fusion protein was loaded onto 1 mL HiTrap CAPTO™ S ImpAct column. After loading, the column was washed with 20 mM sodium phosphate at pH 6.0 for 10 column volumes (CV). After washing, the fusion protein was eluted with 20 mM sodium phosphate at pH 6.0 plus 1 M NaCl by a gradient of 0-100% in 22.5 CV. The fusion protein was eluted off at ~12 mS/cm. Eluted fractions were pooled and buffer exchanged into a solution containing 5 mM histidine, 20 mM NaCl, and 0.02% TWEEN-80 at pH 4.0 for storage.

Example 2

Binding Affinity Determination of IL-22 Fusion Proteins to IL-22Rα-1

OCTET® RED96 was used to characterize the interactions of an IL-22 fusion protein with a mouse IL-22Rα 1 (mIL22RA1). Briefly, an mIL22RA1-Fc fusion protein was loaded onto an anti-human IgG Fc capture (AHC) biosensor. The biosensor was then dipped into a solution containing the IL-22 fusion protein at 400 nM. Primary experimental data was analyzed with global fitting to determine a dissociation constant ($K_d$). The results are summarized in Table 1 below.

TABLE 1

Binding Affinities of IL-22 Fusion Proteins to IL-22Rα-1

| SEQ ID NO: | Fusion Protein | $K_d$ (nM) |
| --- | --- | --- |
| 57 | hIL-22-anti-HSA A1 | 300 |
| 58 | mIL-22-anti-HSA A2 | 61 |
| 59 | Anti-HSA-mIL-22 A3 | 30 |
| 60 | mIL-22-anti-HSA A4 | 67 |
| 64 | mIL-22-anti-HSA-mIL-22 A8 | 1.2 |
| 65 | mIL-22-anti-HSA-mIL-22 A9 | 0.77 |
| 95 | mIL-22-hIgG1 Fc B1 | 1.4 |

Example 3

Effect of IL-22 Fusion Proteins on STAT3 Signaling

In vitro potency of an IL-22 fusion protein was measured by quantifying phosphorylation of STAT3 in AsPC-1, a pancreatic cancer cell line that expresses endogenous IL-22 receptor. AsPC-1 cells were maintained in RPMI-1640 containing 10% fetal bovine serum and penicillin/streptomycin. Before the day of assay, 100,000 cells per well were seeded in a 96-well plate and grown overnight. Cells were treated with the indicated concentration of recombinant human IL-22 (rhIL-22) or an IL-22 fusion protein for 30 min at 37° C. under 5% $CO_2$ in serum free RPMI-1640 medium. Phospho-STAT3 was measured using a phospho-STAT3 (Tyr705) homogeneous time resolved fluorescence (HTRF) assay. The signal ratio of 665 nm/620 nm was multiplied by 1,000, plotted, and fit using a dose response curve (GraphPad Prism) to calculate an $EC_{50}$ value. The $EC_{50}$ values determined are summarized in Table 2 below.

TABLE 2

Effect of IL-22 Fusion Proteins on STAT3 Signaling

| SEQ ID NO: | Fusion Protein | $EC_{50}$ (μM) |
| --- | --- | --- |
|  | rhIL-22 | 0.09 |
| 57 | hIL-22-anti-HSA A1 | 0.8 |
| 58 | mIL-22-anti-HSA A2 | 0.7 |
| 59 | Anti-HSA-mIL-22 A3 | 0.5 |
| 60 | mIL-22-anti-HSA A4 | 0.6 |
| 64 | mIL-22-anti-HSA-mIL-22 A8 | 0.5 |
| 65 | mIL-22-anti-HSA-mIL-22 A9 | 0.5 |

Example 4

Effect of IL-22 Fusion Proteins on Transepithelial Electrical Resistance

Figure 1:
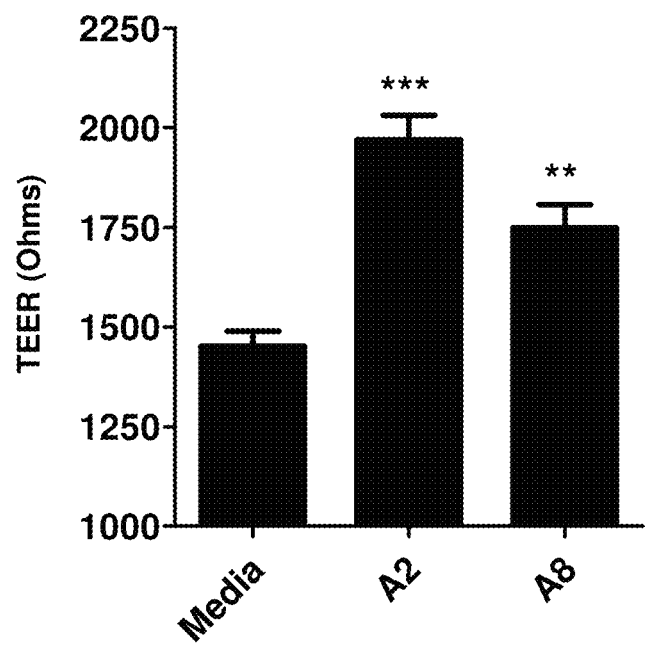
FIG. 1 shows the effect of IL-22 fusion proteins A2 (SEQ ID NO: 58) and A8 (SEQ ID NO: 64) on the transepithelial electrical resistance of human colonic organoids.

Human colonic organoids and organoid-derived monolayers were cultured in supplemented basal media (SBM) with growth factors and chemical compounds. SBM was an advanced DMEM/F12 containing 10 mM HEPES, 2 mM GLUTAMAX™, penicillin/streptomycin, 1:100 N2, 1:50 B27, 1 mM N-acetylcysteine, and 10 nM [Leu15]-gastrin I. The human organoids were maintained in SBM with 100 ng/mL Wnt-3a, 50 ng/mL EGF, 100 ng/mL noggin, 500 ng/mL R-spondin 1, 500 nM A83-01, 10 μM SB202190, and 10 mM nicotinamide before being used to plate monolayer cultures. On Day 0, organoids were treated with TRYPLE™ Express to break organoids into small pieces and/or single cells, and 100,000 cells were plated into the apical side of a 24-well TRANSWELLS® in SBM with 2.5 μM thiazovivin, as well as WENRA (Wnt-3a, EGF, noggin, R-spondin1, and A83-01) at the same concentrations mentioned above. The same media was added to the basolateral side of the plate. Colonic cells were differentiated with ENRA (EGF, noggin, R-spondin1, and A83-01) on Day 3. Human colonic organoid monolayers were cultured in media alone or media containing fusion protein A2 or A8 in the basolateral side from Day 0 to Day 6. Transepithelial electrical resistance (TEER), a measure of tight junction integrity, was determined on Day 6 of culture. As shown in FIG. 1, the addition of fusion protein A2 or A8 resulted in significantly higher TEER than control wells without a fusion protein added, indicating tighter cell-cell junctions between the colonic epithelial cells.

Example 5

Pharmacokinetic Studies of IL-22 Fusion Proteins

Figure 2:
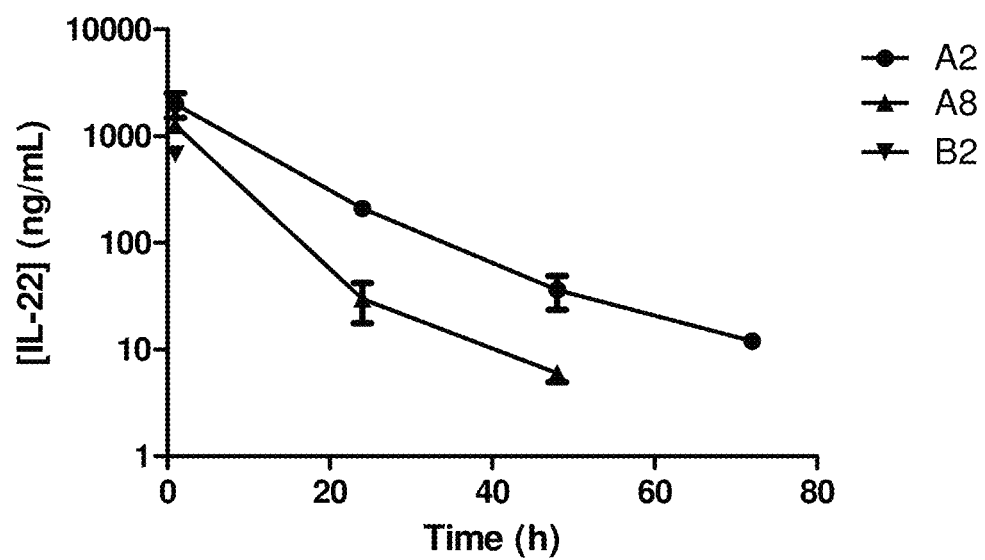
FIG. 2 shows pharmacokinetic profiles of IL-22 fusion proteins A2 (SEQ ID NO: 58) at a dose of 30 μg and A8 (SEQ ID NO: 64) at a dose of 30 μg in mice.

BALB/c mice were injected intraperitoneally with 30 μg of fusion protein A2, A8, or B2. Fusion protein B2 is an IL-22 dimer conjugated to an antibody that does not bind mouse serum albumin with the configuration of IL-22-anti-HSA-IL-22. As shown in FIG. 2, fusion proteins A2 and A8 had significantly longer half-lives compared to control fusion protein B2.

Example 6

Studies of IL-22 Fusion Proteins in a DSS-Induced Colitis Mouse Model

Figure 3:
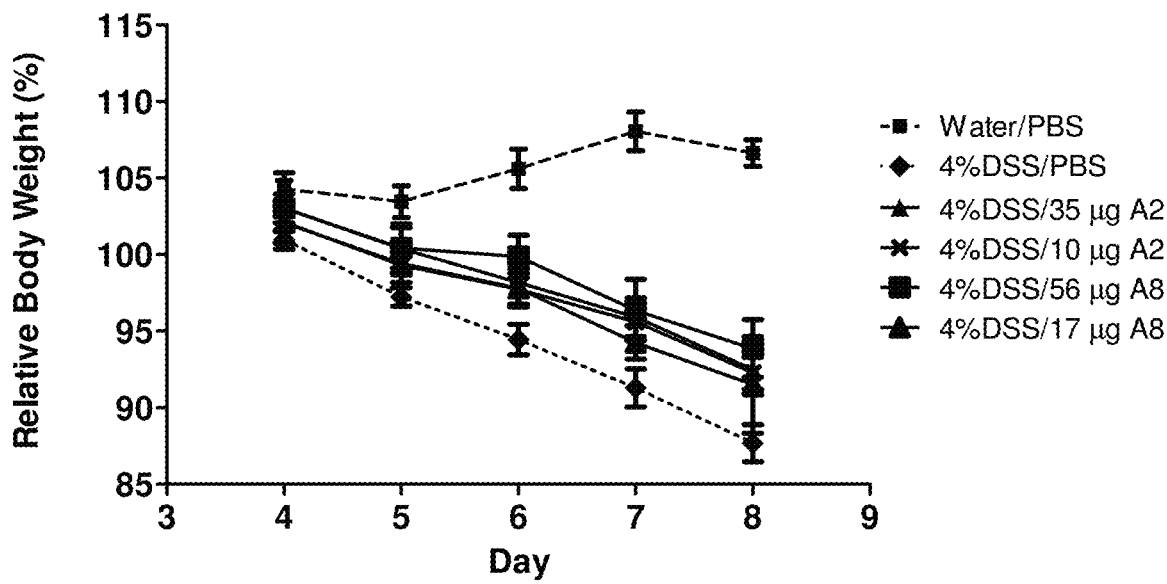
FIG. 3 shows the effect of IL-22 fusion protein A2 (SEQ ID NO: 58) at a dose of 10 or 35 μg and IL-22 fusion protein A8 (SEQ ID NO: 64) at a dose of 17 or 56 μg on the body weights of mice in a dextran sodium sulfate (DSS)-induced colitis model.
Figure 4:
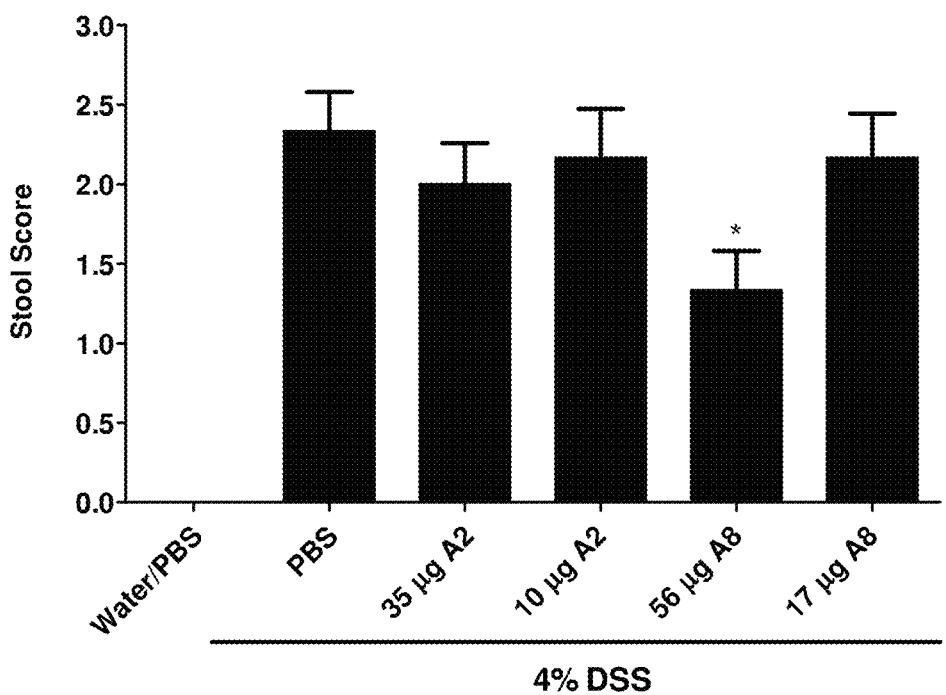
FIG. 4 shows the effect of IL-22 fusion protein A2 (SEQ ID NO: 58) at a dose of 10 or 35 μg and IL-22 fusion protein A8 (SEQ ID NO: 64) at a dose of 17 or 56 μg on the stool scores of mice in a DSS-induced colitis model.
Figure 5:
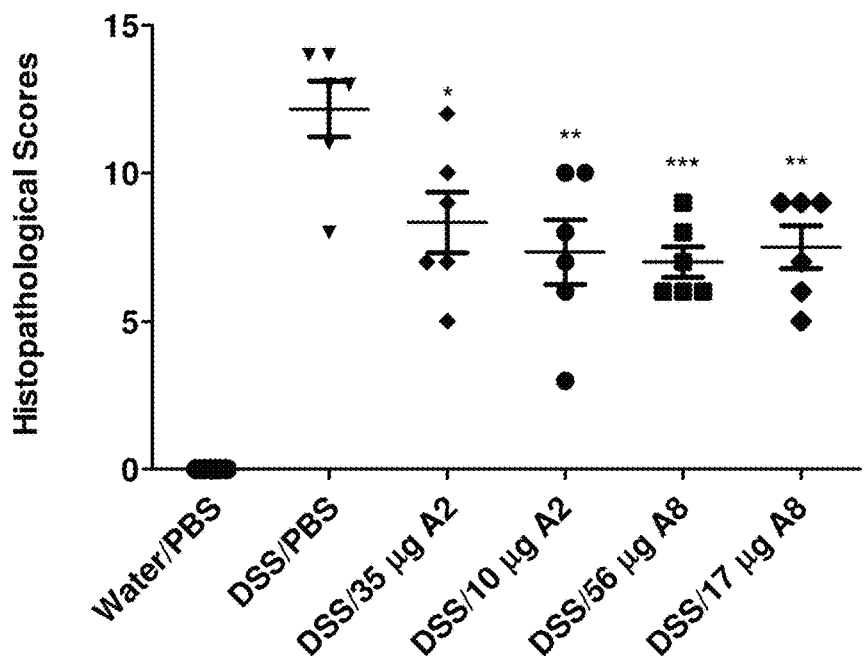
FIG. 5 shows the effect of IL-22 fusion protein A2 (SEQ ID NO: 58) at a dose of 10 or 35 μg and IL-22 fusion protein A8 (SEQ ID NO: 64) at a dose of 17 or 56 μg on the scorings of goblet cell loss of mice in a DSS-induced colitis model.

C57BL/6 mice (N=6) were given water or water containing 4% dextran sodium sulfate (DSS) on Day 0. DSS treatment was continued until Day 6, when all mice were switched back to normal drinking water. IL-22 fusion proteins A2 and A8 were dosed by IP on Days −1, 1, 4, and 6. Body weights were measured and the results are shown in in FIG. 3, which indicates that fusion proteins A2 and A8 reduced the body weight drop resulting from DSS treatment. On Day 8, stool scores were measured for each mouse and the results are shown in FIG. 4, which indicates that fusion protein A8 at 56 μg reduced the fecal score relative to the DSS only control (t-test). On day 8, the mice were sacrificed, and their colons were excised and sent for histological assessment. The extent of goblet cell loss was quantified by a pathologist, and the results are shown in FIG. 5, which indicates that fusion proteins A2 and A8 significantly reduced the loss of colonic goblet cells (t-test).

Figure 6:
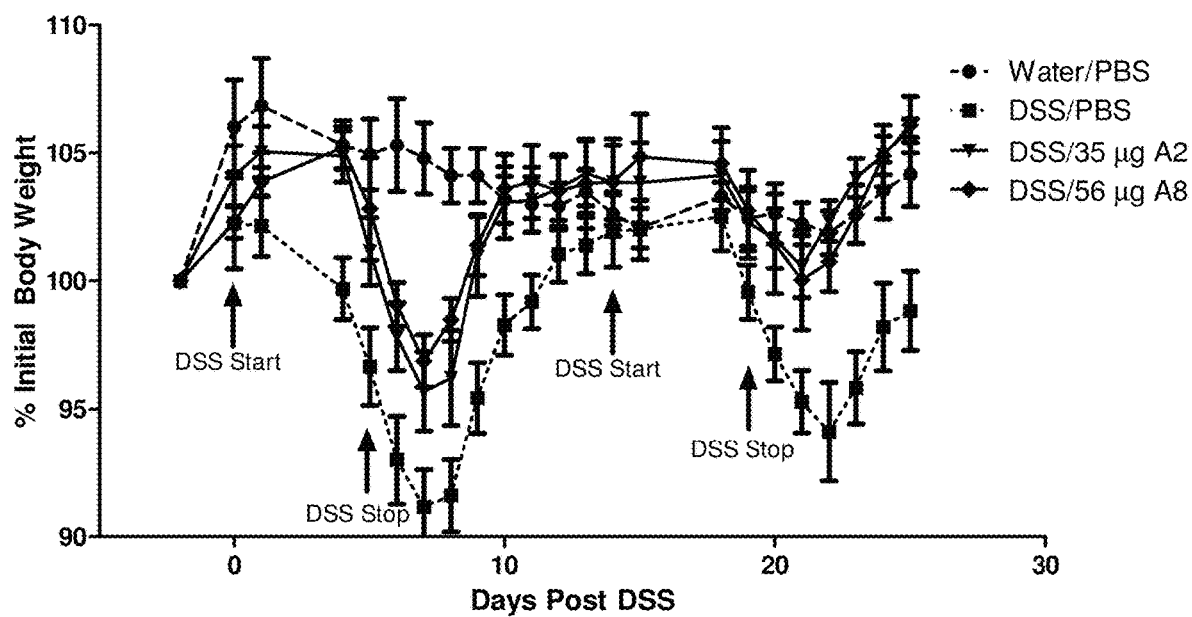
FIG. 6 shows the effect of IL-22 fusion protein A2 (SEQ ID NO: 58) at a dose of 35 μg and IL-22 fusion protein A8

Separate C57BL/6 mice (N=6) were given water or water containing 4% DSS on Day 0. DSS treatment was continued until Day 5, when all mice were switched back to normal drinking water. IL-22 fusion proteins A2 and A8 were dosed by IP on Days −1, 1, 4, and 6. A second round of DSS treatment was started on Day 14, with IL-22 fusion proteins A2 and A8 dosing on Days 13, 15, 18, and 20. Body weights were measured and the results are shown in FIG. 6, which indicates that fusion proteins A2 and A8 reduced the body weight drop resulting from DSS treatment. On Days 19 and 21, blood plasma was collected and analyzed for IL-6 by ELISA and the results are shown in FIG. 7, which indicates that fusion proteins A2 and A8 reduced plasma IL-6 levels induced by DSS treatment.

Sequences described herein are provided in the sequence table below.

SEQUENCE TABLE

| SEQ ID NO: | Description | Amino Acid Sequence |
|---|---|---|
| 1 | Human IL-22 | MAALQKSVSSFLMGTLATSCLLLLALLVQGGAAAPISS HCRLDKSNFQQPYITNRTFMLAKEASLADNNTDVRLIG EKLFHGVSMSERCYLMKQVLNFTLEEVLFPQSDRFQPY MQEVVPFLARLSNRLSTCHIEGDDLHIQRNVQKLKDTV KKLGESGEIKAIGELDLLFMSLRNACI |
| 2 | Mature human IL-22 | APISSHCRLDKSNFQQPYITNRTFMLAKEASLADNNTD VRLIGEKLFHGVSMSERCYLMKQVLNFTLEEVLFPQSD RFQPYMQEVVPFLARLSNRLSTCHIEGDDLHIQRNVQK LKDTVKKLGESGEIKAIGELDLLFMSLRNACI |
| 3 | Mouse IL-22 | MAVLQKSMSFSLMGTLAASCLLLIALWAQEANALPVN TRCKLEVSNFQQPYIVNRTFMLAKEASLADNNTDVRLI GEKLFRGVSAKDQCYLMKQVLNFTLEDVLLPQSDRFQ PYMQEVVPFLTKLSNQLSSCHISGDDQNIQKNVRRLKE TVKKLGESGEIKAIGELDLLFMSLRNACV |
| 4 | Mature mouse IL-22 | LPVNTRCKLEVSNFQQPYIVNRTFMLAKEASLADNNTD VRLIGEKLFRGVSAKDQCYLMKQVLNFTLEDVLLPQSD RFQPYMQEVVPFLTKLSNQLSSCHISGDDQNIQKNVRR LKETVKKLGESGEIKAIGELDLLFMSLRNACV |
| 5 | GLP-2 | HADGSFSDEMNTILDNLAARDFINWLIQTKITD |
| 6 | Teduglutide | HGDGSFSDEMNTILDNLAARDFINWLIQTKITD |
| 7 | GLP-2 Mutein (A2X) | HXDGSFSDEMNTILDNLAARDFINWLIQTKITD (X is C, D, E, F, G, H, I, K, L, M, N, Q, R, S, T, V, W, or Y) |
| 8 | hIGF1 | MGKISSLPTQLFKCCFCDFLKVKMHTMSSSHLFYLALC LLTFTSSATAGPETLCGAELVDALQFVCGDRGFYFNKP TGYGSSSRRAPQTGIVDECCFRSCDLRRLEMYCAPLKP AKSARSVRAQRHTDMPKTQKYQPPSTNKNTKSQRRKG WPKTHPGGEQKEGTEASLQIRGKKKEQRREIGSRNAEC RGKKGK |
| 9 | Mecasermin | GPETLCGAELVDALQFVCGDRGFYFNKPTGYGSSSRRA PQTGIVDECCFRSCDLRRLEMYCAPLKPAKSA |
| 10 | Anti-HSA-1 CDR1 | GSTWSINT |
| 11 | Anti-HSA-1 CDR2 | ISSGGST |
| 12 | Anti-HSA-1 CDR3 | YAQSTWYPPS |
| 13 | Anti-HSA-1 FR1 | EVQLVESGGGLVQPGGSLRLSCAAS |
| 14 | Anti-HSA-1 FR2 | LAWYRQAPGKQRDLVAR |
| 15 | Anti-HSA-1 FR3 | YYADSVKGRFTISRDNSKNTLYLQMNSLRAEDTAVYY C |
| 16 | Anti-HSA-1 FR4 | WGQGTLVTVSS |
| 17 | Anti-HSA-1 | EVQLVESGGGLVQPGGSLRLSCAASGSTWSINTLAWYR QAPGKQRDLVARISSGGSTYYADSVKGRFTISRDNSKN TLYLQMNSLRAEDTAVYYCYAQSTWYPPSWGQGTLVT VSS |
| 18 | Anti-HSA-2 CDR1 | GFAFRGFG |

-continued

| SEQUENCE TABLE | | |
|---|---|---|
| SEQ ID NO: | Description | Amino Acid Sequence |
| 19 | Anti-HSA-2 CDR2 | INNGGSDT |
| 20 | Anti-HSA-2 CDR3 | AIGGPGASP |
| 21 | Anti-HSA-2 FR1 | QVQLVESGGGVVQPGGSLRLSCAAS |
| 22 | Anti-HSA-2 FR2 | MSWVRQAPGKGLEWVSS |
| 23 | Anti-HSA-2 FR4 | SGQGTQVTVSS |
| 24 | Anti-HSA-2 | QVQLVESGGGVVQPGGSLRLSCAASGFAFRGFGMSWV RQAPGKGLEWVSSINNGGSDTYYADSVKGRFTISRDNS KNTLYLQMNSLRAEDTAVYYCAIGGPGASPSGQGTQV TVSS |
| 25 | (GSG)2 Linker | GSGGSG |
| 26 | (GSG)3 Linker | GSGGSGGSG |
| 27 | (GSG)4 Linker | GSGGSGGSGGSG |
| 28 | G3S Linker | GGGS |
| 29 | (G3S)2 Linker | GGGSGGGS |
| 30 | (G3S)3 Linker | GGGSGGGSGGGS |
| 31 | (G3S)4 Linker | GGGSGGGSGGGSGGGS |
| 32 | G4S Linker | GGGGS |
| 33 | (G4S)2 Linker | GGGGSGGGGS |
| 34 | (G4S)3 Linker | GGGGSGGGGSGGGGS |
| 35 | (G4S)4 Linker | GGGGSGGGGSGGGGSGGGGS |
| 36 | SGSG Linker | SGSG |
| 37 | S(GSG)2 Linker | SGSGGSG |
| 38 | S(GSG)3 Linker | SGSGGSGGSG |
| 39 | S(GSG)4 Linker | SGSGGSGGSGGSG |
| 40 | SG3S Linker | SGGGS |
| 41 | S(G3S)2 Linker | SGGGSGGGS |
| 42 | S(G3S)3 Linker | SGGGSGGGSGGGS |
| 43 | S(G3S)4 Linker | SGGGSGGGSGGGSGGGS |
| 44 | SG4S Linker | SGGGGS |
| 45 | S(G4S)2 Linker | SGGGGSGGGGS |
| 46 | S(G4S)3 Linker | SGGGGSGGGGSGGGGS |
| 47 | S(G4S)4 Linker | SGGGGSGGGGSGGGGSGGGGS |
| 48 | EAAAK Linker | EAAAK |
| 49 | (EAAAK)2 Linker | EAAAKEAAAK |
| 50 | (EAAAK)3 Linker | EAAAKEAAAKEAAAK |
| 51 | (EAAAK)4 Linker | EAAAKEAAAKEAAAKEAAAK |
| 52 | PAPAP Linker | PAPAP |
| 53 | (PAPAP)2 Linker | PAPAPPAPAP |
| 54 | (PAPAP)3 Linker | PAPAPPAPAPPAPAP |

| SEQ ID NO: | Description | Amino Acid Sequence |
|---|---|---|
| 55 | (PAPAP)4 Linker | PAPAPPAPAPPAPAPPAPAP |
| 56 | VLVH Linker | IKRTVAAP |
| 57 | hIL-22-anti-HSA A1 | APISSHCRLDKSNFQQPYITNRTFMLAKEASLADNNTD VRLIGEKLFHGVSMSERCYLMKQVLNFTLEEVLFPQSD RFQPYMQEVVPFLARLSNRLSTCHIEGDDLHIQRNVQK LKDTVKKLGESGEIKAIGELDLLFMSLRNACISGGGGSG GGGSGGGGSEVQLVESGGGLVQPGGSLRLSCAASGST WSINTLAWYRQAPGKQRDLVARISSGGSTYYADSVKG RFTISRDNSKNTLYLQMNSLRAEDTAVYYCYAQSTWY PPSWGQGTLVTVSS |
| 58 | mIL-22-anti-HSA A2 | LPVNTRCKLEVSNFQQPYIVNRTFMLAKEASLADNNTD VRLIGEKLFRGVSAKDQCYLMKQVLNFTLEDVLLPQSD RFQPYMQEVVPFLTKLSNQLSSCHISGDDQNIQKNVRR LKETVKKLGESGEIKAIGELDLLFMSLRNACVSGGGGS GGGGSGGGGSEVQLVESGGGLVQPGGSLRLSCAASGST WSINTLAWYRQAPGKQRDLVARISSGGSTYYADSVKG RFTISRDNSKNTLYLQMNSLRAEDTAVYYCYAQSTWY PPSWGQGTLVTVSS |
| 59 | Anti-HSA-mIL-22 A3 | QVQLVESGGGVVQPGGSLRLSCAASGFAFRGFGMSWV RQAPGKGLEWVSSINNGGSDTYYADSVKGRFTISRDNS KNTLYLQMNSLRAEDTAVYYCAIGGPGASPSGQGTQV TVSSGGGGSGGGGSGGGGSGGGGSLPVNTRCKLEVSNFQQPY IVNRTFMLAKEASLADNNTDVRLIGEKLFRGVSAKDQC YLMKQVLNFTLEDVLLPQSDRFQPYMQEVVPFLTKLSN QLSSCHISGDDQNIQKNVRRLKETVKKLGESGEIKAIGE LDLLFMSLRNACV |
| 60 | mIL-22-anti-HSA A4 | LPVNTRCKLEVSNFQQPYIVNRTFMLAKEASLADNNTD VRLIGEKLFRGVSAKDQCYLMKQVLNFTLEDVLLPQSD RFQPYMQEVVPFLTKLSNQLSSCHISGDDQNIQKNVRR LKETVKKLGESGEIKAIGELDLLFMSLRNACVSGGGGS GGGGSGGGGSQVQLVESGGGVVQPGGSLRLSCAASGF AFRGFGMSWVRQAPGKGLEWVSSINNGGSDTYYADSV KGRFTISRDNSKNTLYLQMNSLRAEDTAVYYCAIGGPG ASPSGQGTQVTVSS |
| 61 | hIL-22-anti-HSA A5 | APISSHCRLDKSNFQQPYITNRTFMLAKEASLADNNTD VRLIGEKLFHGVSMSERCYLMKQVLNFTLEEVLFPQSD RFQPYMQEVVPFLARLSNRLSTCHIEGDDLHIQRNVQK LKDTVKKLGESGEIKAIGELDLLFMSLRNACISGGGGSG GGGSGGGGSQVQLVESGGGVVQPGGSLRLSCAASGFA FRGFGMSWVRQAPGKGLEWVSSINNGGSDTYYADSVK GRFTISRDNSKNTLYLQMNSLRAEDTAVYYCAIGGPGA SPSGQGTQVTVSS |
| 62 | Anti-HSA-hIL-22 A6 | QVQLVESGGGVVQPGGSLRLSCAASGFAFRGFGMSWV RQAPGKGLEWVSSINNGGSDTYYADSVKGRFTISRDNS KNTLYLQMNSLRAEDTAVYYCAIGGPGASPSGQGTQV TVSSGGGSGGGSGGGSGGGSAPISSHCRLDKSNFQQPYI TNRTFMLAKEASLADNNTDVRLIGEKLFHGVSMSERCY LMKQVLNFTLEEVLFPQSDRFQPYMQEVVPFLARLSNR LSTCHIEGDDLHIQRNVQKLKDTVKKLGESGEIKAIGEL DLLFMSLRNACI |
| 63 | Anti-HSA-hIL-22 A7 | EVQLVESGGGLVQPGGSLRLSCAASGTWSINTLAWYR QAPGKQRDLVARISSGGSTYYADSVKGRFTISRDNSKN TLYLQMNSLRAEDTAVYYCYAQSTWYPPSWGQGTLVT VSSGGGSGGGSGGGSGGGSAPISSHCRLDKSNFQQPYIT NRTFMLAKEASLADNNTDVRLIGEKLFHGVSMSERCYL MKQVLNFTLEEVLFPQSDRFQPYMQEVVPFLARLSNRL STCHIEGDDLHIQRNVQKLKDTVKKLGESGEIKAIGELD LLFMSLRNACI |
| 64 | mIL-22-anti-HSA-mIL-22 A8 | LPVNTRCKLEVSNFQQPYIVNRTFMLAKEASLADNNTD VRLIGEKLFRGVSAKDQCYLMKQVLNFTLEDVLLPQSD RFQPYMQEVVPFLTKLSNQLSSCHISGDDQNIQKNVRR LKETVKKLGESGEIKAIGELDLLFMSLRNACVSGGGGS GGGGSGGGGSEVQLVESGGGLVQPGGSLRLSCAASGST WSINTLAWYRQAPGKQRDLVARISSGGSTYYADSVKG RFTISRDNSKNTLYLQMNSLRAEDTAVYYCYAQSTWY |

| SEQ ID NO: | Description | Amino Acid Sequence |
|---|---|---|
| | | PPSWGQGTLVTVSSGGGSGGGSGGGSGGGSLPVNTRC KLEVSNFQQPYIVNRTFMLAKEASLADNNTDVRLIGEK LFRGVSAKDQCYLMKQVLNFTLEDVLLPQSDRFQPYM QEVVPFLTKLSNQLSSCHISGDDQNIQKNVRRLKETVK KLGESGEIKAIGELDLLFMSLRNACV |
| 65 | mIL-22-anti-HSA mIL-22 A9 | LPVNTRCKLEVSNFQQPYIVNRTFMLAKEASLADNNTD VRLIGEKLFRGVSAKDQCYLMKQVLNFTLEDVLLPQSD RFQPYMQEVVPFLTKLSNQLSSCHISGDDQNIQKNVRR LKETVKKLGESGEIKAIGELDLLFMSLRNACVSGGGGS GGGGSGGGGSQVQLVESGGGVVQPGGSLRLSCAASGF AFRGFGMSWVRQAPGKGLEWVSSINNGGSDTYYADSV KGRFTISRDNSKNTLYLQMNSLRAEDTAVYYCAIGGPG ASPSGQGTQVTVSSGGGSGGGSGGGSGGGSLPVNTRCK LEVSNFQQPYIVNRTFMLAKEASLADNNTDVRLIGEKL FRGVSAKDQCYLMKQVLNFTLEDVLLPQSDRFQPYMQ EVVPFLTKLSNQLSSCHISGDDQNIQKNVRRLKETVKKL GESGEIKAIGELDLLFMSLRNACV |
| 66 | mIL-22-mIL-22-anti-HSA A10 | LPVNTRCKLEVSNFQQPYIVNRTFMLAKEASLADNNTD VRLIGEKLFRGVSAKDQCYLMKQVLNFTLEDVLLPQSD RFQPYMQEVVPFLTKLSNQLSSCHISGDDQNIQKNVRR LKETVKKLGESGEIKAIGELDLLFMSLRNACVSGGGGS GGGGSGGGGSLPVNTRCKLEVSNFQQPYIVNRTFMLAK EASLADNNTDVRLIGEKLFRGVSAKDQCYLMKQVLNF TLEDVLLPQSDRFQPYMQEVVPFLTKLSNQLSSCHISGD DQNIQKNVRRLKETVKKLGESGEIKAIGELDLLFMSLRN ACVGGGSGGGSGGGSGGGSEVQLVESGGGLVQPGGSL RLSCAASGSTWSINTLAWYRQAPGKQRDLVARISSGGS TYYADSVKGRFTISRDNSKNTLYLQMNSLRAEDTAVY YCYAQSTWYPPSWGQGTLVTVSS |
| 67 | hIL-22-hIL-22-anti-HSA A11 | APISSHCRLDKSNFQQPYITNRTFMLAKEASLADNNTD VRLIGEKLFHGVSMSERCYLMKQVLNFTLEEVLFPQSD RFQPYMQEVVPFLARLSNRLSTCHIEGDDLHIQRNVQK LKDTVKKLGESGEIKAIGELDLLFMSLRNACISGGGGSG GGGSGGGGSAPISSHCRLDKSNFQQPYITNRTFMLAKE ASLADNNTDVRLIGEKLFHGVSMSERCYLMKQVLNFT LEEVLFPQSDRFQPYMQEVVPFLARLSNRLSTCHIEGDD LHIQRNVQKLKDTVKKLGESGEIKAIGELDLLFMSLRN ACIGGGSGGGSGGGSGGGSEVQLVESGGGLVQPGGSLR LSCAASGSTWSINTLAWYRQAPGKQRDLVARISSGGST YYADSVKGRFTISRDNSKNTLYLQMNSLRAEDTAVYY CYAQSTWYPPSWGQGTLVTVSS |
| 68 | hIL-22-anti-HSA-hIL-22 A12 | APISSHCRLDKSNFQQPYITNRTFMLAKEASLADNNTD VRLIGEKLFHGVSMSERCYLMKQVLNFTLEEVLFPQSD RFQPYMQEVVPFLARLSNRLSTCHIEGDDLHIQRNVQK LKDTVKKLGESGEIKAIGELDLLFMSLRNACISGGGGSG GGGSGGGGSEVQLVESGGGLVQPGGSLRLSCAASGST WSINTLAWYRQAPGKQRDLVARISSGGSTYYADSVKG RFTISRDNSKNTLYLQMNSLRAEDTAVYYCYAQSTWY PPSWGQGTLVTVSSGGGSGGGSGGGSGGGSAPISSHCR LDKSNFQQPYITNRTFMLAKEASLADNNTDVRLIGEKL FHGVSMSERCYLMKQVLNFTLEEVLFPQSDRFQPYMQ EVVPFLARLSNRLSTCHIEGDDLHIQRNVQKLKDTVKK LGESGEIKAIGELDLLFMSLRNACI |
| 69 | Anti-HSA-hIL-22-hIL-22 A13 | QVQLVESGGGVVQPGGSLRLSCAASGFAFRGFGMSWV RQAPGKGLEWVSSINNGGSDTYYADSVKGRFTISRDNS KNTLYLQMNSLRAEDTAVYYCAIGGPGASPSGQGTQV TVSSGGGSGGGSGGGSGGGSAPISSHCRLDKSNFQQPYI TNRTFMLAKEASLADNNTDVRLIGEKLFHGVSMSERCY LMKQVLNFTLEEVLFPQSDRFQPYMQEVVPFLARLSNR LSTCHIEGDDLHIQRNVQKLKDTVKKLGESGEIKAIGEL DLLFMSLRNACISGGGGSGGGGSGGGGSAPISSHCRLD KSNFQQPYITNRTFMLAKEASLADNNTDVRLIGEKLFH GVSMSERCYLMKQVLNFTLEEVLFPQSDRFQPYMQEV VPFLARLSNRLSTCHIEGDDLHIQRNVQKLKDTVKKLG ESGEIKAIGELDLLFMSLRNACI |
| 70 | hIL-22-anti-HSA-hIL-22 A14 | APISSHCRLDKSNFQQPYITNRTFMLAKEASLADNNTD VRLIGEKLFHGVSMSERCYLMKQVLNFTLEEVLFPQSD RFQPYMQEVVPFLARLSNRLSTCHIEGDDLHIQRNVQK LKDTVKKLGESGEIKAIGELDLLFMSLRNACISGGGGSG |

SEQUENCE TABLE

| SEQ ID NO: | Description | Amino Acid Sequence |
|---|---|---|
| | | GGGSGGGGSQVQLVESGGGVVQPGGSLRLSCAASGFA FRGFGMSWVRQAPGKGLEWVSSINNGGSDTYYADSVK GRFTISRDNSKNTLYLQMNSLRAEDTAVYYCAIGGPGA SPSGQGTQVTVSSGGGSGGGSGGGSGGGSAPISSHCRL DKSNFQQPYITNRTFMLAKEASLADNNTDVRLIGEKLF HGVSMSERCYLMKQVLNFTLEEVLFPQSDRFQPYMQE VVPFLARLSNRLSTCHIEGDDLHIQRNVQKLKDTVKKL GESGEIKAIGELDLLFMSLRNACI |
| 71 | GLP-2-mIL-22-anti-HSA A15 | HGDGSFSDEMNTILDNLAARDFINWLIQTKITDGSGGSG GSGGSGLPVNTRCKLEVSNFQQPYIVNRTFMLAKEASL ADNNTDVRLIGEKLFRGVSAKDQCYLMKQVLNFTLED VLLPQSDRFQPYMQEVVPFLTKLSNQLSSCHISGDDQNI QKNVRRLKETVKKLGESGEIKAIGELDLLFMSLRNACV SGGGGSGGGGSGGGGSEVQLVESGGGLVQPGGSLRLS CAASGSTWSINTLAWYRQAPGKQRDLVARISSGGSTYY ADSVKGRFTISRDNSKNTLYLQMNSLRAEDTAVYYCY AQSTWYPPSWGQGTLVTVSS |
| 72 | GLP-2-anti-HSA-hIL-22 A16 | HGDGSFSDEMNTILDNLAARDFINWLIQTKITDGSGGSG GSGGSGEVQLVESGGGLVQPGGSLRLSCAASGSTWSIN TLAWYRQAPGKQRDLVARISSGGSTYYADSVKGRFTIS RDNSKNTLYLQMNSLRAEDTAVYYCYAQSTWYPPSW GQGTLVTVSSGGGSGGGSGGGSGGGSAPISSHCRLDKS NFQQPYITNRTFMLAKEASLADNNTDVRLIGEKLFHGV SMSERCYLMKQVLNFTLEEVLFPQSDRFQPYMQEVVPF LARLSNRLSTCHIEGDDLHIQRNVQKLKDTVKKLGESG EIKAIGELDLLFMSLRNACI |
| 73 | hIL-22-anti-HSA-GLP-2 A17 | APISSHCRLDKSNFQQPYITNRTFMLAKEASLADNNTD VRLIGEKLFHGVSMSERCYLMKQVLNFTLEEVLFPQSD RFQPYMQEVVPFLARLSNRLSTCHIEGDDLHIQRNVQK LKDTVKKLGESGEIKAIGELDLLFMSLRNACIGSGGSGG SGGSGEVQLVESGGGLVQPGGSLRLSCAASGSTWSINT LAWYRQAPGKQRDLVARISSGGSTYYADSVKGRFTISR DNSKNTLYLQMNSLRAEDTAVYYCYAQSTWYPPSWG QGTLVTVSSGGGSGGGSGGGSGGGSHGDGSFSDEMNTI LDNLAARDFINWLIQTKITD |
| 74 | GLP-2-hIL-22-anti-HSA A18 | HGDGSFSDEMNTILDNLAARDFINWLIQTKITDGSGGSG GSGGSGAPISSHCRLDKSNFQQPYITNRTFMLAKEASLA DNNTDVRLIGEKLFHGVSMSERCYLMKQVLNFTLEEVL FPQSDRFQPYMQEVVPFLARLSNRLSTCHIEGDDLHIQR NVQKLKDTVKKLGESGEIKAIGELDLLFMSLRNACISGG GGSGGGGSGGGGSEVQLVESGGGLVQPGGSLRLSCAA SGSTWSINTLAWYRQAPGKQRDLVARISSGGSTYYADS VKGRFTISRDNSKNTLYLQMNSLRAEDTAVYYCYAQS TWYPPSWGQGTLVTVSS |
| 75 | Anti-HSA-mIL-22-GLP-2 A19 | QVQLVESGGGVVQPGGSLRLSCAASGFAFRGFGMSWV RQAPGKGLEWVSSINNGGSDTYYADSVKGRFTISRDNS KNTLYLQMNSLRAEDTAVYYCAIGGPGASPSGQGTQV TVS SGGGSGGGSGGGSGGGSLPVNTRCKLEVSNFQQPY IVNRTFMLAKEASLADNNTDVRLIGEKLFRGVSAKDQC YLMKQVLNFTLEDVLLPQSDRFQPYMQEVVPFLTKLSN QLSSCHISGDDQNIQKNVRRLKETVKKLGESGEIKAIGE LDLLFMSLRNACVGSGGSGGSGGSGHGDGSFSDEMNTI LDNLAARDFINWLIQTKITD |
| 76 | GLP-2-anti-HSA-hIL-22 A20 | HGDGSFSDEMNTILDNLAARDFINWLIQTKITDGSGGSG GSGGSGQVQLVESGGGVVQPGGSLRLSCAASGFAFRGF GMSWVRQAPGKGLEWVSSINNGGSDTYYADSVKGRFT ISRDNSKNTLYLQMNSLRAEDTAVYYCAIGGPGASPSG QGTQVTVSSGGGSGGGSGGGSGGGSAPISSHCRLDKSN FQQPYITNRTFMLAKEASLADNNTDVRLIGEKLFHGVS MSERCYLMKQVLNFTLEEVLFPQSDRFQPYMQEVVPFL ARLSNRLSTCHIEGDDLHIQRNVQKLKDTVKKLGESGEI KAIGELDLLFMSLRNACI |
| 77 | hIL-22-anti-HSA-GLP-2 A21 | APISSHCRLDKSNFQQPYITNRTFMLAKEASLADNNTD VRLIGEKLFHGVSMSERCYLMKQVLNFTLEEVLFPQSD RFQPYMQEVVPFLARLSNRLSTCHIEGDDLHIQRNVQK LKDTVKKLGESGEIKAIGELDLLFMSLRNACIGSGGSGG SGGSGQVQLVESGGGVVQPGGSLRLSCAASGFAFRGFG MSWVRQAPGKGLEWVSSINNGGSDTYYADSVKGRFTI |

| SEQ ID NO: | Description | Amino Acid Sequence |
|---|---|---|
| | | SRDNSKNTLYLQMNSLRAEDTAVYYCAIGGPGASPSGQ GTQVTVSSGGGSGGGSGGGSGGGSHGDGSFSDEMNTIL DNLAARDFINWLIQTKITD |
| 78 | Anti-HSA-hIL-22-GLP-2 A22 | QVQLVESGGGVVQPGGSLRLSCAASGFAFRGFGMSWV RQAPGKGLEWVSSINNGGSDTYYADSVKGRFTISRDNS KNTLYLQMNSLRAEDTAVYYCAIGGPGASPSGQGTQV TVSSGGGSGGGSGGGSGGGSAPISSHCRLDKSNFQQPYI TNRTFMLAKEASLADNNTDVRLIGEKLFHGVSMSERCY LMKQVLNFTLEEVLFPQSDRFQPYMQEVVPFLARLSNR LSTCHIEGDDLHIQRNVQKLKDTVKKLGESGEIKAIGEL DLLFMSLRNACIGSGGSGGSGGSGHGDGSFSDEMNTIL DNLAARDFINWLIQTKITD |
| 79 | IGF-1-mIL-22-anti-HSA A23 | GPETLCGAELVDALQFVCGDRGFYFNKPTGYGSSSRRA PQTGIVDECCFRSCDLRRLEMYCAPLKPAKSAGSGGSG GSGGSGLPVNTRCKLEVSNFQQPYIVNRTFMLAKEASL ADNNTDVRLIGEKLFRGVSAKDQCYLMKQVLNFTLED VLLPQSDRFQPYMQEVVPFLTKLSNQLSSCHISGDDQNI QKNVRRLKETVKKLGESGEIKAIGELDLLFMSLRNACV SGGGGSGGGGSGGGGSEVQLVESGGGLVQPGGSLRLS CAASGSTWSINTLAWYRQAPGKQRDLVARISSGGSTYY ADSVKGRFTISRDNSKNTLYLQMNSLRAEDTAVYYCY AQSTWYPPSWGQGTLVTVSS |
| 80 | IGF-1-anti-HSA-hIL-22 A24 | GPETLCGAELVDALQFVCGDRGFYFNKPTGYGSSSRRA PQTGIVDECCFRSCDLRRLEMYCAPLKPAKSAGSGGSG GSGEVQLVESGGGLVQPGGSLRLSCAASGSTWSINTLA WYRQAPGKQRDLVARISSGGSTYYADSVKGRFTISRDN SKNTLYLQMNSLRAEDTAVYYCYAQSTWYPPSWGQG TLVTVSSGGGSGGGSGGGSGGGSAPISSHCRLDKSNFQ QPYITNRTFMLAKEASLADNNTDVRLIGEKLFHGVSMS ERCYLMKQVLNFTLEEVLFPQSDRFQPYMQEVVPFLAR LSNRLSTCHIEGDDLHIQRNVQKLKDTVKKLGESGEIKA IGELDLLFMSLRNACI |
| 81 | hIL-22-anti-HSA IGF-1- A25 | APISSHCRLDKSNFQQPYITNRTFMLAKEASLADNNTD VRLIGEKLFHGVSMSERCYLMKQVLNFTLEEVLFPQSD RFQPYMQEVVPFLARLSNRLSTCHIEGDDLHIQRNVQK LKDTVKKLGESGEIKAIGELDLLFMSLRNACIGSGGSGG SGEVQLVESGGGLVQPGGSLRLSCAASGSTWSINTLAW YRQAPGKQRDLVARISSGGSTYYADSVKGRFTISRDNS KNTLYLQMNSLRAEDTAVYYCYAQSTWYPPSWGQGT LVTVSSGGGSGGGSGGGSGGGSGPETLCGAELVDALQF VCGDRGFYFNKPTGYGSSSRRAPQTGIVDECCFRSCDL RRLEMYCAPLKPAKSA |
| 82 | IGF-1-hIL-22-anti-HSA A26 | GPETLCGAELVDALQFVCGDRGFYFNKPTGYGSSSRRA PQTGIVDECCFRSCDLRRLEMYCAPLKPAKSAGSGGSG GSGGSGAPISSHCRLDKSNFQQPYITNRTFMLAKEASLA NTDVRLIGEKLFHGVSMSERCYLMKQVLNFTLEEVL FPQSDRFQPYMQEVVPFLARLSNRLSTCHIEGDDLHIQR NVQKLKDTVKKLGESGEIKAIGELDLLFMSLRNACISGG GGSGGGGSEVQLVESGGGLVQPGGSLRLSCAA SGSTWSINTLAWYRQAPGKQRDLVARISSGGSTYYADS VKGRFTISRDNSKNTLYLQMNSLRAEDTAVYYCYAQS TWYPPSWGQGTLVTVSS |
| 83 | Anti-HSA-mIL-22-IGF-1 A27 | QVQLVESGGGVVQPGGSLRLSCAASGFAFRGFGMSWV RQAPGKGLEWVSSINNGGSDTYYADSVKGRFTISRDNS KNTLYLQMNSLRAEDTAVYYCAIGGPGASPSGQGTQV TVSSGGGSGGGSGGGSGGGSLPVNTRCKLEVSNFQQPY IVNRTFMLAKEASLADNNTDVRLIGEKLFRGVSAKDQC YLMKQVLNFTLEDVLLPQSDRFQPYMQEVVPFLTKLSN QLSSCHISGDDQNIQKNVRRLKETVKKLGESGEIKAIGE LDLLFMSLRNACVGSGGSGGSGGSGGPETLCGAELVD ALQFVCGDRGFYFNKPTGYGSSSRRAPQTGIVDECCFR SCDLRRLEMYCAPLKPAKSA |
| 84 | IGF-1-anti-HSA-hIL-22 A28 | GPETLCGAELVDALQFVCGDRGFYFNKPTGYGSSSRRA PQTGIVDECCFRSCDLRRLEMYCAPLKPAKSAGSGGSG GSGQVQLVESGGGVVQPGGSLRLSCAASGFAFRGFGM SWVRQAPGKGLEWVSSINNGGSDTYYADSVKGRFTISR DNSKNTLYLQMNSLRAEDTAVYYCAIGGPGASPSGQG TQVTVSSGGGSGGGSGGGSGGGSAPISSHCRLDKSNFQ |

SEQUENCE TABLE

| SEQ ID NO: | Description | Amino Acid Sequence |
|---|---|---|
| | | QPYITNRTFMLAKEASLADNNTDVRLIGEKLFHGVSMS<br>ERCYLMKQVLNFTLEEVLFPQSDRFQPYMQEVVPFLAR<br>LSNRLSTCHIEGDDLHIQRNVQKLKDTVKKLGESGEIKA<br>IGELDLLFMSLRNACI |
| 85 | hIL-22-anti-HSA-<br>IGF-1<br>A29 | APISSHCRLDKSNFQQPYITNRTFMLAKEASLADNNTD<br>VRLIGEKLFHGVSMSERCYLMKQVLNFTLEEVLFPQSD<br>RFQPYMQEVVPFLARLSNRLSTCHIEGDDLHIQRNVQK<br>LKDTVKKLGESGEIKAIGELDLLFMSLRNACIGSGGGS<br>SGGVQLVESGGGVVQPGGSLRLSCAASGFAFRGFGMS<br>WVRQAPGKGLEWVSSINNGGSDTYYADSVKGRFTISR<br>DNSKNTLYLQMNSLRAEDTAVYYCAIGGPGASPSGQG<br>TQVTVSSGGGSGGGSGGGSGGGSGPETLCGAELVDAL<br>QFVCGDRGFYFNKPTGYGSSSRRAPQTGIVDECCFRSC<br>DLRRLEMYCAPLKPAKSA |
| 86 | Anti-HSA-hIL-22-<br>IGF-1<br>A30 | QVQLVESGGGVVQPGGSLRLSCAASGFAFRGFGMSWV<br>RQAPGKGLEWVSSINNGGSDTYYADSVKGRFTISRDNS<br>KNTLYLQMNSLRAEDTAVYYCAIGGPGASPSGQGTQV<br>TVSSGGGSGGGSGGGSGGGSAPISSHCRLDKSNFQQPYI<br>TNRTFMLAKEASLADNNTDVRLIGEKLFHGVSMSERCY<br>LMKQVLNFTLEEVLFPQSDRFQPYMQEVVPFLARLSNR<br>LSTCHIEGDDLHIQRNVQKLKDTVKKLGESGEIKAIGEL<br>DLLFMSLRNACIGSGGSGGGSGGSGGPETLCGAELVDAL<br>QFVCGDRGFYFNKPTGYGSSSRRAPQTGIVDECCFRSC<br>DLRRLEMYCAPLKPAKSA |
| 87 | GLP-2-mIL-22-<br>anti-HSA-mIL-22<br>A31 | HGDGSFSDEMNTILDNLAARDFINWLIQTKITDGSGGS<br>GSGGSGLPVNTRCKLEVSNFQQPYIVNRTFMLAKEASL<br>ADNNTDVRLIGEKLFRGVSAKDQCYLMKQVLNFTLED<br>VLLPQSDRFQPYMQEVVPFLTKLSNQLSSCHISGDDQNI<br>QKNVRRLKETVKKLGESGEIKAIGELDLLFMSLRNACV<br>SGGGGSGGGGSGGGGSEVQLVESGGGLVQPGGSLRLS<br>CAASGSTWSINTLAWYRQAPGKQRDLVARISSGGSTYY<br>ADSVKGRFTISRDNSKNTLYLQMNSLRAEDTAVYYCY<br>AQSTWYPPSWGQGTLVTVSSGGGSGGGSGGGSGGGSL<br>PVNTRCKLEVSNFQQPYIVNRTFMLAKEASLADNNTDV<br>RLIGEKLFRGVSAKDQCYLMKQVLNFTLEDVLLPQSDR<br>FQPYMQEVVPFLTKLSNQLSSCHISGDDQNIQKNVRRL<br>KETVKKLGESGEIKAIGELDLLFMSLRNACV |
| 88 | GLP-2-hIL-22-<br>anti-HSA-hIL-22<br>A32 | HGDGSFSDEMNTILDNLAARDFINWLIQTKITDGSGGSG<br>GSGGSGAPISSHCRLDKSNFQQPYITNRTFMLAKEASLA<br>DNNTDVRLIGEKLFHGVSMSERCYLMKQVLNFTLEEVL<br>FPQSDRFQPYMQEVVPFLARLSNRLSTCHIEGDDLHIQR<br>NVQKLKDTVKKLGESGEIKAIGELDLLFMSLRNACISGG<br>GGSGGGGSGGGGSEVQLVESGGGLVQPGGSLRLSCAA<br>SGSTWSINTLAWYRQAPGKQRDLVARISSGGSTYYADS<br>VKGRFTISRDNSKNTLYLQMNSLRAEDTAVYYCYAQS<br>TWYPPSWGQGTLVTVSSGGGSGGGSGGGSGGGSAPISS<br>HCRLDKSNFQQPYITNRTFMLAKEASLADNNTDVRLIG<br>EKLFHGVSMSERCYLMKQVLNFTLEEVLFPQSDRFQPY<br>MQEVVPFLARLSNRLSTCHIEGDDLHIQRNVQKLKDTV<br>KKLGESGEIKAIGELDLLFMSLRNACI |
| 89 | mIL-22-anti-HSA-<br>mIL-22-GLP-2<br>A33 | LPVNTRCKLEVSNFQQPYIVNRTFMLAKEASLADNNTD<br>VRLIGEKLFRGVSAKDQCYLMKQVLNFTLEDVLLPQSD<br>RFQPYMQEVVPFLTKLSNQLSSCHISGDDQNIQKNVRR<br>LKETVKKLGESGEIKAIGELDLLFMSLRNACVSGGGGS<br>GGGGSGGGGSQVQLVESGGGVVQPGGSLRLSCAASGF<br>AFRGFGMSWVRQAPGKGLEWVSSINNGGSDTYYADSV<br>KGRFTISRDNSKNTLYLQMNSLRAEDTAVYYCAIGGPG<br>ASPSGQGTQVTVSSGGGSGGGSGGGSGGGSLPVNTRCK<br>LEVSNFQQPYIVNRTFMLAKEASLADNNTDVRLIGEKL<br>FRGVSAKDQCYLMKQVLNFTLEDVLLPQSDRFQPYMQ<br>EVVPFLTKLSNQLSSCHISGDDQNIQKNVRRLKETVKKL<br>GESGEIKAIGELDLLFMSLRNACVGSGGSGGGSGHG<br>DGSFSDEMNTILDNLAARDFINWLIQTKITD |
| 90 | hIL-22-anti-HSA-<br>hIL-22-GLP-2<br>A34 | APISSHCRLDKSNFQQPYITNRTFMLAKEASLADNNTD<br>VRLIGEKLFHGVSMSERCYLMKQVLNFTLEEVLFPQSD<br>RFQPYMQEVVPFLARLSNRLSTCHIEGDDLHIQRNVQK<br>LKDTVKKLGESGEIKAIGELDLLFMSLRNACISGGGGS<br>GGGSGGGGSQVQLVESGGGVVQPGGSLRLSCAASGFA<br>FRGFGMSWVRQAPGKGLEWVSSINNGGSDTYYADSVK |

| SEQ ID NO: | Description | Amino Acid Sequence |
|---|---|---|
| | | GRFTISRDNSKNTLYLQMNSLRAEDTAVYYCAIGGPGA SPSGQGTQVTVSSGGGSGGGSGGGSGGGSAPISSHCRL DKSNFQQPYITNRTFMLAKEASLADNNTDVRLIGEKLF HGVSMSERCYLMKQVLNFTLEEVLFPQSDRFQPYMQE VVPFLARLSNRLSTCHIEGDDLHIQRNVQKLKDTVKKL GESGEIKAIGELDLLFMSLRNACIGSGGSGGSGGSGHGD GSFSDEMNTILDNLAARDFINWLIQTKITD |
| 91 | IGF-1-mIL-22-anti-HSA-mIL-22 A35 | GPETLCGAELVDALQFVCGDRGFYFNKPTGYGSSSRRA PQTGIVDECCFRSCDLRRLEMYCAPLKPAKSAGSGGSG GSGGGSGLPVNTRCKLEVSNFQQPYIVNRTFMLAKEASL ADNNTDVRLIGEKLFRGVSAKDQCYLMKQVLNFTLED VLLPQSDRFQPYMQEVVPFLTKLSNQLSSCHISGDDQNI QKNVRRLKETVKKLGESGEIKAIGELDLLFMSLRNACV SGGGGSGGGGSGGGGSEVQLVESGGGLVQPGGSLRLS CAASGSTWSINTLAWYRQAPGKQRDLVARISSGGSTYY ADSVKGRFTISRDNSKNTLYLQMNSLRAEDTAVYYCY AQSTWYPPSWGQGTLVTVSSGGGSGGGSGGGSGGGSL PVNTRCKLEVSNFQQPYIVNRTFMLAKEASLADNNTDV RLIGEKLFRGVSAKDQCYLMKQVLNFTLEDVLLPQSDR FQPYMQEVVPFLTKLSNQLSSCHISGDDQNIQKNVRRL KETVKKLGESGEIKAIGELDLLFMSLRNACV |
| 92 | IGF-1-hIL-22-anti-HSA-hIL-22 A36 | GPETLCGAELVDALQFVCGDRGFYFNKPTGYGSSSRRA PQTGIVDECCFRSCDLRRLEMYCAPLKPAKSAGSGGSG GSGGGSGAPISSHCRLDKSNFQQPYITNRTFMLAKEASLA DNNTDVRLIGEKLFHGVSMSERCYLMKQVLNFTLEEVL FPQSDRFQPYMQEVVPFLARLSNRLSTCHIEGDDLHIQR NVQKLKDTVKKLGESGEIKAIGELDLLFMSLRNACISGG GGSGGGGSGGGGSEVQLVESGGGLVQPGGSLRLSCAA SGSTWSINTLAWYRQAPGKQRDLVARISSGGSTYYADS VKGRFTISRDNSKNTLYLQMNSLRAEDTAVYYCYAQS TWYPPSWGQGTLVTVSSGGGSGGGSGGGSGGGSAPISS HCRLDKSNFQQPYITNRTFMLAKEASLADNNTDVRLIG EKLFHGVSMSERCYLMKQVLNFTLEEVLFPQSDRFQPY MQEVVPFLARLSNRLSTCHIEGDDLHIQRNVQKLKDTV KKLGESGEIKAIGELDLLFMSLRNACI |
| 93 | mIL-22-anti-HSA mIL-22-IGF-1 A37 | LPVNTRCKLEVSNFQQPYIVNRTFMLAKEASLADNNTD VRLIGEKLFRGVSAKDQCYLMKQVLNFTLEDVLLPQSD RFQPYMQEVVPFLTKLSNQLSSCHISGDDQNIQKNVRR LKETVKKLGESGEIKAIGELDLLFMSLRNACVSGGGGS GGGGSGGGGSQVQLVESGGGVVQPGGSLRLSCAASGF AFRGFGMSWVRQAPGKGLEWVSSINNGGSDTYYADSV KGRFTISRDNSKNTLYLQMNSLRAEDTAVYYCAIGGPG ASPSGQGTQVTVSSGGGSGGGSGGGSGGGSLPVNTRCK LEVSNFQQPYIVNRTFMLAKEASLADNNTDVRLIGEKL FRGVSAKDQCYLMKQVLNFTLEDVLLPQSDRFQPYMQ EVVPFLTKLSNQLSSCHISGDDQNIQKNVRRLKETVKKL GESGEIKAIGELDLLFMSLRNACVSGGGSGGSGGSGGPE TLCGAELVDALQFVCGDRGFYFNKPTGYGSSSRRAPQT GIVDECCFRSCDLRRLEMYCAPLKPAKSA |
| 94 | hIL-22-anti-HSA-hIL-22-IGF-1 A38 | APISSHCRLDKSNFQQPYITNRTFMLAKEASLADNNTD VRLIGEKLFHGVSMSERCYLMKQVLNFTLEEVLFPQSD RFQPYMQEVVPFLARLSNRLSTCHIEGDDLHIQRNVQK LKDTVKKLGESGEIKAIGELDLLFMSLRNACISGGGGSG GGGSGGGGSQVQLVESGGGVVQPGGSLRLSCAASGFA FRGFGMSWVRQAPGKGLEWVSSINNGGSDTYYADSVK GRFTISRDNSKNTLYLQMNSLRAEDTAVYYCAIGGPGA SPSGQGTQVTVSSGGGSGGGSGGGSGGGSAPISSHCRL DKSNFQQPYITNRTFMLAKEASLADNNTDVRLIGEKLF HGVSMSERCYLMKQVLNFTLEEVLFPQSDRFQPYMQE VVPFLARLSNRLSTCHIEGDDLHIQRNVQKLKDTVKKL GESGEIKAIGELDLLFMSLRNACIGSGGSGGSGGSGGPE TLCGAELVDALQFVCGDRGFYFNKPTGYGSSSRRAPQT GIVDECCFRSCDLRRLEMYCAPLKPAKSA |
| 95 | mIL-22-hIgG1 Fc B1 | LPVNTRCKLEVSNFQQPYIVNRTFMLAKEASLADNNTD VRLIGEKLFRGVSAKDQCYLMKQVLNFTLEDVLLPQSD RFQPYMQEVVPFLTKLSNQLSSCHISGDDQNIQKNVRR LKETVKKLGESGEIKAIGELDLLFMSLRNACVARGPTIK PCPPCKCPAPNLLGGPSVFIFPPKIKDVLMISLSPIVTCVV VDVSEDDPDVQISWFVNNVEVHTAQTQTHREDYNSTL RVVSALPIQHQDWMSGKEFKCKVNNKDLPAPIERTISK |

| SEQUENCE TABLE | |
|---|---|
| SEQ ID NO: Description | Amino Acid Sequence |
| | PKGSVRAPQVYVLPPPEEEMTKKQVTLTCMVTDFMPE<br>DIYVEWTNNGKTELNYKNTEPVLDSDGSYFMYSKLRV<br>EKKNWVERNSYSCSVVHEGLHNHHTTKSFSRTPGK |

The examples set forth above are provided to give those of ordinary skill in the art with a complete disclosure and description of how to make and use the claimed embodiments and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A fusion protein comprising the amino acid sequence of Formula (I):

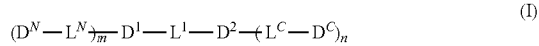   (I)

wherein:
- $D^1$ is an interleukin-22 domain and $D^2$ is an albumin binding domain; or $D^1$ is an albumin binding domain and $D^2$ is an interleukin-22 domain; wherein the albumin binding domain is a $V_HH$ single domain antibody comprising: (i) the CDR1 of SEQ ID NO: 10, the CDR2 of SEQ ID NO: 11, and the CDR3 of SEQ ID NO: 12; or (ii) the CDR1 of SEQ ID NO: 18, the CDR2 of SEQ ID NO: 19, and the CDR3 of SEQ ID NO: 20;
- $D^C$ and $D^N$ are each independently an interleukin-22 domain;
- $L^1$, $L^C$, and $L^N$ are each independently a bond or a peptide linker; and
- m and n are each independently an integer of 0 or 1; wherein $D^C$ and $D^N$ are at the C-terminus and N-terminus of the fusion protein, respectively.

2. The fusion protein of claim 1, comprising the amino acid sequence of Formula (II):

   (II)

wherein $D^1$ and $D^2$ are at the N-terminus and C-terminus of the fusion protein, respectively.

3. The fusion protein of claim 1, comprising the amino acid sequence of Formula (III):

   (III)

wherein $D^2$ and $D^N$ are at the C-terminus and N-terminus of the fusion protein, respectively.

4. The fusion protein of claim 3, wherein $D^1$ is the $V_HH$ single domain antibody and $D^2$ is the interleukin-22 domain.

5. The fusion protein of claim 4, wherein the $V_HH$ single domain antibody comprises the CDR1 of SEQ ID NO: 10, the CDR2 of SEQ ID NO: 11, and the CDR3 of SEQ ID NO: 12.

6. The fusion protein of claim 4, wherein the $V_HH$ single domain antibody comprises the CDR1 of SEQ ID NO: 18, the CDR2 of SEQ ID NO: 19, and the CDR3 of SEQ ID NO: 20.

7. The fusion protein of claim 4, wherein the $V_HH$ single domain antibody has the amino acid sequence of SEQ ID NO: 17 or 24.

8. The fusion protein of claim 4, wherein the $V_HH$ single domain antibody has the amino acid sequence of SEQ ID NO: 17.

9. The fusion protein of claim 4, wherein the $V_HH$ single domain antibody has the amino acid sequence of SEQ ID NO: 24.

10. The fusion protein of claim 4, wherein $D^2$ is the interleukin-22 domain comprising the amino acid sequence of a wild-type interleukin-22.

11. The fusion protein of claim 10, wherein $D^2$ is the interleukin-22 domain comprising the amino acid sequence of SEQ ID NO: 1, 2, 3, or 4.

12. The fusion protein of claim 3, wherein $L^1$ is the peptide linker of the amino acid sequence of GSG or any one of SEQ ID NOs: 25 to 56.

13. The fusion protein of claim 3, wherein $D^N$ is the interleukin-22 domain comprising the amino acid sequence of a wild-type interleukin-22.

14. The fusion protein of claim 3, wherein $D^N$ is the interleukin-22 domain comprising the amino acid sequence of SEQ ID NO: 1, 2, 3, or 4.

15. The fusion protein of claim 1, wherein $D^1$ is the interleukin-22 domain and $D^2$ is the $V_HH$ single domain antibody.

16. The fusion protein of claim 15, wherein $D^1$ is the interleukin-22 domain comprising the amino acid sequence of a wild-type interleukin-22.

17. The fusion protein of claim 16, wherein $D^1$ is the interleukin-22 domain comprising the amino acid sequence of SEQ ID NO: 1, 2, 3, or 4.

18. The fusion protein of claim 15, wherein the $V_HH$ single domain antibody comprises the CDR1 of SEQ ID NO: 10, the CDR2 of SEQ ID NO: 11, and the CDR3 of SEQ ID NO: 12.

19. The fusion protein of claim 15, wherein the $V_HH$ single domain antibody comprises the CDR1 of SEQ ID NO: 18, the CDR2 of SEQ ID NO: 19, and the CDR3 of SEQ ID NO: 20.

20. The fusion protein of claim 15, wherein the $V_HH$ single domain antibody has the amino acid sequence of SEQ ID NO: 17 or 24.

21. The fusion protein of claim 15, wherein the $V_HH$ single domain antibody has the amino acid sequence of SEQ ID NO: 17.

22. The fusion protein of claim 15, wherein the $V_HH$ single domain antibody has the amino acid sequence of SEQ ID NO: 24.

23. The fusion protein of claim 1, comprising the amino acid sequence of any one of SEQ ID NOs: 57 to 70.

24. The fusion protein of claim 1, comprising the amino acid sequence of SEQ ID NO: 57, 61, 62, 63, 67, 68, 69, or 70.

25. A pharmaceutical composition comprising the fusion protein of claim 1 and a pharmaceutically acceptable excipient.

* * * * *

SEQUENCE LISTING

```
<160> NUMBER OF SEQ ID NOS: 95

<210> SEQ ID NO 1
<211> LENGTH: 179
<212> TYPE: PRT
<213> ORGANISM: Homo sapiens

<400> SEQUENCE: 1

Met Ala Ala Leu Gln Lys Ser Val Ser Ser Phe Leu Met Gly Thr Leu
1               5                   10                  15

Ala Thr Ser Cys Leu Leu Leu Ala Leu Leu Val Gln Gly Gly Ala
                20                  25                  30

Ala Ala Pro Ile Ser Ser His Cys Arg Leu Asp Lys Ser Asn Phe Gln
            35                  40                  45

Gln Pro Tyr Ile Thr Asn Arg Thr Phe Met Leu Ala Lys Glu Ala Ser
        50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
                100                 105                 110

Pro Tyr Met Gln Glu Val Val Pro Phe Leu Ala Arg Leu Ser Asn Arg
            115                 120                 125

Leu Ser Thr Cys His Ile Glu Gly Asp Asp Leu His Ile Gln Arg Asn
        130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile

<210> SEQ ID NO 2
<211> LENGTH: 146
<212> TYPE: PRT
<213> ORGANISM: Homo sapiens

<400> SEQUENCE: 2

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
                20                  25                  30
```

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
            115                 120                 125

Lys Ala Ile Gly Glu Leu Asp Leu Leu Phe Met Ser Leu Arg Asn Ala
130                 135                 140

Cys Ile
145

<210> SEQ ID NO 3
<211> LENGTH: 179
<212> TYPE: PRT
<213> ORGANISM: Mus musculus

<400> SEQUENCE: 3

Met Ala Val Leu Gln Lys Ser Met Ser Phe Ser Leu Met Gly Thr Leu
1               5                   10                  15

Ala Ala Ser Cys Leu Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
        35                  40                  45

Gln Pro Tyr Ile Val Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Val Leu Leu Pro Gln Ser Asp Arg Phe Gln
            100                 105                 110

Pro Tyr Met Gln Glu Val Val Pro Phe Leu Thr Lys Leu Ser Asn Gln
            115                 120                 125

Leu Ser Ser Cys His Ile Ser Gly Asp Asp Gln Asn Ile Gln Lys Asn
130                 135                 140

Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val

<210> SEQ ID NO 4
<211> LENGTH: 146
<212> TYPE: PRT
<213> ORGANISM: Mus musculus

<400> SEQUENCE: 4

Leu Pro Val Asn Thr Arg Cys Lys Leu Glu Val Ser Asn Phe Gln Gln
1               5                   10                  15

```
Pro Tyr Ile Val Asn Arg Thr Phe Met Leu Ala Lys Glu Ala Ser Leu
            20                  25                  30

Ala Asp Asn Asn Thr Asp Val Arg Leu Ile Gly Glu Lys Leu Phe Arg
        35                  40                  45

Gly Val Ser Ala Lys Asp Gln Cys Tyr Leu Met Lys Gln Val Leu Asn
 50                  55                  60

Phe Thr Leu Glu Asp Val Leu Leu Pro Gln Ser Asp Arg Phe Gln Pro
 65                  70                  75                  80

Tyr Met Gln Glu Val Val Pro Phe Leu Thr Lys Leu Ser Asn Gln Leu
                85                  90                  95

Ser Ser Cys His Ile Ser Gly Asp Gln Asn Ile Gln Lys Asn Val
            100                 105                 110

Arg Arg Leu Lys Glu Thr Val Lys Lys Leu Gly Glu Ser Gly Glu Ile
            115                 120                 125

Lys Ala Ile Gly Glu Leu Asp Leu Leu Phe Met Ser Leu Arg Asn Ala
130                 135                 140

Cys Val
145

<210> SEQ ID NO 5
<211> LENGTH: 33
<212> TYPE: PRT
<213> ORGANISM: Homo sapiens

<400> SEQUENCE: 5

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 6
<211> LENGTH: 33
<212> TYPE: PRT
<213> ORGANISM: Homo sapiens

<400> SEQUENCE: 6

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 7
<211> LENGTH: 33
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa can be any naturally occurring amino acid
      other than Ala and Pro

<400> SEQUENCE: 7

His Xaa Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp
```

<210> SEQ ID NO 8
<211> LENGTH: 195
<212> TYPE: PRT
<213> ORGANISM: Homo sapiens

<400> SEQUENCE: 8

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Tyr Gln Pro Pro Ser Thr Asn Lys Asn Thr
    130                 135                 140

Lys Ser Gln Arg Arg Lys Gly Trp Pro Lys Thr His Pro Gly Gly Glu
145                 150                 155                 160

Gln Lys Glu Gly Thr Glu Ala Ser Leu Gln Ile Arg Gly Lys Lys Lys
                165                 170                 175

Glu Gln Arg Arg Glu Ile Gly Ser Arg Asn Ala Glu Cys Arg Gly Lys
            180                 185                 190

Lys Gly Lys
        195
```

<210> SEQ ID NO 9
<211> LENGTH: 70
<212> TYPE: PRT
<213> ORGANISM: Homo sapiens

<400> SEQUENCE: 9

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70
```

<210> SEQ ID NO 10
<211> LENGTH: 8
<212> TYPE: PRT
<213> ORGANISM: Artificial Sequence
<220> FEATURE:
<223> OTHER INFORMATION: Based on llima sequence

```
<400> SEQUENCE: 10

Gly Ser Thr Trp Ser Ile Asn Thr
1               5

<210> SEQ ID NO 11
<211> LENGTH: 7
<212> TYPE: PRT
<213> ORGANISM: Artificial Sequence
<220> FEATURE:
<223> OTHER INFORMATION: Based on llima sequence

<400> SEQUENCE: 11

Ile Ser Ser Gly Gly Ser Thr
1               5

<210> SEQ ID NO 12
<211> LENGTH: 10
<212> TYPE: PRT
<213> ORGANISM: Artificial Sequence
<220> FEATURE:
<223> OTHER INFORMATION: Based on llima sequence

<400> SEQUENCE: 12

Tyr Ala Gln Ser Thr Trp Tyr Pro Pro Ser
1               5                   10

<210> SEQ ID NO 13
<211> LENGTH: 25
<212> TYPE: PRT
<213> ORGANISM: Homo sapiens

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 14
<211> LENGTH: 17
<212> TYPE: PRT
<213> ORGANISM: Homo sapiens

<400> SEQUENCE: 14

Leu Ala Trp Tyr Arg Gln Ala Pro Gly Lys Gln Arg Asp Leu Val Ala
1               5                   10                  15

Arg

<210> SEQ ID NO 15
<211> LENGTH: 38
<212> TYPE: PRT
<213> ORGANISM: Homo sapiens

<400> SEQUENCE: 15

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
                35

<210> SEQ ID NO 16
<211> LENGTH: 11
<212> TYPE: PRT
```

```
<213> ORGANISM: Homo sapiens

<400> SEQUENCE: 16

Trp Gly Gln Gly Thr Leu Val Thr Val Ser Ser
1               5                   10

<210> SEQ ID NO 17
<211> LENGTH: 116
<212> TYPE: PRT
<213> ORGANISM: Artificial Sequence
<220> FEATURE:
<223> OTHER INFORMATION: Based on llima sequence

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Gln Ser Thr Trp Tyr Pro Pro Ser Trp Gly Gln Gly Thr Leu Val
            100                 105                 110

Thr Val Ser Ser
        115

<210> SEQ ID NO 18
<211> LENGTH: 8
<212> TYPE: PRT
<213> ORGANISM: Artificial Sequence
<220> FEATURE:
<223> OTHER INFORMATION: Based on llima sequence

<400> SEQUENCE: 18

Gly Phe Ala Phe Arg Gly Phe Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Based on llima sequence

<400> SEQUENCE: 19

Ile Asn Asn Gly Gly Ser Asp Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Based on llima sequence

<400> SEQUENCE: 20

Ala Ile Gly Gly Pro Gly Ala Ser Pro
1               5
```

```
<210> SEQ ID NO 21
<211> LENGTH: 25
<212> TYPE: PRT
<213> ORGANISM: Homo sapiens

<400> SEQUENCE: 21

Gln Val Gln Leu Val Glu Ser Gly Gly Gly Val Val Gln Pro Gly Gly
1               5                   10                  15

Ser Leu Arg Leu Ser Cys Ala Ala Ser
            20                  25

<210> SEQ ID NO 22
<211> LENGTH: 17
<212> TYPE: PRT
<213> ORGANISM: Homo sapiens

<400> SEQUENCE: 22

Met Ser Trp Val Arg Gln Ala Pro Gly Lys Gly Leu Glu Trp Val Ser
1               5                   10                  15

Ser

<210> SEQ ID NO 23
<211> LENGTH: 11
<212> TYPE: PRT
<213> ORGANISM: Homo sapiens

<400> SEQUENCE: 23

Ser Gly Gln Gly Thr Gln Val Thr Val Ser Ser
1               5                   10

<210> SEQ ID NO 24
<211> LENGTH: 116
<212> TYPE: PRT
<213> ORGANISM: Artificial Sequence
<220> FEATURE:
<223> OTHER INFORMATION: Based on llima sequence

<400> SEQUENCE: 24

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ala Phe Arg Gly Phe
            20                  25                  30

Gly Met Ser Trp Val Arg Gln Ala Pro Gly Lys Gly Leu Glu Trp Val
        35                  40                  45

Ser Ser Ile Asn Asn Gly Gly Ser Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gly Gly Pro Gly Ala Ser Pro Ser Gly Gln Gly Thr Gln Val
            100                 105                 110

Thr Val Ser Ser
        115

<210> SEQ ID NO 25
<211> LENGTH: 6
<212> TYPE: PRT
<213> ORGANISM: Artificial Sequence
<220> FEATURE:
```

```
<223> OTHER INFORMATION: Linker

<400> SEQUENCE: 25

Gly Ser Gly Gly Ser Gly
1               5

<210> SEQ ID NO 26
<211> LENGTH: 9
<212> TYPE: PRT
<213> ORGANISM: Artificial Sequence
<220> FEATURE:
<223> OTHER INFORMATION: Linker

<400> SEQUENCE: 26

Gly Ser Gly Gly Ser Gly Gly Ser Gly
1               5

<210> SEQ ID NO 27
<211> LENGTH: 12
<212> TYPE: PRT
<213> ORGANISM: Artificial Sequence
<220> FEATURE:
<223> OTHER INFORMATION: Linker

<400> SEQUENCE: 27

Gly Ser Gly Gly Ser Gly Gly Ser Gly Gly Ser Gly
1               5                   10

<210> SEQ ID NO 28
<211> LENGTH: 4
<212> TYPE: PRT
<213> ORGANISM: Artificial Sequence
<220> FEATURE:
<223> OTHER INFORMATION: Linker

<400> SEQUENCE: 28

Gly Gly Gly Ser
1

<210> SEQ ID NO 29
<211> LENGTH: 8
<212> TYPE: PRT
<213> ORGANISM: Artificial Sequence
<220> FEATURE:
<223> OTHER INFORMATION: Linker

<400> SEQUENCE: 29

Gly Gly Gly Ser Gly Gly Gly Ser
1               5

<210> SEQ ID NO 30
<211> LENGTH: 12
<212> TYPE: PRT
<213> ORGANISM: Artificial Sequence
<220> FEATURE:
<223> OTHER INFORMATION: Linker

<400> SEQUENCE: 30

Gly Gly Gly Ser Gly Gly Gly Ser Gly Gly Gly Ser
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Linker
```

```
<400> SEQUENCE: 31

Gly Gly Gly Ser Gly Gly Gly Ser Gly Gly Gly Ser Gly Gly Gly Ser
1               5                   10                  15

<210> SEQ ID NO 32
<211> LENGTH: 5
<212> TYPE: PRT
<213> ORGANISM: Artificial Sequence
<220> FEATURE:
<223> OTHER INFORMATION: Linker

<400> SEQUENCE: 32

Gly Gly Gly Gly Ser
1               5

<210> SEQ ID NO 33
<211> LENGTH: 10
<212> TYPE: PRT
<213> ORGANISM: Artificial Sequence
<220> FEATURE:
<223> OTHER INFORMATION: Linker

<400> SEQUENCE: 33

Gly Gly Gly Gly Ser Gly Gly Gly Gly Ser
1               5                   10

<210> SEQ ID NO 34
<211> LENGTH: 15
<212> TYPE: PRT
<213> ORGANISM: Artificial Sequence
<220> FEATURE:
<223> OTHER INFORMATION: Linker

<400> SEQUENCE: 34

Gly Gly Gly Gly Ser Gly Gly Gly Ser Gly Gly Gly Gly Ser
1               5                   10                  15

<210> SEQ ID NO 35
<211> LENGTH: 20
<212> TYPE: PRT
<213> ORGANISM: Artificial Sequence
<220> FEATURE:
<223> OTHER INFORMATION: Linker

<400> SEQUENCE: 35

Gly Gly Gly Gly Ser Gly Gly Gly Gly Ser Gly Gly Gly Gly Ser Gly
1               5                   10                  15

Gly Gly Gly Ser
            20

<210> SEQ ID NO 36
<211> LENGTH: 4
<212> TYPE: PRT
<213> ORGANISM: Artificial Sequence
<220> FEATURE:
<223> OTHER INFORMATION: Linker

<400> SEQUENCE: 36

Ser Gly Ser Gly
1

<210> SEQ ID NO 37
<211> LENGTH: 7
<212> TYPE: PRT
<213> ORGANISM: Artificial Sequence
```

```
<220> FEATURE:
<223> OTHER INFORMATION: Linker

<400> SEQUENCE: 37

Ser Gly Ser Gly Gly Ser Gly
1               5

<210> SEQ ID NO 38
<211> LENGTH: 10
<212> TYPE: PRT
<213> ORGANISM: Artificial Sequence
<220> FEATURE:
<223> OTHER INFORMATION: Linker

<400> SEQUENCE: 38

Ser Gly Ser Gly Gly Ser Gly Gly Ser Gly
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Linker

<400> SEQUENCE: 39

Ser Gly Ser Gly Gly Ser Gly Gly Ser Gly Gly Ser Gly
1               5                   10

<210> SEQ ID NO 40
<211> LENGTH: 5
<212> TYPE: PRT
<213> ORGANISM: Artificial Sequence
<220> FEATURE:
<223> OTHER INFORMATION: Linker

<400> SEQUENCE: 40

Ser Gly Gly Gly Ser
1               5

<210> SEQ ID NO 41
<211> LENGTH: 9
<212> TYPE: PRT
<213> ORGANISM: Artificial Sequence
<220> FEATURE:
<223> OTHER INFORMATION: Linker

<400> SEQUENCE: 41

Ser Gly Gly Gly Ser Gly Gly Gly Ser
1               5

<210> SEQ ID NO 42
<211> LENGTH: 13
<212> TYPE: PRT
<213> ORGANISM: Artificial Sequence
<220> FEATURE:
<223> OTHER INFORMATION: Linker

<400> SEQUENCE: 42

Ser Gly Gly Gly Ser Gly Gly Gly Ser Gly Gly Gly Ser
1               5                   10

<210> SEQ ID NO 43
<211> LENGTH: 17
<212> TYPE: PRT
<213> ORGANISM: Artificial Sequence
<220> FEATURE:
```

<223> OTHER INFORMATION: Linker

<400> SEQUENCE: 43

Ser Gly Gly Gly Ser Gly Gly Gly Ser Gly Gly Gly Ser Gly Gly Gly
1               5                   10                  15

Ser

<210> SEQ ID NO 44
<211> LENGTH: 6
<212> TYPE: PRT
<213> ORGANISM: Artificial Sequence
<220> FEATURE:
<223> OTHER INFORMATION: Linker

<400> SEQUENCE: 44

Ser Gly Gly Gly Gly Ser
1               5

<210> SEQ ID NO 45
<211> LENGTH: 11
<212> TYPE: PRT
<213> ORGANISM: Artificial Sequence
<220> FEATURE:
<223> OTHER INFORMATION: Linker

<400> SEQUENCE: 45

Ser Gly Gly Gly Gly Ser Gly Gly Gly Gly Ser
1               5                   10

<210> SEQ ID NO 46
<211> LENGTH: 16
<212> TYPE: PRT
<213> ORGANISM: Artificial Sequence
<220> FEATURE:
<223> OTHER INFORMATION: Linker

<400> SEQUENCE: 46

Ser Gly Gly Gly Gly Ser Gly Gly Gly Gly Ser Gly Gly Gly Gly Ser
1               5                   10                  15

<210> SEQ ID NO 47
<211> LENGTH: 21
<212> TYPE: PRT
<213> ORGANISM: Artificial Sequence
<220> FEATURE:
<223> OTHER INFORMATION: Linker

<400> SEQUENCE: 47

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 48
<211> LENGTH: 5
<212> TYPE: PRT
<213> ORGANISM: Artificial Sequence
<220> FEATURE:
<223> OTHER INFORMATION: Linker

<400> SEQUENCE: 48

Glu Ala Ala Ala Lys
1               5

<210> SEQ ID NO 49

```
<211> LENGTH: 10
<212> TYPE: PRT
<213> ORGANISM: Artificial Sequence
<220> FEATURE:
<223> OTHER INFORMATION: Linker

<400> SEQUENCE: 49

Glu Ala Ala Ala Lys Glu Ala Ala Ala Lys
1               5                   10

<210> SEQ ID NO 50
<211> LENGTH: 15
<212> TYPE: PRT
<213> ORGANISM: Artificial Sequence
<220> FEATURE:
<223> OTHER INFORMATION: Linker

<400> SEQUENCE: 50

Glu Ala Ala Ala Lys Glu Ala Ala Ala Lys Glu Ala Ala Ala Lys
1               5                   10                  15

<210> SEQ ID NO 51
<211> LENGTH: 20
<212> TYPE: PRT
<213> ORGANISM: Artificial Sequence
<220> FEATURE:
<223> OTHER INFORMATION: Linker

<400> SEQUENCE: 51

Glu Ala Ala Ala Lys Glu Ala Ala Ala Lys Glu Ala Ala Ala Lys Glu
1               5                   10                  15

Ala Ala Ala Lys
            20

<210> SEQ ID NO 52
<211> LENGTH: 5
<212> TYPE: PRT
<213> ORGANISM: Artificial Sequence
<220> FEATURE:
<223> OTHER INFORMATION: Linker

<400> SEQUENCE: 52

Pro Ala Pro Ala Pro
1               5

<210> SEQ ID NO 53
<211> LENGTH: 10
<212> TYPE: PRT
<213> ORGANISM: Artificial Sequence
<220> FEATURE:
<223> OTHER INFORMATION: Linker

<400> SEQUENCE: 53

Pro Ala Pro Ala Pro Pro Ala Pro Ala Pro
1               5                   10

<210> SEQ ID NO 54
<211> LENGTH: 15
<212> TYPE: PRT
<213> ORGANISM: Artificial Sequence
<220> FEATURE:
<223> OTHER INFORMATION: Linker

<400> SEQUENCE: 54

Pro Ala Pro Ala Pro Pro Ala Pro Ala Pro Pro Ala Pro Ala Pro
1               5                   10                  15
```

<210> SEQ ID NO 55
<211> LENGTH: 20
<212> TYPE: PRT
<213> ORGANISM: Artificial Sequence
<220> FEATURE:
<223> OTHER INFORMATION: Linker

<400> SEQUENCE: 55

Pro Ala Pro Ala Pro Ala Pro Ala Pro Ala Pro Ala Pro Ala Pro Pro
1               5                   10                  15

Ala Pro Ala Pro
            20

<210> SEQ ID NO 56
<211> LENGTH: 8
<212> TYPE: PRT
<213> ORGANISM: Artificial Sequence
<220> FEATURE:
<223> OTHER INFORMATION: Linker

<400> SEQUENCE: 56

Ile Lys Arg Thr Val Ala Ala Pro
1               5

<210> SEQ ID NO 57
<211> LENGTH: 278
<212> TYPE: PRT
<213> ORGANISM: Homo sapiens

<400> SEQUENCE: 57

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Ser Gly Gly Gly Ser Gly Gly Gly Ser Gly Gly Gly
145                 150                 155                 160

Gly Ser Glu Val Gln Leu Val Glu Ser Gly Gly Leu Val Gln Pro
                165                 170                 175

Gly Gly Ser Leu Arg Leu Ser Cys Ala Ala Ser Gly Ser Thr Trp Ser
            180                 185                 190

Ile Asn Thr Leu Ala Trp Tyr Arg Gln Ala Pro Gly Lys Gln Arg Asp
        195                 200                 205

Leu Val Ala Arg Ile Ser Ser Gly Gly Ser Thr Tyr Tyr Ala Asp Ser
    210                 215                 220

```
Val Lys Gly Arg Phe Thr Ile Ser Arg Asp Asn Ser Lys Asn Thr Leu
225                 230                 235                 240

Tyr Leu Gln Met Asn Ser Leu Arg Ala Glu Asp Thr Ala Val Tyr Tyr
                245                 250                 255

Cys Tyr Ala Gln Ser Thr Trp Tyr Pro Pro Ser Trp Gly Gln Gly Thr
            260                 265                 270

Leu Val Thr Val Ser Ser
            275

<210> SEQ ID NO 58
<211> LENGTH: 278
<212> TYPE: PRT
<213> ORGANISM: Mus musculus

<400> SEQUENCE: 58

Leu Pro Val Asn Thr Arg Cys Lys Leu Glu Val Ser Asn Phe Gln Gln
1               5                   10                  15

Pro Tyr Ile Val Asn Arg Thr Phe Met Leu Ala Lys Glu Ala Ser Leu
            20                  25                  30

Ala Asp Asn Asn Thr Asp Val Arg Leu Ile Gly Glu Lys Leu Phe Arg
        35                  40                  45

Gly Val Ser Ala Lys Asp Gln Cys Tyr Leu Met Lys Gln Val Leu Asn
    50                  55                  60

Phe Thr Leu Glu Asp Val Leu Leu Pro Gln Ser Asp Arg Phe Gln Pro
65                  70                  75                  80

Tyr Met Gln Glu Val Val Pro Phe Leu Thr Lys Leu Ser Asn Gln Leu
                85                  90                  95

Ser Ser Cys His Ile Ser Gly Asp Asp Gln Asn Ile Gln Lys Asn Val
            100                 105                 110

Arg Arg Leu Lys Glu Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Val Ser Gly Gly Gly Ser Gly Gly Gly Gly Ser Gly Gly Gly Gly
145                 150                 155                 160

Gly Ser Glu Val Gln Leu Val Glu Ser Gly Gly Gly Leu Val Gln Pro
                165                 170                 175

Gly Gly Ser Leu Arg Leu Ser Cys Ala Ala Ser Gly Ser Thr Trp Ser
            180                 185                 190

Ile Asn Thr Leu Ala Trp Tyr Arg Gln Ala Pro Gly Lys Gln Arg Asp
        195                 200                 205

Leu Val Ala Arg Ile Ser Ser Gly Gly Ser Thr Tyr Tyr Ala Asp Ser
    210                 215                 220

Val Lys Gly Arg Phe Thr Ile Ser Arg Asp Asn Ser Lys Asn Thr Leu
225                 230                 235                 240

Tyr Leu Gln Met Asn Ser Leu Arg Ala Glu Asp Thr Ala Val Tyr Tyr
                245                 250                 255

Cys Tyr Ala Gln Ser Thr Trp Tyr Pro Pro Ser Trp Gly Gln Gly Thr
            260                 265                 270

Leu Val Thr Val Ser Ser
            275

<210> SEQ ID NO 59
<211> LENGTH: 278
<212> TYPE: PRT
<213> ORGANISM: Mus musculus
```

<400> SEQUENCE: 59

Gln Val Gln Leu Val Glu Ser Gly Gly Val Val Gln Pro Gly Gly
1               5                   10                  15

Ser Leu Arg Leu Ser Cys Ala Ala Ser Gly Phe Ala Phe Arg Gly Phe
            20                  25                  30

Gly Met Ser Trp Val Arg Gln Ala Pro Gly Lys Gly Leu Glu Trp Val
        35                  40                  45

Ser Ser Ile Asn Asn Gly Gly Ser Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gly Gly Pro Gly Ala Ser Pro Ser Gly Gln Gly Thr Gln Val
            100                 105                 110

Thr Val Ser Ser Gly Gly Gly Ser Gly Gly Gly Ser Gly Gly Gly Ser
        115                 120                 125

Gly Gly Gly Ser Leu Pro Val Asn Thr Arg Cys Lys Leu Glu Val Ser
130                 135                 140

Asn Phe Gln Gln Pro Tyr Ile Val Asn Arg Thr Phe Met Leu Ala Lys
145                 150                 155                 160

Glu Ala Ser Leu Ala Asp Asn Asn Thr Asp Val Arg Leu Ile Gly Glu
                165                 170                 175

Lys Leu Phe Arg Gly Val Ser Ala Lys Asp Gln Cys Tyr Leu Met Lys
            180                 185                 190

Gln Val Leu Asn Phe Thr Leu Glu Asp Val Leu Leu Pro Gln Ser Asp
        195                 200                 205

Arg Phe Gln Pro Tyr Met Gln Glu Val Val Pro Phe Leu Thr Lys Leu
    210                 215                 220

Ser Asn Gln Leu Ser Ser Cys His Ile Ser Gly Asp Asp Gln Asn Ile
225                 230                 235                 240

Gln Lys Asn Val Arg Arg Leu Lys Glu Thr Val Lys Lys Leu Gly Glu
                245                 250                 255

Ser Gly Glu Ile Lys Ala Ile Gly Glu Leu Asp Leu Leu Phe Met Ser
            260                 265                 270

Leu Arg Asn Ala Cys Val
        275

<210> SEQ ID NO 60
<211> LENGTH: 278
<212> TYPE: PRT
<213> ORGANISM: Mus musculus

<400> SEQUENCE: 60

Leu Pro Val Asn Thr Arg Cys Lys Leu Glu Val Ser Asn Phe Gln Gln
1               5                   10                  15

Pro Tyr Ile Val Asn Arg Thr Phe Met Leu Ala Lys Glu Ala Ser Leu
            20                  25                  30

Ala Asp Asn Asn Thr Asp Val Arg Leu Ile Gly Glu Lys Leu Phe Arg
        35                  40                  45

Gly Val Ser Ala Lys Asp Gln Cys Tyr Leu Met Lys Gln Val Leu Asn
    50                  55                  60

Phe Thr Leu Glu Asp Val Leu Leu Pro Gln Ser Asp Arg Phe Gln Pro
65                  70                  75                  80

Tyr Met Gln Glu Val Val Pro Phe Leu Thr Lys Leu Ser Asn Gln Leu
                85                  90                  95

Ser Ser Cys His Ile Ser Gly Asp Asp Gln Asn Ile Gln Lys Asn Val
            100                 105                 110

Arg Arg Leu Lys Glu Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Val Ser Gly Gly Gly Ser Gly Gly Gly Ser Gly Gly
145                 150                 155                 160

Gly Ser Gln Val Gln Leu Val Glu Ser Gly Gly Val Val Gln Pro
                165                 170                 175

Gly Gly Ser Leu Arg Leu Ser Cys Ala Ala Ser Gly Phe Ala Phe Arg
        180                 185                 190

Gly Phe Gly Met Ser Trp Val Arg Gln Ala Pro Gly Lys Gly Leu Glu
        195                 200                 205

Trp Val Ser Ser Ile Asn Asn Gly Gly Ser Asp Thr Tyr Tyr Ala Asp
    210                 215                 220

Ser Val Lys Gly Arg Phe Thr Ile Ser Arg Asp Asn Ser Lys Asn Thr
225                 230                 235                 240

Leu Tyr Leu Gln Met Asn Ser Leu Arg Ala Glu Asp Thr Ala Val Tyr
                245                 250                 255

Tyr Cys Ala Ile Gly Gly Pro Gly Ala Ser Pro Ser Gly Gln Gly Thr
        260                 265                 270

Gln Val Thr Val Ser Ser
        275

<210> SEQ ID NO 61
<211> LENGTH: 278
<212> TYPE: PRT
<213> ORGANISM: Homo sapiens

<400> SEQUENCE: 61

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Ser Gly Gly Gly Gly Ser Gly Gly Gly Gly Ser Gly Gly Gly
145                 150                 155                 160

```
Gly Ser Gln Val Gln Leu Val Glu Ser Gly Gly Val Val Gln Pro
                165                 170                 175

Gly Gly Ser Leu Arg Leu Ser Cys Ala Ala Ser Gly Phe Ala Phe Arg
        180                 185                 190

Gly Phe Gly Met Ser Trp Val Arg Gln Ala Pro Gly Lys Gly Leu Glu
            195                 200                 205

Trp Val Ser Ser Ile Asn Asn Gly Gly Ser Asp Thr Tyr Tyr Ala Asp
    210                 215                 220

Ser Val Lys Gly Arg Phe Thr Ile Ser Arg Asp Asn Ser Lys Asn Thr
225                 230                 235                 240

Leu Tyr Leu Gln Met Asn Ser Leu Arg Ala Glu Asp Thr Ala Val Tyr
                245                 250                 255

Tyr Cys Ala Ile Gly Gly Pro Gly Ala Ser Pro Ser Gly Gln Gly Thr
            260                 265                 270

Gln Val Thr Val Ser Ser
            275
```

<210> SEQ ID NO 62
<211> LENGTH: 278
<212> TYPE: PRT
<213> ORGANISM: Homo sapiens

<400> SEQUENCE: 62

```
Gln Val Gln Leu Val Glu Ser Gly Gly Val Val Gln Pro Gly Gly
1               5                   10                  15

Ser Leu Arg Leu Ser Cys Ala Ala Ser Gly Phe Ala Phe Arg Gly Phe
                20                  25                  30

Gly Met Ser Trp Val Arg Gln Ala Pro Gly Lys Gly Leu Glu Trp Val
            35                  40                  45

Ser Ser Ile Asn Asn Gly Gly Ser Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gly Gly Pro Gly Ala Ser Pro Ser Gly Gln Gly Thr Gln Val
            100                 105                 110

Thr Val Ser Ser Gly Gly Ser Gly Gly Ser Gly Gly Ser
            115                 120                 125

Gly Gly Gly Ser Ala Pro Ile Ser Ser His Cys Arg Leu Asp Lys Ser
130                 135                 140

Asn Phe Gln Gln Pro Tyr Ile Thr Asn Arg Thr Phe Met Leu Ala Lys
145                 150                 155                 160

Glu Ala Ser Leu Ala Asp Asn Asn Thr Asp Val Arg Leu Ile Gly Glu
                165                 170                 175

Lys Leu Phe His Gly Val Ser Met Ser Glu Arg Cys Tyr Leu Met Lys
            180                 185                 190

Gln Val Leu Asn Phe Thr Leu Glu Glu Val Leu Phe Pro Gln Ser Asp
        195                 200                 205

Arg Phe Gln Pro Tyr Met Gln Glu Val Val Pro Phe Leu Ala Arg Leu
    210                 215                 220

Ser Asn Arg Leu Ser Thr Cys His Ile Glu Gly Asp Asp Leu His Ile
225                 230                 235                 240
```

```
Gln Arg Asn Val Gln Lys Leu Lys Asp Thr Val Lys Lys Leu Gly Glu
            245                 250                 255

Ser Gly Glu Ile Lys Ala Ile Gly Glu Leu Asp Leu Leu Phe Met Ser
            260                 265                 270

Leu Arg Asn Ala Cys Ile
            275

<210> SEQ ID NO 63
<211> LENGTH: 278
<212> TYPE: PRT
<213> ORGANISM: Homo sapiens

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Gln Ser Thr Trp Tyr Pro Pro Ser Trp Gly Gln Gly Thr Leu Val
            100                 105                 110

Thr Val Ser Ser Gly Gly Gly Gly Ser Gly Gly Gly Gly Ser Gly Gly Ser
            115                 120                 125

Gly Gly Gly Ser Ala Pro Ile Ser Ser His Cys Arg Leu Asp Lys Ser
130                 135                 140

Asn Phe Gln Gln Pro Tyr Ile Thr Asn Arg Thr Phe Met Leu Ala Lys
145                 150                 155                 160

Glu Ala Ser Leu Ala Asp Asn Asn Thr Asp Val Arg Leu Ile Gly Glu
                165                 170                 175

Lys Leu Phe His Gly Val Ser Met Ser Glu Arg Cys Tyr Leu Met Lys
            180                 185                 190

Gln Val Leu Asn Phe Thr Leu Glu Glu Val Leu Phe Pro Gln Ser Asp
        195                 200                 205

Arg Phe Gln Pro Tyr Met Gln Glu Val Val Pro Phe Leu Ala Arg Leu
    210                 215                 220

Ser Asn Arg Leu Ser Thr Cys His Ile Glu Gly Asp Asp Leu His Ile
225                 230                 235                 240

Gln Arg Asn Val Gln Lys Leu Lys Asp Thr Val Lys Lys Leu Gly Glu
                245                 250                 255

Ser Gly Glu Ile Lys Ala Ile Gly Glu Leu Asp Leu Leu Phe Met Ser
            260                 265                 270

Leu Arg Asn Ala Cys Ile
            275

<210> SEQ ID NO 64
<211> LENGTH: 440
<212> TYPE: PRT
<213> ORGANISM: Mus musculus
```

<400> SEQUENCE: 64

| | | | | | | | | | | | | | | |
|---|---|---|---|---|---|---|---|---|---|---|---|---|---|---|
|Leu|Pro|Val|Asn|Thr|Arg|Cys|Lys|Leu|Glu|Val|Ser|Asn|Phe|Gln|Gln|
|1| | | |5| | | | |10| | | | |15|
|Pro|Tyr|Ile|Val|Asn|Arg|Thr|Phe|Met|Leu|Ala|Lys|Glu|Ala|Ser|Leu|
| | | |20| | | | |25| | | | |30| | |
|Ala|Asp|Asn|Asn|Thr|Asp|Val|Arg|Leu|Ile|Gly|Glu|Lys|Leu|Phe|Arg|
| | |35| | | | |40| | | | |45| | | |
|Gly|Val|Ser|Ala|Lys|Asp|Gln|Cys|Tyr|Leu|Met|Lys|Gln|Val|Leu|Asn|
| |50| | | | |55| | | | |60| | | | |
|Phe|Thr|Leu|Glu|Asp|Val|Leu|Leu|Pro|Gln|Ser|Asp|Arg|Phe|Gln|Pro|
|65| | | |70| | | | |75| | | | |80| |
|Tyr|Met|Gln|Glu|Val|Val|Pro|Phe|Leu|Thr|Lys|Leu|Ser|Asn|Gln|Leu|
| | | | |85| | | | |90| | | | |95| |
|Ser|Ser|Cys|His|Ile|Ser|Gly|Asp|Asp|Gln|Asn|Ile|Gln|Lys|Asn|Val|
| | | |100| | | | |105| | | | |110| | |
|Arg|Arg|Leu|Lys|Glu|Thr|Val|Lys|Lys|Leu|Gly|Glu|Ser|Gly|Glu|Ile|
| | | |115| | | | |120| | | | |125| | |
|Lys|Ala|Ile|Gly|Glu|Leu|Asp|Leu|Leu|Phe|Met|Ser|Leu|Arg|Asn|Ala|
| | |130| | | | |135| | | | |140| | | |
|Cys|Val|Ser|Gly|Gly|Gly|Ser|Gly|Gly|Gly|Ser|Gly|Gly|Gly|Gly|
|145| | | |150| | | | |155| | | | |160|
|Gly|Ser|Glu|Val|Gln|Leu|Val|Glu|Ser|Gly|Gly|Leu|Val|Gln|Pro|
| | | | |165| | | | |170| | | | |175|
|Gly|Gly|Ser|Leu|Arg|Leu|Ser|Cys|Ala|Ala|Ser|Gly|Ser|Thr|Trp|Ser|
| | | |180| | | | |185| | | | |190| | |
|Ile|Asn|Thr|Leu|Ala|Trp|Tyr|Arg|Gln|Ala|Pro|Gly|Lys|Gln|Arg|Asp|
| | |195| | | | |200| | | | |205| | | |
|Leu|Val|Ala|Arg|Ile|Ser|Ser|Gly|Gly|Ser|Thr|Tyr|Tyr|Ala|Asp|Ser|
| |210| | | | |215| | | | |220| | | | |
|Val|Lys|Gly|Arg|Phe|Thr|Ile|Ser|Arg|Asp|Asn|Ser|Lys|Asn|Thr|Leu|
|225| | | |230| | | | |235| | | | |240| |
|Tyr|Leu|Gln|Met|Asn|Ser|Leu|Arg|Ala|Glu|Asp|Thr|Ala|Val|Tyr|Tyr|
| | | | |245| | | | |250| | | | |255| |
|Cys|Tyr|Ala|Gln|Ser|Thr|Trp|Tyr|Pro|Pro|Ser|Trp|Gly|Gln|Gly|Thr|
| | | |260| | | | |265| | | | |270| | |
|Leu|Val|Thr|Val|Ser|Ser|Gly|Gly|Gly|Ser|Gly|Gly|Gly|Ser|Gly|Gly|
| | | |275| | | | |280| | | | |285| | |
|Gly|Ser|Gly|Gly|Gly|Ser|Leu|Pro|Val|Asn|Thr|Arg|Cys|Lys|Leu|Glu|
| |290| | | | |295| | | | |300| | | | |
|Val|Ser|Asn|Phe|Gln|Gln|Pro|Tyr|Ile|Val|Asn|Arg|Thr|Phe|Met|Leu|
|305| | | |310| | | | |315| | | | |320| |
|Ala|Lys|Glu|Ala|Ser|Leu|Ala|Asp|Asn|Asn|Thr|Asp|Val|Arg|Leu|Ile|
| | | |325| | | | |330| | | | |335| | |
|Gly|Glu|Lys|Leu|Phe|Arg|Gly|Val|Ser|Ala|Lys|Asp|Gln|Cys|Tyr|Leu|
| | | |340| | | | |345| | | | |350| | |
|Met|Lys|Gln|Val|Leu|Asn|Phe|Thr|Leu|Glu|Asp|Val|Leu|Leu|Pro|Gln|
| | | |355| | | | |360| | | | |365| | |
|Ser|Asp|Arg|Phe|Gln|Pro|Tyr|Met|Gln|Glu|Val|Val|Pro|Phe|Leu|Thr|
| |370| | | | |375| | | | |380| | | | |
|Lys|Leu|Ser|Asn|Gln|Leu|Ser|Ser|Cys|His|Ile|Ser|Gly|Asp|Asp|Gln|
|385| | | |390| | | | |395| | | | |400|

```
Asn Ile Gln Lys Asn Val Arg Leu Lys Glu Thr Val Lys Lys Leu
            405                 410                 415

Gly Glu Ser Gly Glu Ile Lys Ala Ile Gly Glu Leu Asp Leu Phe
            420                 425                 430

Met Ser Leu Arg Asn Ala Cys Val
            435                 440

<210> SEQ ID NO 65
<211> LENGTH: 440
<212> TYPE: PRT
<213> ORGANISM: Mus musculus

<400> SEQUENCE: 65

Leu Pro Val Asn Thr Arg Cys Lys Leu Glu Val Ser Asn Phe Gln Gln
1               5                   10                  15

Pro Tyr Ile Val Asn Arg Thr Phe Met Leu Ala Lys Glu Ala Ser Leu
            20                  25                  30

Ala Asp Asn Asn Thr Asp Val Arg Leu Ile Gly Glu Lys Leu Phe Arg
            35                  40                  45

Gly Val Ser Ala Lys Asp Gln Cys Tyr Leu Met Lys Gln Val Leu Asn
50                  55                  60

Phe Thr Leu Glu Asp Val Leu Leu Pro Gln Ser Asp Arg Phe Gln Pro
65                  70                  75                  80

Tyr Met Gln Glu Val Val Pro Phe Leu Thr Lys Leu Ser Asn Gln Leu
            85                  90                  95

Ser Ser Cys His Ile Ser Gly Asp Asp Gln Asn Ile Gln Lys Asn Val
            100                 105                 110

Arg Arg Leu Lys Glu Thr Val Lys Lys Leu Gly Glu Ser Gly Glu Ile
            115                 120                 125

Lys Ala Ile Gly Glu Leu Asp Leu Leu Phe Met Ser Leu Arg Asn Ala
            130                 135                 140

Cys Val Ser Gly Gly Gly Gly Ser Gly Gly Gly Ser Gly Gly Gly
145                 150                 155                 160

Gly Ser Gln Val Gln Leu Val Glu Ser Gly Gly Val Val Gln Pro
            165                 170                 175

Gly Gly Ser Leu Arg Leu Ser Cys Ala Ala Ser Gly Phe Ala Phe Arg
            180                 185                 190

Gly Phe Gly Met Ser Trp Val Arg Gln Ala Pro Gly Lys Gly Leu Glu
            195                 200                 205

Trp Val Ser Ser Ile Asn Asn Gly Gly Ser Asp Thr Tyr Tyr Ala Asp
            210                 215                 220

Ser Val Lys Gly Arg Phe Thr Ile Ser Arg Asp Asn Ser Lys Asn Thr
225                 230                 235                 240

Leu Tyr Leu Gln Met Asn Ser Leu Arg Ala Glu Asp Thr Ala Val Tyr
            245                 250                 255

Tyr Cys Ala Ile Gly Gly Pro Gly Ala Ser Pro Ser Gly Gln Gly Thr
            260                 265                 270

Gln Val Thr Val Ser Ser Gly Gly Gly Gly Ser Gly Gly
            275                 280                 285

Gly Ser Gly Gly Gly Ser Leu Pro Val Asn Thr Arg Cys Lys Leu Glu
            290                 295                 300

Val Ser Asn Phe Gln Gln Pro Tyr Ile Val Asn Arg Thr Phe Met Leu
305                 310                 315                 320
```

```
Ala Lys Glu Ala Ser Leu Ala Asp Asn Asn Thr Asp Val Arg Leu Ile
            325                 330                 335

Gly Glu Lys Leu Phe Arg Gly Val Ser Ala Lys Asp Gln Cys Tyr Leu
            340                 345                 350

Met Lys Gln Val Leu Asn Phe Thr Leu Glu Asp Val Leu Leu Pro Gln
            355                 360                 365

Ser Asp Arg Phe Gln Pro Tyr Met Gln Glu Val Val Pro Phe Leu Thr
            370                 375                 380

Lys Leu Ser Asn Gln Leu Ser Ser Cys His Ile Ser Gly Asp Asp Gln
385                 390                 395                 400

Asn Ile Gln Lys Asn Val Arg Arg Leu Lys Glu Thr Val Lys Lys Leu
            405                 410                 415

Gly Glu Ser Gly Glu Ile Lys Ala Ile Gly Glu Leu Asp Leu Leu Phe
            420                 425                 430

Met Ser Leu Arg Asn Ala Cys Val
            435                 440

<210> SEQ ID NO 66
<211> LENGTH: 440
<212> TYPE: PRT
<213> ORGANISM: Mus musculus

<400> SEQUENCE: 66

Leu Pro Val Asn Thr Arg Cys Lys Leu Glu Val Ser Asn Phe Gln Gln
1               5                   10                  15

Pro Tyr Ile Val Asn Arg Thr Phe Met Leu Ala Lys Glu Ala Ser Leu
            20                  25                  30

Ala Asp Asn Asn Thr Asp Val Arg Leu Ile Gly Glu Lys Leu Phe Arg
            35                  40                  45

Gly Val Ser Ala Lys Asp Gln Cys Tyr Leu Met Lys Gln Val Leu Asn
        50                  55                  60

Phe Thr Leu Glu Asp Val Leu Leu Pro Gln Ser Asp Arg Phe Gln Pro
65                  70                  75                  80

Tyr Met Gln Glu Val Pro Phe Leu Thr Lys Leu Ser Asn Gln Leu
            85                  90                  95

Ser Ser Cys His Ile Ser Gly Asp Asp Gln Asn Ile Gln Lys Asn Val
            100                 105                 110

Arg Arg Leu Lys Glu Thr Val Lys Lys Leu Gly Glu Ser Gly Glu Ile
            115                 120                 125

Lys Ala Ile Gly Glu Leu Asp Leu Leu Phe Met Ser Leu Arg Asn Ala
            130                 135                 140

Cys Val Ser Gly Gly Gly Gly Ser Gly Gly Gly Ser Gly Gly Gly
145                 150                 155                 160

Gly Ser Leu Pro Val Asn Thr Arg Cys Lys Leu Glu Val Ser Asn Phe
            165                 170                 175

Gln Gln Pro Tyr Ile Val Asn Arg Thr Phe Met Leu Ala Lys Glu Ala
            180                 185                 190

Ser Leu Ala Asp Asn Asn Thr Asp Val Arg Leu Ile Gly Glu Lys Leu
            195                 200                 205

Phe Arg Gly Val Ser Ala Lys Asp Gln Cys Tyr Leu Met Lys Gln Val
            210                 215                 220

Leu Asn Phe Thr Leu Glu Asp Val Leu Leu Pro Gln Ser Asp Arg Phe
225                 230                 235                 240
```

-continued

Gln Pro Tyr Met Gln Glu Val Pro Phe Leu Thr Lys Leu Ser Asn
                245                 250                 255

Gln Leu Ser Ser Cys His Ile Ser Gly Asp Asp Gln Asn Ile Gln Lys
        260                 265                 270

Asn Val Arg Arg Leu Lys Glu Thr Val Lys Lys Leu Gly Glu Ser Gly
            275                 280                 285

Glu Ile Lys Ala Ile Gly Glu Leu Asp Leu Leu Phe Met Ser Leu Arg
290                 295                 300

Asn Ala Cys Val Gly Gly Ser Gly Gly Ser Gly Gly Gly Ser
305                 310                 315                 320

Gly Gly Gly Ser Glu Val Gln Leu Val Glu Ser Gly Gly Leu Val
            325                 330                 335

Gln Pro Gly Gly Ser Leu Arg Leu Ser Cys Ala Ala Ser Gly Ser Thr
            340                 345                 350

Trp Ser Ile Asn Thr Leu Ala Trp Tyr Arg Gln Ala Pro Gly Lys Gln
            355                 360                 365

Arg Asp Leu Val Ala Arg Ile Ser Ser Gly Gly Ser Thr Tyr Tyr Ala
        370                 375                 380

Asp Ser Val Lys Gly Arg Phe Thr Ile Ser Arg Asp Asn Ser Lys Asn
385                 390                 395                 400

Thr Leu Tyr Leu Gln Met Asn Ser Leu Arg Ala Glu Asp Thr Ala Val
            405                 410                 415

Tyr Tyr Cys Tyr Ala Gln Ser Thr Trp Tyr Pro Ser Trp Gly Gln
            420                 425                 430

Gly Thr Leu Val Thr Val Ser Ser
            435                 440

<210> SEQ ID NO 67
<211> LENGTH: 440
<212> TYPE: PRT
<213> ORGANISM: Homo sapiens

<400> SEQUENCE: 67

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
            115                 120                 125

Lys Ala Ile Gly Glu Leu Asp Leu Leu Phe Met Ser Leu Arg Asn Ala
        130                 135                 140

Cys Ile Ser Gly Gly Gly Ser Gly Gly Gly Ser Gly Gly Gly
145                 150                 155                 160

```
Gly Ser Ala Pro Ile Ser Ser His Cys Arg Leu Asp Lys Ser Asn Phe
                165                 170                 175

Gln Gln Pro Tyr Ile Thr Asn Arg Thr Phe Met Leu Ala Lys Glu Ala
            180                 185                 190

Ser Leu Ala Asp Asn Asn Thr Asp Val Arg Leu Ile Gly Glu Lys Leu
        195                 200                 205

Phe His Gly Val Ser Met Ser Glu Arg Cys Tyr Leu Met Lys Gln Val
    210                 215                 220

Leu Asn Phe Thr Leu Glu Glu Val Leu Phe Pro Gln Ser Asp Arg Phe
225                 230                 235                 240

Gln Pro Tyr Met Gln Glu Val Val Pro Phe Leu Ala Arg Leu Ser Asn
                245                 250                 255

Arg Leu Ser Thr Cys His Ile Glu Gly Asp Asp Leu His Ile Gln Arg
            260                 265                 270

Asn Val Gln Lys Leu Lys Asp Thr Val Lys Lys Leu Gly Glu Ser Gly
        275                 280                 285

Glu Ile Lys Ala Ile Gly Glu Leu Asp Leu Leu Phe Met Ser Leu Arg
    290                 295                 300

Asn Ala Cys Ile Gly Gly Ser Gly Gly Ser Gly Gly Gly Ser
305                 310                 315                 320

Gly Gly Gly Ser Glu Val Gln Leu Val Glu Ser Gly Gly Leu Val
            325                 330                 335

Gln Pro Gly Gly Ser Leu Arg Leu Ser Cys Ala Ala Ser Gly Ser Thr
                340                 345                 350

Trp Ser Ile Asn Thr Leu Ala Trp Tyr Arg Gln Ala Pro Gly Lys Gln
            355                 360                 365

Arg Asp Leu Val Ala Arg Ile Ser Ser Gly Gly Ser Thr Tyr Tyr Ala
            370                 375                 380

Asp Ser Val Lys Gly Arg Phe Thr Ile Ser Arg Asp Asn Ser Lys Asn
385                 390                 395                 400

Thr Leu Tyr Leu Gln Met Asn Ser Leu Arg Ala Glu Asp Thr Ala Val
                405                 410                 415

Tyr Tyr Cys Tyr Ala Gln Ser Thr Trp Tyr Pro Pro Ser Trp Gly Gln
            420                 425                 430

Gly Thr Leu Val Thr Val Ser Ser
            435                 440

<210> SEQ ID NO 68
<211> LENGTH: 440
<212> TYPE: PRT
<213> ORGANISM: Homo sapiens

<400> SEQUENCE: 68

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
                20                  25                  30

Ala Asp Asn Asn Thr Asp Val Arg Leu Ile Gly Glu Lys Leu Phe His
            35                  40                  45

Gly Val Ser Met Ser Glu Arg Cys Tyr Leu Met Lys Gln Val Leu Asn
        50                  55                  60

Phe Thr Leu Glu Glu Val Leu Phe Pro Gln Ser Asp Arg Phe Gln Pro
65                  70                  75                  80
```

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
            115                 120                 125

Lys Ala Ile Gly Glu Leu Asp Leu Leu Phe Met Ser Leu Arg Asn Ala
        130                 135                 140

Cys Ile Ser Gly Gly Gly Ser Gly Gly Gly Ser Gly Gly Gly
145                 150                 155                 160

Gly Ser Glu Val Gln Leu Val Glu Ser Gly Gly Leu Val Gln Pro
                165                 170                 175

Gly Gly Ser Leu Arg Leu Ser Cys Ala Ala Ser Gly Ser Thr Trp Ser
            180                 185                 190

Ile Asn Thr Leu Ala Trp Tyr Arg Gln Ala Pro Gly Lys Gln Arg Asp
            195                 200                 205

Leu Val Ala Arg Ile Ser Ser Gly Gly Ser Thr Tyr Tyr Ala Asp Ser
        210                 215                 220

Val Lys Gly Arg Phe Thr Ile Ser Arg Asp Asn Ser Lys Asn Thr Leu
225                 230                 235                 240

Tyr Leu Gln Met Asn Ser Leu Arg Ala Glu Asp Thr Ala Val Tyr Tyr
                245                 250                 255

Cys Tyr Ala Gln Ser Thr Trp Tyr Pro Pro Ser Trp Gly Gln Gly Thr
            260                 265                 270

Leu Val Thr Val Ser Ser Gly Gly Gly Ser Gly Gly Gly Ser Gly Gly
            275                 280                 285

Gly Ser Gly Gly Gly Ser Ala Pro Ile Ser Ser His Cys Arg Leu Asp
        290                 295                 300

Lys Ser Asn Phe Gln Gln Pro Tyr Ile Thr Asn Arg Thr Phe Met Leu
305                 310                 315                 320

Ala Lys Glu Ala Ser Leu Ala Asp Asn Asn Thr Asp Val Arg Leu Ile
                325                 330                 335

Gly Glu Lys Leu Phe His Gly Val Ser Met Ser Glu Arg Cys Tyr Leu
            340                 345                 350

Met Lys Gln Val Leu Asn Phe Thr Leu Glu Glu Val Leu Phe Pro Gln
            355                 360                 365

Ser Asp Arg Phe Gln Pro Tyr Met Gln Glu Val Val Pro Phe Leu Ala
        370                 375                 380

Arg Leu Ser Asn Arg Leu Ser Thr Cys His Ile Glu Gly Asp Asp Leu
385                 390                 395                 400

His Ile Gln Arg Asn Val Gln Lys Leu Lys Asp Thr Val Lys Lys Leu
                405                 410                 415

Gly Glu Ser Gly Glu Ile Lys Ala Ile Gly Glu Leu Asp Leu Leu Phe
            420                 425                 430

Met Ser Leu Arg Asn Ala Cys Ile
            435                 440

<210> SEQ ID NO 69
<211> LENGTH: 440
<212> TYPE: PRT
<213> ORGANISM: Homo sapiens

<400> SEQUENCE: 69

```
Gln Val Gln Leu Val Glu Ser Gly Gly Val Val Gln Pro Gly Gly
  1               5                  10                  15

Ser Leu Arg Leu Ser Cys Ala Ala Ser Gly Phe Ala Phe Arg Gly Phe
             20                  25                  30

Gly Met Ser Trp Val Arg Gln Ala Pro Gly Lys Gly Leu Glu Trp Val
             35                  40                  45

Ser Ser Ile Asn Asn Gly Gly Ser Asp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Gly Gly Pro Gly Ala Ser Pro Ser Gly Gln Gly Thr Gln Val
            100                 105                 110

Thr Val Ser Ser Gly Gly Gly Ser Gly Gly Gly Ser Gly Gly Gly Ser
            115                 120                 125

Gly Gly Gly Ser Ala Pro Ile Ser Ser His Cys Arg Leu Asp Lys Ser
130                 135                 140

Asn Phe Gln Gln Pro Tyr Ile Thr Asn Arg Thr Phe Met Leu Ala Lys
145                 150                 155                 160

Glu Ala Ser Leu Ala Asp Asn Asn Thr Asp Val Arg Leu Ile Gly Glu
                165                 170                 175

Lys Leu Phe His Gly Val Ser Met Ser Glu Arg Cys Tyr Leu Met Lys
            180                 185                 190

Gln Val Leu Asn Phe Thr Leu Glu Glu Val Leu Phe Pro Gln Ser Asp
            195                 200                 205

Arg Phe Gln Pro Tyr Met Gln Glu Val Val Pro Phe Leu Ala Arg Leu
210                 215                 220

Ser Asn Arg Leu Ser Thr Cys His Ile Glu Gly Asp Asp Leu His Ile
225                 230                 235                 240

Gln Arg Asn Val Gln Lys Leu Lys Asp Thr Val Lys Lys Leu Gly Glu
                245                 250                 255

Ser Gly Glu Ile Lys Ala Ile Gly Glu Leu Asp Leu Leu Phe Met Ser
            260                 265                 270

Leu Arg Asn Ala Cys Ile Ser Gly Gly Gly Ser Gly Gly Gly Gly
            275                 280                 285

Ser Gly Gly Gly Ser Ala Pro Ile Ser Ser His Cys Arg Leu Asp
290                 295                 300

Lys Ser Asn Phe Gln Gln Pro Tyr Ile Thr Asn Arg Thr Phe Met Leu
305                 310                 315                 320

Ala Lys Glu Ala Ser Leu Ala Asp Asn Asn Thr Asp Val Arg Leu Ile
                325                 330                 335

Gly Glu Lys Leu Phe His Gly Val Ser Met Ser Glu Arg Cys Tyr Leu
            340                 345                 350

Met Lys Gln Val Leu Asn Phe Thr Leu Glu Glu Val Leu Phe Pro Gln
            355                 360                 365

Ser Asp Arg Phe Gln Pro Tyr Met Gln Glu Val Val Pro Phe Leu Ala
370                 375                 380

Arg Leu Ser Asn Arg Leu Ser Thr Cys His Ile Glu Gly Asp Asp Leu
385                 390                 395                 400
```

His Ile Gln Arg Asn Val Gln Lys Leu Lys Asp Thr Val Lys Lys Leu
            405                 410                 415

Gly Glu Ser Gly Glu Ile Lys Ala Ile Gly Glu Leu Asp Leu Leu Phe
            420                 425                 430

Met Ser Leu Arg Asn Ala Cys Ile
            435                 440

<210> SEQ ID NO 70
<211> LENGTH: 440
<212> TYPE: PRT
<213> ORGANISM: Homo sapiens

<400> SEQUENCE: 70

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
            35                  40                  45

Gly Val Ser Met Ser Glu Arg Cys Tyr Leu Met Lys Gln Val Leu Asn
50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
            85                  90                  95

Ser Thr Cys His Ile Glu Gly Asp Asp Leu His Ile Gln Arg Asn Val
            100                 105                 110

Gln Lys Leu Lys Asp Thr Val Lys Leu Gly Glu Ser Gly Glu Ile
            115                 120                 125

Lys Ala Ile Gly Glu Leu Asp Leu Leu Phe Met Ser Leu Arg Asn Ala
            130                 135                 140

Cys Ile Ser Gly Gly Gly Ser Gly Gly Gly Ser Gly Gly Gly
145                 150                 155                 160

Gly Ser Gln Val Gln Leu Val Glu Ser Gly Gly Val Val Gln Pro
            165                 170                 175

Gly Gly Ser Leu Arg Leu Ser Cys Ala Ala Ser Gly Phe Ala Phe Arg
            180                 185                 190

Gly Phe Gly Met Ser Trp Val Arg Gln Ala Pro Gly Lys Gly Leu Glu
            195                 200                 205

Trp Val Ser Ser Ile Asn Asn Gly Gly Ser Asp Thr Tyr Tyr Ala Asp
            210                 215                 220

Ser Val Lys Gly Arg Phe Thr Ile Ser Arg Asp Asn Ser Lys Asn Thr
225                 230                 235                 240

Leu Tyr Leu Gln Met Asn Ser Leu Arg Ala Glu Asp Thr Ala Val Tyr
            245                 250                 255

Tyr Cys Ala Ile Gly Gly Pro Gly Ala Ser Pro Ser Gly Gln Gly Thr
            260                 265                 270

Gln Val Thr Val Ser Ser Gly Gly Gly Ser Gly Gly
            275                 280                 285

Gly Ser Gly Gly Gly Ser Ala Pro Ile Ser Ser His Cys Arg Leu Asp
            290                 295                 300

Lys Ser Asn Phe Gln Gln Pro Tyr Ile Thr Asn Arg Thr Phe Met Leu
305                 310                 315                 320

```
Ala Lys Glu Ala Ser Leu Ala Asp Asn Asn Thr Asp Val Arg Leu Ile
            325                 330                 335

Gly Glu Lys Leu Phe His Gly Val Ser Met Ser Glu Arg Cys Tyr Leu
            340                 345                 350

Met Lys Gln Val Leu Asn Phe Thr Leu Glu Glu Val Leu Phe Pro Gln
            355                 360                 365

Ser Asp Arg Phe Gln Pro Tyr Met Gln Glu Val Val Pro Phe Leu Ala
            370                 375                 380

Arg Leu Ser Asn Arg Leu Ser Thr Cys His Ile Glu Gly Asp Asp Leu
385                 390                 395                 400

His Ile Gln Arg Asn Val Gln Lys Leu Lys Asp Thr Val Lys Lys Leu
            405                 410                 415

Gly Glu Ser Gly Glu Ile Lys Ala Ile Gly Glu Leu Asp Leu Leu Phe
            420                 425                 430

Met Ser Leu Arg Asn Ala Cys Ile
            435                 440

<210> SEQ ID NO 71
<211> LENGTH: 323
<212> TYPE: PRT
<213> ORGANISM: Mus musculus

<400> SEQUENCE: 71

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Ser Gly Gly Ser Gly Gly Ser Gly Gly Ser Gly Leu Pro Val
            35                  40                  45

Asn Thr Arg Cys Lys Leu Glu Val Ser Asn Phe Gln Gln Pro Tyr Ile
50                  55                  60

Val Asn Arg Thr Phe Met Leu Ala Lys Glu Ala Ser Leu Ala Asp Asn
65                  70                  75                  80

Asn Thr Asp Val Arg Leu Ile Gly Glu Lys Leu Phe Arg Gly Val Ser
            85                  90                  95

Ala Lys Asp Gln Cys Tyr Leu Met Lys Gln Val Leu Asn Phe Thr Leu
            100                 105                 110

Glu Asp Val Leu Leu Pro Gln Ser Asp Arg Phe Gln Pro Tyr Met Gln
            115                 120                 125

Glu Val Val Pro Phe Leu Thr Lys Leu Ser Asn Gln Leu Ser Ser Cys
            130                 135                 140

His Ile Ser Gly Asp Asp Gln Asn Ile Gln Lys Asn Val Arg Arg Leu
145                 150                 155                 160

Lys Glu Thr Val Lys Lys Leu Gly Glu Ser Gly Glu Ile Lys Ala Ile
            165                 170                 175

Gly Glu Leu Asp Leu Leu Phe Met Ser Leu Arg Asn Ala Cys Val Ser
            180                 185                 190

Gly Gly Gly Gly Ser Gly Gly Gly Ser Gly Gly Gly Ser Glu
            195                 200                 205

Val Gln Leu Val Glu Ser Gly Gly Leu Val Gln Pro Gly Gly Ser
            210                 215                 220

Leu Arg Leu Ser Cys Ala Ala Ser Gly Ser Thr Trp Ser Ile Asn Thr
225                 230                 235                 240
```

```
Leu Ala Trp Tyr Arg Gln Ala Pro Gly Lys Gln Arg Asp Leu Val Ala
                245                 250                 255

Arg Ile Ser Ser Gly Gly Ser Thr Tyr Tyr Ala Asp Ser Val Lys Gly
            260                 265                 270

Arg Phe Thr Ile Ser Arg Asp Asn Ser Lys Asn Thr Leu Tyr Leu Gln
        275                 280                 285

Met Asn Ser Leu Arg Ala Glu Asp Thr Ala Val Tyr Tyr Cys Tyr Ala
    290                 295                 300

Gln Ser Thr Trp Tyr Pro Pro Ser Trp Gly Gln Gly Thr Leu Val Thr
305                 310                 315                 320

Val Ser Ser
```

<210> SEQ ID NO 72
<211> LENGTH: 323
<212> TYPE: PRT
<213> ORGANISM: Homo sapiens

<400> SEQUENCE: 72

```
His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Ser Gly Gly Ser Gly Gly Ser Gly Gly Ser Gly Glu Val Gln
        35                  40                  45

Leu Val Glu Ser Gly Gly Gly Leu Val Gln Pro Gly Gly Ser Leu Arg
    50                  55                  60

Leu Ser Cys Ala Ala Ser Gly Ser Thr Trp Ser Ile Asn Thr Leu Ala
65                  70                  75                  80

Trp Tyr Arg Gln Ala Pro Gly Lys Gln Arg Asp Leu Val Ala Arg Ile
                85                  90                  95

Ser Ser Gly Gly Ser Thr Tyr Tyr Ala Asp Ser Val Lys Gly Arg Phe
            100                 105                 110

Thr Ile Ser Arg Asp Asn Ser Lys Asn Thr Leu Tyr Leu Gln Met Asn
        115                 120                 125

Ser Leu Arg Ala Glu Asp Thr Ala Val Tyr Tyr Cys Tyr Ala Gln Ser
    130                 135                 140

Thr Trp Tyr Pro Pro Ser Trp Gly Gln Gly Thr Leu Val Thr Val Ser
145                 150                 155                 160

Ser Gly Gly Gly Ser Gly Gly Ser Gly Gly Ser Gly Gly
                165                 170                 175

Ser Ala Pro Ile Ser Ser His Cys Arg Leu Asp Lys Ser Asn Phe Gln
            180                 185                 190

Gln Pro Tyr Ile Thr Asn Arg Thr Phe Met Leu Ala Lys Glu Ala Ser
        195                 200                 205

Leu Ala Asp Asn Asn Thr Asp Val Arg Leu Ile Gly Glu Lys Leu Phe
    210                 215                 220

His Gly Val Ser Met Ser Glu Arg Cys Tyr Leu Met Lys Gln Val Leu
225                 230                 235                 240

Asn Phe Thr Leu Glu Glu Val Leu Phe Pro Gln Ser Asp Arg Phe Gln
                245                 250                 255

Pro Tyr Met Gln Glu Val Val Pro Phe Leu Ala Arg Leu Ser Asn Arg
            260                 265                 270

Leu Ser Thr Cys His Ile Glu Gly Asp Asp Leu His Ile Gln Arg Asn
        275                 280                 285
```

```
Val Gln Lys Leu Lys Asp Thr Val Lys Lys Leu Gly Glu Ser Gly Glu
290                 295                 300

Ile Lys Ala Ile Gly Glu Leu Asp Leu Leu Phe Met Ser Leu Arg Asn
305                 310                 315                 320

Ala Cys Ile

<210> SEQ ID NO 73
<211> LENGTH: 323
<212> TYPE: PRT
<213> ORGANISM: Homo sapiens

<400> SEQUENCE: 73

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Ile Gly Ser Gly Gly Ser Gly Gly Ser Gly Ser Gly Glu Val
145                 150                 155                 160

Gln Leu Val Glu Ser Gly Gly Leu Val Gln Pro Gly Gly Ser Leu
                165                 170                 175

Arg Leu Ser Cys Ala Ala Ser Gly Ser Thr Trp Ser Ile Asn Thr Leu
            180                 185                 190

Ala Trp Tyr Arg Gln Ala Pro Gly Lys Gln Arg Asp Leu Val Ala Arg
        195                 200                 205

Ile Ser Ser Gly Gly Ser Thr Tyr Tyr Ala Asp Ser Val Lys Gly Arg
210                 215                 220

Phe Thr Ile Ser Arg Asp Asn Ser Lys Asn Thr Leu Tyr Leu Gln Met
225                 230                 235                 240

Asn Ser Leu Arg Ala Glu Asp Thr Ala Val Tyr Tyr Cys Tyr Ala Gln
                245                 250                 255

Ser Thr Trp Tyr Pro Pro Ser Trp Gly Gln Gly Thr Leu Val Thr Val
            260                 265                 270

Ser Ser Gly Gly Gly Ser Gly Gly Ser Gly Gly Ser Gly Gly
        275                 280                 285

Gly Ser His Gly Asp Gly Ser Phe Ser Asp Glu Met Asn Thr Ile Leu
290                 295                 300

Asp Asn Leu Ala Ala Arg Asp Phe Ile Asn Trp Leu Ile Gln Thr Lys
305                 310                 315                 320

Ile Thr Asp
```

-continued

```
<210> SEQ ID NO 74
<211> LENGTH: 323
<212> TYPE: PRT
<213> ORGANISM: Homo sapiens

<400> SEQUENCE: 74

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
                20                  25                  30

Asp Gly Ser Gly Gly Ser Gly Gly Ser Gly Gly Ser Gly Ala Pro Ile
            35                  40                  45

Ser Ser His Cys Arg Leu Asp Lys Ser Asn Phe Gln Gln Pro Tyr Ile
50                  55                  60

Thr Asn Arg Thr Phe Met Leu Ala Lys Glu Ala Ser Leu Ala Asp Asn
65                  70                  75                  80

Asn Thr Asp Val Arg Leu Ile Gly Glu Lys Leu Phe His Gly Val Ser
                85                  90                  95

Met Ser Glu Arg Cys Tyr Leu Met Lys Gln Val Leu Asn Phe Thr Leu
            100                 105                 110

Glu Glu Val Leu Phe Pro Gln Ser Asp Arg Phe Gln Pro Tyr Met Gln
        115                 120                 125

Glu Val Val Pro Phe Leu Ala Arg Leu Ser Asn Arg Leu Ser Thr Cys
130                 135                 140

His Ile Glu Gly Asp Asp Leu His Ile Gln Arg Asn Val Gln Lys Leu
145                 150                 155                 160

Lys Asp Thr Val Lys Lys Leu Gly Glu Ser Gly Glu Ile Lys Ala Ile
                165                 170                 175

Gly Glu Leu Asp Leu Leu Phe Met Ser Leu Arg Asn Ala Cys Ile Ser
            180                 185                 190

Gly Gly Gly Gly Ser Gly Gly Gly Ser Gly Gly Gly Gly Ser Glu
        195                 200                 205

Val Gln Leu Val Glu Ser Gly Gly Leu Val Gln Pro Gly Gly Ser
210                 215                 220

Leu Arg Leu Ser Cys Ala Ala Ser Gly Ser Thr Trp Ser Ile Asn Thr
225                 230                 235                 240

Leu Ala Trp Tyr Arg Gln Ala Pro Gly Lys Gln Arg Asp Leu Val Ala
                245                 250                 255

Arg Ile Ser Ser Gly Gly Ser Thr Tyr Tyr Ala Asp Ser Val Lys Gly
            260                 265                 270

Arg Phe Thr Ile Ser Arg Asp Asn Ser Lys Asn Thr Leu Tyr Leu Gln
        275                 280                 285

Met Asn Ser Leu Arg Ala Glu Asp Thr Ala Val Tyr Tyr Cys Tyr Ala
290                 295                 300

Gln Ser Thr Trp Tyr Pro Pro Ser Trp Gly Gln Gly Thr Leu Val Thr
305                 310                 315                 320

Val Ser Ser

<210> SEQ ID NO 75
<211> LENGTH: 323
<212> TYPE: PRT
<213> ORGANISM: Mus musculus

<400> SEQUENCE: 75

Gln Val Gln Leu Val Glu Ser Gly Gly Gly Val Val Gln Pro Gly Gly
1               5                   10                  15
```

-continued

```
Ser Leu Arg Leu Ser Cys Ala Ala Ser Gly Phe Ala Phe Arg Gly Phe
         20                  25                  30
Gly Met Ser Trp Val Arg Gln Ala Pro Gly Lys Gly Leu Glu Trp Val
         35                  40                  45
Ser Ser Ile Asn Asn Gly Gly Ser Asp Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Ile Gly Gly Pro Gly Ala Ser Pro Ser Gly Gln Gly Thr Gln Val
                100                 105                 110
Thr Val Ser Ser Gly Gly Gly Ser Gly Gly Ser Gly Gly Gly Ser
            115                 120                 125
Gly Gly Gly Ser Leu Pro Val Asn Thr Arg Cys Lys Leu Glu Val Ser
130                 135                 140
Asn Phe Gln Gln Pro Tyr Ile Val Asn Arg Thr Phe Met Leu Ala Lys
145                 150                 155                 160
Glu Ala Ser Leu Ala Asp Asn Asn Thr Asp Val Arg Leu Ile Gly Glu
                165                 170                 175
Lys Leu Phe Arg Gly Val Ser Ala Lys Asp Gln Cys Tyr Leu Met Lys
            180                 185                 190
Gln Val Leu Asn Phe Thr Leu Glu Asp Val Leu Leu Pro Gln Ser Asp
        195                 200                 205
Arg Phe Gln Pro Tyr Met Gln Glu Val Val Pro Phe Leu Thr Lys Leu
210                 215                 220
Ser Asn Gln Leu Ser Ser Cys His Ile Ser Gly Asp Asp Gln Asn Ile
225                 230                 235                 240
Gln Lys Asn Val Arg Arg Leu Lys Glu Thr Val Lys Lys Leu Gly Glu
                245                 250                 255
Ser Gly Glu Ile Lys Ala Ile Gly Glu Leu Asp Leu Leu Phe Met Ser
            260                 265                 270
Leu Arg Asn Ala Cys Val Gly Ser Gly Ser Gly Ser Gly Ser Gly Gly
        275                 280                 285
Ser Gly His Gly Asp Gly Ser Phe Ser Asp Glu Met Asn Thr Ile Leu
290                 295                 300
Asp Asn Leu Ala Ala Arg Asp Phe Ile Asn Trp Leu Ile Gln Thr Lys
305                 310                 315                 320
Ile Thr Asp
```

<210> SEQ ID NO 76
<211> LENGTH: 323
<212> TYPE: PRT
<213> ORGANISM: Homo sapiens

<400> SEQUENCE: 76

```
His Gly Asp Gly Ser Phe Ser Asp Glu Met Asn Thr Ile Leu Asp Asn
 1               5                  10                  15
Leu Ala Ala Arg Asp Phe Ile Asn Trp Leu Ile Gln Thr Lys Ile Thr
             20                  25                  30
Asp Gly Ser Gly Gly Ser Gly Gly Ser Gly Gln Val Gln
         35                  40                  45
Leu Val Glu Ser Gly Gly Val Val Gln Pro Gly Gly Ser Leu Arg
     50                  55                  60
```

```
Leu Ser Cys Ala Ala Ser Gly Phe Ala Phe Arg Gly Phe Gly Met Ser
 65                  70                  75                  80

Trp Val Arg Gln Ala Pro Gly Lys Gly Leu Glu Trp Val Ser Ser Ile
                 85                  90                  95

Asn Asn Gly Gly Ser Asp Thr Tyr Tyr Ala Asp Ser Val Lys Gly Arg
            100                 105                 110

Phe Thr Ile Ser Arg Asp Asn Ser Lys Asn Thr Leu Tyr Leu Gln Met
        115                 120                 125

Asn Ser Leu Arg Ala Glu Asp Thr Ala Val Tyr Tyr Cys Ala Ile Gly
130                 135                 140

Gly Pro Gly Ala Ser Pro Ser Gly Gln Gly Thr Gln Val Thr Val Ser
145                 150                 155                 160

Ser Gly Gly Gly Ser Gly Gly Gly Ser Gly Gly Ser Gly Gly Gly
                165                 170                 175

Ser Ala Pro Ile Ser Ser His Cys Arg Leu Asp Lys Ser Asn Phe Gln
            180                 185                 190

Gln Pro Tyr Ile Thr Asn Arg Thr Phe Met Leu Ala Lys Glu Ala Ser
        195                 200                 205

Leu Ala Asp Asn Asn Thr Asp Val Arg Leu Ile Gly Glu Lys Leu Phe
210                 215                 220

His Gly Val Ser Met Ser Glu Arg Cys Tyr Leu Met Lys Gln Val Leu
225                 230                 235                 240

Asn Phe Thr Leu Glu Glu Val Leu Phe Pro Gln Ser Asp Arg Phe Gln
            245                 250                 255

Pro Tyr Met Gln Glu Val Val Pro Phe Leu Ala Arg Leu Ser Asn Arg
        260                 265                 270

Leu Ser Thr Cys His Ile Glu Gly Asp Asp Leu His Ile Gln Arg Asn
275                 280                 285

Val Gln Lys Leu Lys Asp Thr Val Lys Lys Leu Gly Glu Ser Gly Glu
    290                 295                 300

Ile Lys Ala Ile Gly Glu Leu Asp Leu Leu Phe Met Ser Leu Arg Asn
305                 310                 315                 320

Ala Cys Ile

<210> SEQ ID NO 77
<211> LENGTH: 323
<212> TYPE: PRT
<213> ORGANISM: Homo sapiens

<400> SEQUENCE: 77

Ala Pro Ile Ser Ser His Cys Arg Leu Asp Lys Ser Asn Phe Gln Gln
1                5                  10                  15

Pro Tyr Ile Thr Asn Arg Thr Phe Met Leu Ala Lys Glu Ala Ser Leu
             20                  25                  30

Ala Asp Asn Asn Thr Asp Val Arg Leu Ile Gly Glu Lys Leu Phe His
         35                  40                  45

Gly Val Ser Met Ser Glu Arg Cys Tyr Leu Met Lys Gln Val Leu Asn
     50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                 85                  90                  95

Ser Thr Cys His Ile Glu Gly Asp Asp Leu His Ile Gln Arg Asn Val
            100                 105                 110
```

```
Gln Lys Leu Lys Asp Thr Val Lys Lys Leu Gly Glu Ser Gly Glu Ile
            115                 120                 125
Lys Ala Ile Gly Glu Leu Asp Leu Leu Phe Met Ser Leu Arg Asn Ala
130                 135                 140
Cys Ile Gly Ser Gly Ser Gly Ser Gly Ser Gly Gln Val
145                 150                 155                 160
Gln Leu Val Glu Ser Gly Gly Val Val Gln Pro Gly Gly Ser Leu
                165                 170                 175
Arg Leu Ser Cys Ala Ala Ser Gly Phe Ala Phe Arg Gly Phe Gly Met
                180                 185                 190
Ser Trp Val Arg Gln Ala Pro Gly Lys Gly Leu Glu Trp Val Ser Ser
                195                 200                 205
Ile Asn Asn Gly Gly Ser Asp Thr Tyr Tyr Ala Asp Ser Val Lys Gly
                210                 215                 220
Arg Phe Thr Ile Ser Arg Asp Asn Ser Lys Asn Thr Leu Tyr Leu Gln
225                 230                 235                 240
Met Asn Ser Leu Arg Ala Glu Asp Thr Ala Val Tyr Tyr Cys Ala Ile
                245                 250                 255
Gly Gly Pro Gly Ala Ser Pro Ser Gly Gln Gly Thr Gln Val Thr Val
                260                 265                 270
Ser Ser Gly Gly Gly Ser Gly Gly Ser Gly Gly Ser Gly Gly
                275                 280                 285
Gly Ser His Gly Asp Gly Ser Phe Ser Asp Glu Met Asn Thr Ile Leu
                290                 295                 300
Asp Asn Leu Ala Ala Arg Asp Phe Ile Asn Trp Leu Ile Gln Thr Lys
305                 310                 315                 320
Ile Thr Asp

<210> SEQ ID NO 78
<211> LENGTH: 323
<212> TYPE: PRT
<213> ORGANISM: Homo sapiens

<400> SEQUENCE: 78

Gln Val Gln Leu Val Glu Ser Gly Gly Gly Val Val Gln Pro Gly Gly
1               5                   10                  15
Ser Leu Arg Leu Ser Cys Ala Ala Ser Gly Phe Ala Phe Arg Gly Phe
                20                  25                  30
Gly Met Ser Trp Val Arg Gln Ala Pro Gly Lys Gly Leu Glu Trp Val
                35                  40                  45
Ser Ser Ile Asn Asn Gly Gly Ser Asp Thr Tyr Tyr Ala Asp Ser Val
            50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ile Gly Gly Pro Gly Ala Ser Pro Ser Gly Gln Gly Thr Gln Val
                100                 105                 110
Thr Val Ser Ser Gly Gly Gly Ser Gly Gly Gly Ser Gly Gly Gly Ser
            115                 120                 125
Gly Gly Gly Ser Ala Pro Ile Ser Ser His Cys Arg Leu Asp Lys Ser
            130                 135                 140
Asn Phe Gln Gln Pro Tyr Ile Thr Asn Arg Thr Phe Met Leu Ala Lys
145                 150                 155                 160
```

-continued

```
Glu Ala Ser Leu Ala Asp Asn Thr Asp Val Arg Leu Ile Gly Glu
                165                 170                 175

Lys Leu Phe His Gly Val Ser Met Ser Glu Arg Cys Tyr Leu Met Lys
            180                 185                 190

Gln Val Leu Asn Phe Thr Leu Glu Glu Val Leu Phe Pro Gln Ser Asp
        195                 200                 205

Arg Phe Gln Pro Tyr Met Gln Glu Val Val Pro Phe Leu Ala Arg Leu
    210                 215                 220

Ser Asn Arg Leu Ser Thr Cys His Ile Glu Gly Asp Leu His Ile
225                 230                 235                 240

Gln Arg Asn Val Gln Lys Leu Lys Asp Thr Val Lys Lys Leu Gly Glu
                245                 250                 255

Ser Gly Glu Ile Lys Ala Ile Gly Glu Leu Asp Leu Leu Phe Met Ser
            260                 265                 270

Leu Arg Asn Ala Cys Ile Gly Ser Gly Gly Ser Gly Gly Ser Gly Gly
        275                 280                 285

Ser Gly His Gly Asp Gly Ser Phe Ser Asp Glu Met Asn Thr Ile Leu
    290                 295                 300

Asp Asn Leu Ala Ala Arg Asp Phe Ile Asn Trp Leu Ile Gln Thr Lys
305                 310                 315                 320

Ile Thr Asp

<210> SEQ ID NO 79
<211> LENGTH: 360
<212> TYPE: PRT
<213> ORGANISM: Mus musculus

<400> SEQUENCE: 79

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala Gly Ser Gly Gly Ser Gly Gly Ser Gly Gly
65                  70                  75                  80

Ser Gly Leu Pro Val Asn Thr Arg Cys Lys Leu Glu Val Ser Asn Phe
                85                  90                  95

Gln Gln Pro Tyr Ile Val Asn Arg Thr Phe Met Leu Ala Lys Glu Ala
            100                 105                 110

Ser Leu Ala Asp Asn Asn Thr Asp Val Arg Leu Ile Gly Glu Lys Leu
        115                 120                 125

Phe Arg Gly Val Ser Ala Lys Asp Gln Cys Tyr Leu Met Lys Gln Val
    130                 135                 140

Leu Asn Phe Thr Leu Glu Asp Val Leu Leu Pro Gln Ser Asp Arg Phe
145                 150                 155                 160

Gln Pro Tyr Met Gln Glu Val Val Pro Phe Leu Thr Lys Leu Ser Asn
                165                 170                 175

Gln Leu Ser Ser Cys His Ile Ser Gly Asp Asp Gln Asn Ile Gln Lys
            180                 185                 190

Asn Val Arg Arg Leu Lys Glu Thr Val Lys Lys Leu Gly Glu Ser Gly
        195                 200                 205
```

```
Glu Ile Lys Ala Ile Gly Glu Leu Asp Leu Leu Phe Met Ser Leu Arg
    210                 215                 220

Asn Ala Cys Val Ser Gly Gly Gly Ser Gly Gly Gly Ser Gly
225                 230                 235                 240

Gly Gly Gly Ser Glu Val Gln Leu Val Glu Ser Gly Gly Leu Val
                245                 250                 255

Gln Pro Gly Gly Ser Leu Arg Leu Ser Cys Ala Ala Ser Gly Ser Thr
            260                 265                 270

Trp Ser Ile Asn Thr Leu Ala Trp Tyr Arg Gln Ala Pro Gly Lys Gln
        275                 280                 285

Arg Asp Leu Val Ala Arg Ile Ser Ser Gly Gly Ser Thr Tyr Tyr Ala
    290                 295                 300

Asp Ser Val Lys Gly Arg Phe Thr Ile Ser Arg Asp Asn Ser Lys Asn
305                 310                 315                 320

Thr Leu Tyr Leu Gln Met Asn Ser Leu Arg Ala Glu Asp Thr Ala Val
                325                 330                 335

Tyr Tyr Cys Tyr Ala Gln Ser Thr Trp Tyr Pro Pro Ser Trp Gly Gln
            340                 345                 350

Gly Thr Leu Val Thr Val Ser Ser
            355                 360

<210> SEQ ID NO 80
<211> LENGTH: 357
<212> TYPE: PRT
<213> ORGANISM: Homo sapiens

<400> SEQUENCE: 80

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala Gly Ser Gly Gly Ser Gly Gly Ser Gly Glu
65                  70                  75                  80

Val Gln Leu Val Glu Ser Gly Gly Gly Leu Val Gln Pro Gly Gly Ser
                85                  90                  95

Leu Arg Leu Ser Cys Ala Ala Ser Gly Ser Thr Trp Ser Ile Asn Thr
            100                 105                 110

Leu Ala Trp Tyr Arg Gln Ala Pro Gly Lys Gln Arg Asp Leu Val Ala
        115                 120                 125

Arg Ile Ser Ser Gly Gly Ser Thr Tyr Tyr Ala Asp Ser Val Lys Gly
    130                 135                 140

Arg Phe Thr Ile Ser Arg Asp Asn Ser Lys Asn Thr Leu Tyr Leu Gln
145                 150                 155                 160

Met Asn Ser Leu Arg Ala Glu Asp Thr Ala Val Tyr Tyr Cys Tyr Ala
                165                 170                 175

Gln Ser Thr Trp Tyr Pro Pro Ser Trp Gly Gln Gly Thr Leu Val Thr
            180                 185                 190

Val Ser Ser Gly Gly Gly Gly Ser Gly Gly Gly Gly Ser Gly
        195                 200                 205
```

-continued

Gly Gly Ser Ala Pro Ile Ser Ser His Cys Arg Leu Asp Lys Ser Asn
210                 215                 220

Phe Gln Gln Pro Tyr Ile Thr Asn Arg Thr Phe Met Leu Ala Lys Glu
225                 230                 235                 240

Ala Ser Leu Ala Asp Asn Asn Thr Asp Val Arg Leu Ile Gly Glu Lys
                245                 250                 255

Leu Phe His Gly Val Ser Met Ser Glu Arg Cys Tyr Leu Met Lys Gln
                260                 265                 270

Val Leu Asn Phe Thr Leu Glu Glu Val Leu Phe Pro Gln Ser Asp Arg
                275                 280                 285

Phe Gln Pro Tyr Met Gln Glu Val Val Pro Phe Leu Ala Arg Leu Ser
290                 295                 300

Asn Arg Leu Ser Thr Cys His Ile Glu Gly Asp Asp Leu His Ile Gln
305                 310                 315                 320

Arg Asn Val Gln Lys Leu Lys Asp Thr Val Lys Lys Leu Gly Glu Ser
                325                 330                 335

Gly Glu Ile Lys Ala Ile Gly Glu Leu Asp Leu Leu Phe Met Ser Leu
                340                 345                 350

Arg Asn Ala Cys Ile
                355

<210> SEQ ID NO 81
<211> LENGTH: 357
<212> TYPE: PRT
<213> ORGANISM: Homo sapiens

<400> SEQUENCE: 81

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
                20                  25                  30

Ala Asp Asn Asn Thr Asp Val Arg Leu Ile Gly Glu Lys Leu Phe His
            35                  40                  45

Gly Val Ser Met Ser Glu Arg Cys Tyr Leu Met Lys Gln Val Leu Asn
50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Gly Ser Gly Gly Ser Gly Ser Gly Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Ser Thr Trp Ser Ile Asn Thr Leu Ala Trp Tyr
            180                 185                 190

Arg Gln Ala Pro Gly Lys Gln Arg Asp Leu Val Ala Arg Ile Ser Ser
        195                 200                 205

Gly Gly Ser Thr Tyr Tyr Ala Asp Ser Val Lys Gly Arg Phe Thr Ile
    210                 215                 220

-continued

Ser Arg Asp Asn Ser Lys Asn Thr Leu Tyr Leu Gln Met Asn Ser Leu
225                 230                 235                 240

Arg Ala Glu Asp Thr Ala Val Tyr Tyr Cys Tyr Ala Gln Ser Thr Trp
            245                 250                 255

Tyr Pro Pro Ser Trp Gly Gln Gly Thr Leu Val Thr Val Ser Ser Gly
        260                 265                 270

Gly Gly Ser Gly Gly Gly Ser Gly Gly Gly Ser Gly Gly Gly Ser Gly
        275                 280                 285

Pro Glu Thr Leu Cys Gly Ala Glu Leu Val Asp Ala Leu Gln Phe Val
        290                 295                 300

Cys Gly Asp Arg Gly Phe Tyr Phe Asn Lys Pro Thr Gly Tyr Gly Ser
305                 310                 315                 320

Ser Ser Arg Arg Ala Pro Gln Thr Gly Ile Val Asp Glu Cys Cys Phe
            325                 330                 335

Arg Ser Cys Asp Leu Arg Arg Leu Glu Met Tyr Cys Ala Pro Leu Lys
            340                 345                 350

Pro Ala Lys Ser Ala
        355

<210> SEQ ID NO 82
<211> LENGTH: 360
<212> TYPE: PRT
<213> ORGANISM: Homo sapiens

<400> SEQUENCE: 82

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
50                  55                  60

Lys Pro Ala Lys Ser Ala Gly Ser Gly Gly Ser Gly Gly Ser Gly Gly
65                  70                  75                  80

Ser Gly Ala Pro Ile Ser Ser His Cys Arg Leu Asp Lys Ser Asn Phe
                85                  90                  95

Gln Gln Pro Tyr Ile Thr Asn Arg Thr Phe Met Leu Ala Lys Glu Ala
            100                 105                 110

Ser Leu Ala Asp Asn Asn Thr Asp Val Arg Leu Ile Gly Glu Lys Leu
        115                 120                 125

Phe His Gly Val Ser Met Ser Glu Arg Cys Tyr Leu Met Lys Gln Val
130                 135                 140

Leu Asn Phe Thr Leu Glu Glu Val Leu Phe Pro Gln Ser Asp Arg Phe
145                 150                 155                 160

Gln Pro Tyr Met Gln Glu Val Val Pro Phe Leu Ala Arg Leu Ser Asn
            165                 170                 175

Arg Leu Ser Thr Cys His Ile Glu Gly Asp Asp Leu His Ile Gln Arg
        180                 185                 190

Asn Val Gln Lys Leu Lys Asp Thr Val Lys Lys Leu Gly Glu Ser Gly
        195                 200                 205

Glu Ile Lys Ala Ile Gly Glu Leu Asp Leu Leu Phe Met Ser Leu Arg
210                 215                 220

```
Asn Ala Cys Ile Ser Gly Gly Gly Ser Gly Gly Gly Ser Gly
225                 230                 235                 240

Gly Gly Gly Ser Glu Val Gln Leu Val Glu Ser Gly Gly Leu Val
            245                 250                 255

Gln Pro Gly Gly Ser Leu Arg Leu Ser Cys Ala Ala Ser Gly Ser Thr
        260                 265                 270

Trp Ser Ile Asn Thr Leu Ala Trp Tyr Arg Gln Ala Pro Gly Lys Gln
    275                 280                 285

Arg Asp Leu Val Ala Arg Ile Ser Ser Gly Gly Ser Thr Tyr Tyr Ala
290                 295                 300

Asp Ser Val Lys Gly Arg Phe Thr Ile Ser Arg Asp Asn Ser Lys Asn
305                 310                 315                 320

Thr Leu Tyr Leu Gln Met Asn Ser Leu Arg Ala Glu Asp Thr Ala Val
                325                 330                 335

Tyr Tyr Cys Tyr Ala Gln Ser Thr Trp Tyr Pro Pro Ser Trp Gly Gln
            340                 345                 350

Gly Thr Leu Val Thr Val Ser Ser
            355                 360

<210> SEQ ID NO 83
<211> LENGTH: 360
<212> TYPE: PRT
<213> ORGANISM: Mus musculus

<400> SEQUENCE: 83

Gln Val Gln Leu Val Glu Ser Gly Gly Val Val Gln Pro Gly Gly
1               5                   10                  15

Ser Leu Arg Leu Ser Cys Ala Ala Ser Gly Phe Ala Phe Arg Gly Phe
            20                  25                  30

Gly Met Ser Trp Val Arg Gln Ala Pro Gly Lys Gly Leu Glu Trp Val
        35                  40                  45

Ser Ser Ile Asn Asn Gly Gly Ser Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gly Gly Pro Gly Ala Ser Pro Ser Gly Gln Gly Thr Gln Val
            100                 105                 110

Thr Val Ser Ser Gly Gly Gly Ser Gly Gly Gly Ser Gly Gly Gly Ser
        115                 120                 125

Gly Gly Gly Ser Leu Pro Val Asn Thr Arg Cys Lys Leu Glu Val Ser
    130                 135                 140

Asn Phe Gln Gln Pro Tyr Ile Val Asn Arg Thr Phe Met Leu Ala Lys
145                 150                 155                 160

Glu Ala Ser Leu Ala Asp Asn Asn Thr Asp Val Arg Leu Ile Gly Glu
                165                 170                 175

Lys Leu Phe Arg Gly Val Ser Ala Lys Asp Gln Cys Tyr Leu Met Lys
            180                 185                 190

Gln Val Leu Asn Phe Thr Leu Glu Asp Val Leu Leu Pro Gln Ser Asp
        195                 200                 205

Arg Phe Gln Pro Tyr Met Gln Glu Val Val Pro Phe Leu Thr Lys Leu
    210                 215                 220

Ser Asn Gln Leu Ser Ser Cys His Ile Ser Gly Asp Asp Gln Asn Ile
225                 230                 235                 240
```

Gln Lys Asn Val Arg Arg Leu Lys Glu Thr Val Lys Leu Gly Glu
            245                 250                 255

Ser Gly Glu Ile Lys Ala Ile Gly Glu Leu Asp Leu Leu Phe Met Ser
            260                 265                 270

Leu Arg Asn Ala Cys Val Gly Ser Gly Ser Gly Gly Ser Gly Gly
            275                 280                 285

Ser Gly Gly Pro Glu Thr Leu Cys Gly Ala Glu Leu Val Asp Ala Leu
        290                 295                 300

Gln Phe Val Cys Gly Asp Arg Gly Phe Tyr Phe Asn Lys Pro Thr Gly
305                 310                 315                 320

Tyr Gly Ser Ser Ser Arg Arg Ala Pro Gln Thr Gly Ile Val Asp Glu
                325                 330                 335

Cys Cys Phe Arg Ser Cys Asp Leu Arg Arg Leu Glu Met Tyr Cys Ala
                340                 345                 350

Pro Leu Lys Pro Ala Lys Ser Ala
            355                 360

<210> SEQ ID NO 84
<211> LENGTH: 357
<212> TYPE: PRT
<213> ORGANISM: Homo sapiens

<400> SEQUENCE: 84

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
50                  55                  60

Lys Pro Ala Lys Ser Ala Gly Ser Gly Gly Ser Gly Gly Ser Gly Gln
65                  70                  75                  80

Val Gln Leu Val Glu Ser Gly Gly Val Val Gln Pro Gly Gly Ser
                85                  90                  95

Leu Arg Leu Ser Cys Ala Ala Ser Gly Phe Ala Phe Arg Gly Phe Gly
            100                 105                 110

Met Ser Trp Val Arg Gln Ala Pro Gly Lys Gly Leu Glu Trp Val Ser
            115                 120                 125

Ser Ile Asn Asn Gly Gly Ser Asp Thr Tyr Tyr Ala Asp Ser Val Lys
        130                 135                 140

Gly Arg Phe Thr Ile Ser Arg Asp Asn Ser Lys Asn Thr Leu Tyr Leu
145                 150                 155                 160

Gln Met Asn Ser Leu Arg Ala Glu Asp Thr Ala Val Tyr Tyr Cys Ala
                165                 170                 175

Ile Gly Gly Pro Gly Ala Ser Pro Gly Gln Gly Thr Gln Val Thr
            180                 185                 190

Val Ser Ser Gly Gly Gly Ser Gly Gly Ser Gly Gly Ser Gly
            195                 200                 205

Gly Gly Ser Ala Pro Ile Ser Ser His Cys Arg Leu Asp Lys Ser Asn
        210                 215                 220

Phe Gln Gln Pro Tyr Ile Thr Asn Arg Thr Phe Met Leu Ala Lys Glu
225                 230                 235                 240

```
Ala Ser Leu Ala Asp Asn Asn Thr Asp Val Arg Leu Ile Gly Glu Lys
            245                 250                 255

Leu Phe His Gly Val Ser Met Ser Glu Arg Cys Tyr Leu Met Lys Gln
        260                 265                 270

Val Leu Asn Phe Thr Leu Glu Glu Val Leu Phe Pro Gln Ser Asp Arg
        275                 280                 285

Phe Gln Pro Tyr Met Gln Glu Val Val Pro Phe Leu Ala Arg Leu Ser
    290                 295                 300

Asn Arg Leu Ser Thr Cys His Ile Glu Gly Asp Asp Leu His Ile Gln
305                 310                 315                 320

Arg Asn Val Gln Lys Leu Lys Asp Thr Val Lys Lys Leu Gly Glu Ser
                325                 330                 335

Gly Glu Ile Lys Ala Ile Gly Glu Leu Asp Leu Leu Phe Met Ser Leu
            340                 345                 350

Arg Asn Ala Cys Ile
            355

<210> SEQ ID NO 85
<211> LENGTH: 357
<212> TYPE: PRT
<213> ORGANISM: Homo sapiens

<400> SEQUENCE: 85

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Gly Ser Gly Gly Ser Gly Gly Ser Gln Val Gln Leu Val
145                 150                 155                 160

Glu Ser Gly Gly Gly Val Val Gln Pro Gly Ser Leu Arg Leu Ser
                165                 170                 175

Cys Ala Ala Ser Gly Phe Ala Phe Arg Gly Phe Gly Met Ser Trp Val
            180                 185                 190

Arg Gln Ala Pro Gly Lys Gly Leu Glu Trp Val Ser Ser Ile Asn Asn
        195                 200                 205

Gly Gly Ser Asp Thr Tyr Tyr Ala Asp Ser Val Lys Gly Arg Phe Thr
    210                 215                 220

Ile Ser Arg Asp Asn Ser Lys Asn Thr Leu Tyr Leu Gln Met Asn Ser
225                 230                 235                 240

Leu Arg Ala Glu Asp Thr Ala Val Tyr Tyr Cys Ala Ile Gly Gly Pro
                245                 250                 255
```

```
Gly Ala Ser Pro Ser Gly Gln Gly Thr Gln Val Ser Ser Gly
            260                 265                 270

Gly Gly Ser Gly Gly Ser Gly Gly Ser Gly Gly Ser Gly
        275                 280                 285

Pro Glu Thr Leu Cys Gly Ala Glu Leu Val Asp Ala Leu Gln Phe Val
290                 295                 300

Cys Gly Asp Arg Gly Phe Tyr Phe Asn Lys Pro Thr Gly Tyr Gly Ser
305                 310                 315                 320

Ser Ser Arg Arg Ala Pro Gln Thr Gly Ile Val Asp Glu Cys Cys Phe
                325                 330                 335

Arg Ser Cys Asp Leu Arg Arg Leu Glu Met Tyr Cys Ala Pro Leu Lys
                340                 345                 350

Pro Ala Lys Ser Ala
            355

<210> SEQ ID NO 86
<211> LENGTH: 360
<212> TYPE: PRT
<213> ORGANISM: Homo sapiens

<400> SEQUENCE: 86

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ala Phe Arg Gly Phe
            20                  25                  30

Gly Met Ser Trp Val Arg Gln Ala Pro Gly Lys Gly Leu Glu Trp Val
        35                  40                  45

Ser Ser Ile Asn Asn Gly Gly Ser Asp Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gly Gly Pro Gly Ala Ser Pro Ser Gly Gln Gly Thr Gln Val
            100                 105                 110

Thr Val Ser Ser Gly Gly Gly Ser Gly Gly Gly Ser Gly Gly Gly Ser
        115                 120                 125

Gly Gly Gly Ser Ala Pro Ile Ser Ser His Cys Arg Leu Asp Lys Ser
130                 135                 140

Asn Phe Gln Gln Pro Tyr Ile Thr Asn Arg Thr Phe Met Leu Ala Lys
145                 150                 155                 160

Glu Ala Ser Leu Ala Asp Asn Asn Thr Asp Val Arg Leu Ile Gly Glu
                165                 170                 175

Lys Leu Phe His Gly Val Ser Met Ser Glu Arg Cys Tyr Leu Met Lys
            180                 185                 190

Gln Val Leu Asn Phe Thr Leu Glu Glu Val Leu Phe Pro Gln Ser Asp
        195                 200                 205

Arg Phe Gln Pro Tyr Met Gln Glu Val Val Pro Phe Leu Ala Arg Leu
210                 215                 220

Ser Asn Arg Leu Ser Thr Cys His Ile Glu Gly Asp Asp Leu His Ile
225                 230                 235                 240

Gln Arg Asn Val Gln Lys Leu Lys Asp Thr Val Lys Lys Leu Gly Glu
                245                 250                 255
```

```
Ser Gly Glu Ile Lys Ala Ile Gly Glu Leu Asp Leu Phe Met Ser
            260                 265                 270

Leu Arg Asn Ala Cys Ile Gly Ser Gly Gly Ser Gly Ser Gly Gly
        275                 280                 285

Ser Gly Gly Pro Glu Thr Leu Cys Gly Ala Glu Leu Val Asp Ala Leu
        290                 295                 300

Gln Phe Val Cys Gly Asp Arg Gly Phe Tyr Phe Asn Lys Pro Thr Gly
305                 310                 315                 320

Tyr Gly Ser Ser Arg Arg Ala Pro Gln Thr Gly Ile Val Asp Glu
                325                 330                 335

Cys Cys Phe Arg Ser Cys Asp Leu Arg Arg Leu Glu Met Tyr Cys Ala
                340                 345                 350

Pro Leu Lys Pro Ala Lys Ser Ala
        355                 360

<210> SEQ ID NO 87
<211> LENGTH: 485
<212> TYPE: PRT
<213> ORGANISM: Mus musculus

<400> SEQUENCE: 87

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Ser Gly Gly Ser Gly Gly Ser Gly Gly Ser Gly Leu Pro Val
        35                  40                  45

Asn Thr Arg Cys Lys Leu Glu Val Ser Asn Phe Gln Gln Pro Tyr Ile
    50                  55                  60

Val Asn Arg Thr Phe Met Leu Ala Lys Glu Ala Ser Leu Ala Asp Asn
65                  70                  75                  80

Asn Thr Asp Val Arg Leu Ile Gly Glu Lys Leu Phe Arg Gly Val Ser
                85                  90                  95

Ala Lys Asp Gln Cys Tyr Leu Met Lys Gln Val Leu Asn Phe Thr Leu
            100                 105                 110

Glu Asp Val Leu Leu Pro Gln Ser Asp Arg Phe Gln Pro Tyr Met Gln
        115                 120                 125

Glu Val Val Pro Phe Leu Thr Lys Leu Ser Asn Gln Leu Ser Ser Cys
    130                 135                 140

His Ile Ser Gly Asp Asp Gln Asn Ile Gln Lys Asn Val Arg Arg Leu
145                 150                 155                 160

Lys Glu Thr Val Lys Lys Leu Gly Glu Ser Gly Glu Ile Lys Ala Ile
                165                 170                 175

Gly Glu Leu Asp Leu Leu Phe Met Ser Leu Arg Asn Ala Cys Val Ser
            180                 185                 190

Gly Gly Gly Gly Ser Gly Gly Gly Ser Gly Gly Gly Gly Ser Glu
        195                 200                 205

Val Gln Leu Val Glu Ser Gly Gly Leu Val Gln Pro Gly Gly Ser
    210                 215                 220

Leu Arg Leu Ser Cys Ala Ala Ser Gly Ser Thr Trp Ser Ile Asn Thr
225                 230                 235                 240

Leu Ala Trp Tyr Arg Gln Ala Pro Gly Lys Gln Arg Asp Leu Val Ala
                245                 250                 255
```

```
Arg Ile Ser Ser Gly Gly Ser Thr Tyr Tyr Ala Asp Ser Val Lys Gly
            260                 265                 270

Arg Phe Thr Ile Ser Arg Asp Asn Ser Lys Asn Thr Leu Tyr Leu Gln
            275                 280                 285

Met Asn Ser Leu Arg Ala Glu Asp Thr Ala Val Tyr Tyr Cys Tyr Ala
290                 295                 300

Gln Ser Thr Trp Tyr Pro Ser Trp Gly Gln Gly Thr Leu Val Thr
305                 310                 315                 320

Val Ser Ser Gly Gly Gly Ser Gly Gly Gly Ser Gly Gly Gly Ser Gly
                325                 330                 335

Gly Gly Ser Leu Pro Val Asn Thr Arg Cys Lys Leu Glu Val Ser Asn
            340                 345                 350

Phe Gln Gln Pro Tyr Ile Val Asn Arg Thr Phe Met Leu Ala Lys Glu
            355                 360                 365

Ala Ser Leu Ala Asp Asn Asn Thr Asp Val Arg Leu Ile Gly Glu Lys
            370                 375                 380

Leu Phe Arg Gly Val Ser Ala Lys Asp Gln Cys Tyr Leu Met Lys Gln
385                 390                 395                 400

Val Leu Asn Phe Thr Leu Glu Asp Val Leu Leu Pro Gln Ser Asp Arg
                405                 410                 415

Phe Gln Pro Tyr Met Gln Glu Val Val Pro Phe Leu Thr Lys Leu Ser
            420                 425                 430

Asn Gln Leu Ser Ser Cys His Ile Ser Gly Asp Asp Gln Asn Ile Gln
            435                 440                 445

Lys Asn Val Arg Arg Leu Lys Glu Thr Val Lys Lys Leu Gly Glu Ser
            450                 455                 460

Gly Glu Ile Lys Ala Ile Gly Glu Leu Asp Leu Leu Phe Met Ser Leu
465                 470                 475                 480

Arg Asn Ala Cys Val
                485

<210> SEQ ID NO 88
<211> LENGTH: 485
<212> TYPE: PRT
<213> ORGANISM: Homo sapiens

<400> SEQUENCE: 88

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Ser Gly Gly Ser Gly Gly Ser Gly Gly Ser Gly Ala Pro Ile
            35                  40                  45

Ser Ser His Cys Arg Leu Asp Lys Ser Asn Phe Gln Gln Pro Tyr Ile
        50                  55                  60

Thr Asn Arg Thr Phe Met Leu Ala Lys Glu Ala Ser Leu Ala Asp Asn
65              70                  75                  80

Asn Thr Asp Val Arg Leu Ile Gly Glu Lys Leu Phe His Gly Val Ser
                85                  90                  95

Met Ser Glu Arg Cys Tyr Leu Met Lys Gln Val Leu Asn Phe Thr Leu
            100                 105                 110

Glu Glu Val Leu Phe Pro Gln Ser Asp Arg Phe Gln Pro Tyr Met Gln
        115                 120                 125
```

Glu Val Val Pro Phe Leu Ala Arg Leu Ser Asn Arg Leu Ser Thr Cys
130                 135                 140

His Ile Glu Gly Asp Asp Leu His Ile Gln Arg Asn Val Gln Lys Leu
145                 150                 155                 160

Lys Asp Thr Val Lys Lys Leu Gly Ser Gly Glu Ile Lys Ala Ile
            165                 170                 175

Gly Glu Leu Asp Leu Leu Phe Met Ser Leu Arg Asn Ala Cys Ile Ser
                180                 185                 190

Gly Gly Gly Gly Ser Gly Gly Gly Ser Gly Gly Gly Gly Ser Glu
            195                 200                 205

Val Gln Leu Val Glu Ser Gly Gly Gly Leu Val Gln Pro Gly Gly Ser
            210                 215                 220

Leu Arg Leu Ser Cys Ala Ala Ser Gly Ser Thr Trp Ser Ile Asn Thr
225                 230                 235                 240

Leu Ala Trp Tyr Arg Gln Ala Pro Gly Lys Gln Arg Asp Leu Val Ala
                245                 250                 255

Arg Ile Ser Ser Gly Gly Ser Thr Tyr Tyr Ala Asp Ser Val Lys Gly
                260                 265                 270

Arg Phe Thr Ile Ser Arg Asp Asn Ser Lys Asn Thr Leu Tyr Leu Gln
                275                 280                 285

Met Asn Ser Leu Arg Ala Glu Asp Thr Ala Val Tyr Tyr Cys Tyr Ala
            290                 295                 300

Gln Ser Thr Trp Tyr Pro Pro Ser Trp Gly Gln Gly Thr Leu Val Thr
305                 310                 315                 320

Val Ser Ser Gly Gly Gly Ser Gly Gly Gly Ser Gly Gly Gly Ser Gly
                325                 330                 335

Gly Gly Ser Ala Pro Ile Ser Ser His Cys Arg Leu Asp Lys Ser Asn
            340                 345                 350

Phe Gln Gln Pro Tyr Ile Thr Asn Arg Thr Phe Met Leu Ala Lys Glu
                355                 360                 365

Ala Ser Leu Ala Asp Asn Asn Thr Asp Val Arg Leu Ile Gly Glu Lys
            370                 375                 380

Leu Phe His Gly Val Ser Met Ser Glu Arg Cys Tyr Leu Met Lys Gln
385                 390                 395                 400

Val Leu Asn Phe Thr Leu Glu Glu Val Leu Phe Pro Gln Ser Asp Arg
                405                 410                 415

Phe Gln Pro Tyr Met Gln Glu Val Val Pro Phe Leu Ala Arg Leu Ser
                420                 425                 430

Asn Arg Leu Ser Thr Cys His Ile Glu Gly Asp Asp Leu His Ile Gln
            435                 440                 445

Arg Asn Val Gln Lys Leu Lys Asp Thr Val Lys Lys Leu Gly Glu Ser
            450                 455                 460

Gly Glu Ile Lys Ala Ile Gly Glu Leu Asp Leu Leu Phe Met Ser Leu
465                 470                 475                 480

Arg Asn Ala Cys Ile
            485

<210> SEQ ID NO 89
<211> LENGTH: 485
<212> TYPE: PRT
<213> ORGANISM: Mus musculus

<400> SEQUENCE: 89

```
Leu Pro Val Asn Thr Arg Cys Lys Leu Glu Val Ser Asn Phe Gln Gln
1               5                   10                  15

Pro Tyr Ile Val Asn Arg Thr Phe Met Leu Ala Lys Glu Ala Ser Leu
            20                  25                  30

Ala Asp Asn Asn Thr Asp Val Arg Leu Ile Gly Glu Lys Leu Phe Arg
        35                  40                  45

Gly Val Ser Ala Lys Asp Gln Cys Tyr Leu Met Lys Gln Val Leu Asn
    50                  55                  60

Phe Thr Leu Glu Asp Val Leu Leu Pro Gln Ser Asp Arg Phe Gln Pro
65                  70                  75                  80

Tyr Met Gln Glu Val Val Pro Phe Leu Thr Lys Leu Ser Asn Gln Leu
                85                  90                  95

Ser Ser Cys His Ile Ser Gly Asp Asp Gln Asn Ile Gln Lys Asn Val
            100                 105                 110

Arg Arg Leu Lys Glu Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Val Ser Gly Gly Gly Gly Ser Gly Gly Gly Ser Gly Gly Gly
145                 150                 155                 160

Gly Ser Gln Val Gln Leu Val Glu Ser Gly Gly Val Val Gln Pro
                165                 170                 175

Gly Gly Ser Leu Arg Leu Ser Cys Ala Ala Ser Gly Phe Ala Phe Arg
            180                 185                 190

Gly Phe Gly Met Ser Trp Val Arg Gln Ala Pro Gly Lys Gly Leu Glu
        195                 200                 205

Trp Val Ser Ser Ile Asn Asn Gly Gly Ser Asp Thr Tyr Tyr Ala Asp
    210                 215                 220

Ser Val Lys Gly Arg Phe Thr Ile Ser Arg Asp Asn Ser Lys Asn Thr
225                 230                 235                 240

Leu Tyr Leu Gln Met Asn Ser Leu Arg Ala Glu Asp Thr Ala Val Tyr
                245                 250                 255

Tyr Cys Ala Ile Gly Gly Pro Gly Ala Ser Pro Ser Gly Gln Gly Thr
            260                 265                 270

Gln Val Thr Val Ser Ser Gly Gly Gly Ser Gly Gly Gly Ser Gly Gly
        275                 280                 285

Gly Ser Gly Gly Gly Ser Leu Pro Val Asn Thr Arg Cys Lys Leu Glu
    290                 295                 300

Val Ser Asn Phe Gln Gln Pro Tyr Ile Val Asn Arg Thr Phe Met Leu
305                 310                 315                 320

Ala Lys Glu Ala Ser Leu Ala Asp Asn Asn Thr Asp Val Arg Leu Ile
                325                 330                 335

Gly Glu Lys Leu Phe Arg Gly Val Ser Ala Lys Asp Gln Cys Tyr Leu
            340                 345                 350

Met Lys Gln Val Leu Asn Phe Thr Leu Glu Asp Val Leu Leu Pro Gln
        355                 360                 365

Ser Asp Arg Phe Gln Pro Tyr Met Gln Glu Val Val Pro Phe Leu Thr
    370                 375                 380

Lys Leu Ser Asn Gln Leu Ser Ser Cys His Ile Ser Gly Asp Asp Gln
385                 390                 395                 400
```

```
Asn Ile Gln Lys Asn Val Arg Arg Leu Lys Glu Thr Val Lys Lys Leu
                405                 410                 415

Gly Glu Ser Gly Glu Ile Lys Ala Ile Gly Glu Leu Asp Leu Leu Phe
            420                 425                 430

Met Ser Leu Arg Asn Ala Cys Val Gly Ser Gly Ser Gly Gly Ser
        435                 440                 445

Gly Gly Ser Gly His Gly Asp Gly Ser Phe Ser Asp Glu Met Asn Thr
        450                 455                 460

Ile Leu Asp Asn Leu Ala Ala Arg Asp Phe Ile Asn Trp Leu Ile Gln
465                 470                 475                 480

Thr Lys Ile Thr Asp
            485

<210> SEQ ID NO 90
<211> LENGTH: 485
<212> TYPE: PRT
<213> ORGANISM: Homo sapiens

<400> SEQUENCE: 90

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Ile Ser Gly Gly Gly Ser Gly Gly Gly Ser Gly Gly Gly
145                 150                 155                 160

Gly Ser Gln Val Gln Leu Val Glu Ser Gly Gly Val Val Gln Pro
            165                 170                 175

Gly Gly Ser Leu Arg Leu Ser Cys Ala Ala Ser Gly Phe Ala Phe Arg
        180                 185                 190

Gly Phe Gly Met Ser Trp Val Arg Gln Ala Pro Gly Lys Gly Leu Glu
    195                 200                 205

Trp Val Ser Ser Ile Asn Asn Gly Gly Ser Asp Thr Tyr Tyr Ala Asp
        210                 215                 220

Ser Val Lys Gly Arg Phe Thr Ile Ser Arg Asp Asn Ser Lys Asn Thr
225                 230                 235                 240

Leu Tyr Leu Gln Met Asn Ser Leu Arg Ala Glu Asp Thr Ala Val Tyr
                245                 250                 255

Tyr Cys Ala Ile Gly Gly Pro Gly Ala Ser Pro Ser Gly Gln Gly Thr
            260                 265                 270
```

```
Gln Val Thr Val Ser Ser Gly Gly Ser Gly Gly Ser Gly Gly
            275                 280             285

Gly Ser Gly Gly Gly Ser Ala Pro Ile Ser Ser His Cys Arg Leu Asp
290                 295                 300

Lys Ser Asn Phe Gln Gln Pro Tyr Ile Thr Asn Arg Thr Phe Met Leu
305                 310                 315                 320

Ala Lys Glu Ala Ser Leu Ala Asp Asn Asn Thr Asp Val Arg Leu Ile
                325                 330                 335

Gly Glu Lys Leu Phe His Gly Val Ser Met Ser Glu Arg Cys Tyr Leu
                340                 345                 350

Met Lys Gln Val Leu Asn Phe Thr Leu Glu Glu Val Leu Phe Pro Gln
                355                 360                 365

Ser Asp Arg Phe Gln Pro Tyr Met Gln Glu Val Val Pro Phe Leu Ala
370                 375                 380

Arg Leu Ser Asn Arg Leu Ser Thr Cys His Ile Glu Gly Asp Asp Leu
385                 390                 395                 400

His Ile Gln Arg Asn Val Gln Lys Leu Lys Asp Thr Val Lys Lys Leu
                405                 410                 415

Gly Glu Ser Gly Glu Ile Lys Ala Ile Gly Glu Leu Asp Leu Leu Phe
                420                 425                 430

Met Ser Leu Arg Asn Ala Cys Ile Gly Ser Gly Gly Ser Gly Gly Ser
                435                 440                 445

Gly Gly Ser Gly His Gly Asp Gly Ser Phe Ser Asp Glu Met Asn Thr
                450                 455                 460

Ile Leu Asp Asn Leu Ala Ala Arg Asp Phe Ile Asn Trp Leu Ile Gln
465                 470                 475                 480

Thr Lys Ile Thr Asp
                485

<210> SEQ ID NO 91
<211> LENGTH: 522
<212> TYPE: PRT
<213> ORGANISM: Mus musculus

<400> SEQUENCE: 91

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
                35                  40                  45

Phe Arg Ser Cys Asp Leu Arg Arg Leu Glu Met Tyr Cys Ala Pro Leu
50                  55                  60

Lys Pro Ala Lys Ser Ala Gly Ser Gly Ser Gly Ser Gly Gly Ser Gly Gly
65                  70                  75                  80

Ser Gly Leu Pro Val Asn Thr Arg Cys Lys Leu Glu Val Ser Asn Phe
                85                  90                  95

Gln Gln Pro Tyr Ile Val Asn Arg Thr Phe Met Leu Ala Lys Glu Ala
                100                 105                 110

Ser Leu Ala Asp Asn Asn Thr Asp Val Arg Leu Ile Gly Glu Lys Leu
                115                 120                 125

Phe Arg Gly Val Ser Ala Lys Asp Gln Cys Tyr Leu Met Lys Gln Val
                130                 135                 140
```

```
Leu Asn Phe Thr Leu Glu Asp Val Leu Pro Gln Ser Asp Arg Phe
145                 150                 155                 160

Gln Pro Tyr Met Gln Glu Val Val Pro Phe Leu Thr Lys Leu Ser Asn
            165                 170                 175

Gln Leu Ser Ser Cys His Ile Ser Gly Asp Asp Gln Asn Ile Gln Lys
            180                 185                 190

Asn Val Arg Arg Leu Lys Glu Thr Val Lys Lys Leu Gly Glu Ser Gly
                195                 200                 205

Glu Ile Lys Ala Ile Gly Glu Leu Asp Leu Leu Phe Met Ser Leu Arg
210                 215                 220

Asn Ala Cys Val Ser Gly Gly Gly Ser Gly Gly Gly Ser Gly
225                 230                 235                 240

Gly Gly Gly Ser Glu Val Gln Leu Val Glu Ser Gly Gly Leu Val
            245                 250                 255

Gln Pro Gly Gly Ser Leu Arg Leu Ser Cys Ala Ala Ser Gly Ser Thr
            260                 265                 270

Trp Ser Ile Asn Thr Leu Ala Trp Tyr Arg Gln Ala Pro Gly Lys Gln
            275                 280                 285

Arg Asp Leu Val Ala Arg Ile Ser Ser Gly Gly Ser Thr Tyr Tyr Ala
290                 295                 300

Asp Ser Val Lys Gly Arg Phe Thr Ile Ser Arg Asp Asn Ser Lys Asn
305                 310                 315                 320

Thr Leu Tyr Leu Gln Met Asn Ser Leu Arg Ala Glu Asp Thr Ala Val
                325                 330                 335

Tyr Tyr Cys Tyr Ala Gln Ser Thr Trp Tyr Pro Pro Ser Trp Gly Gln
            340                 345                 350

Gly Thr Leu Val Thr Val Ser Ser Gly Gly Gly Ser Gly Gly Gly Ser
            355                 360                 365

Gly Gly Gly Ser Gly Gly Gly Ser Leu Pro Val Asn Thr Arg Cys Lys
            370                 375                 380

Leu Glu Val Ser Asn Phe Gln Gln Pro Tyr Ile Val Asn Arg Thr Phe
385                 390                 395                 400

Met Leu Ala Lys Glu Ala Ser Leu Ala Asp Asn Asn Thr Asp Val Arg
                405                 410                 415

Leu Ile Gly Glu Lys Leu Phe Arg Gly Val Ser Ala Lys Asp Gln Cys
                420                 425                 430

Tyr Leu Met Lys Gln Val Leu Asn Phe Thr Leu Glu Asp Val Leu Leu
            435                 440                 445

Pro Gln Ser Asp Arg Phe Gln Pro Tyr Met Gln Glu Val Val Pro Phe
450                 455                 460

Leu Thr Lys Leu Ser Asn Gln Leu Ser Ser Cys His Ile Ser Gly Asp
465                 470                 475                 480

Asp Gln Asn Ile Gln Lys Asn Val Arg Arg Leu Lys Glu Thr Val Lys
                485                 490                 495

Lys Leu Gly Glu Ser Gly Glu Ile Lys Ala Ile Gly Glu Leu Asp Leu
            500                 505                 510

Leu Phe Met Ser Leu Arg Asn Ala Cys Val
            515                 520
```

<210> SEQ ID NO 92
<211> LENGTH: 522
<212> TYPE: PRT
<213> ORGANISM: Homo sapiens

<400> SEQUENCE: 92

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala Gly Ser Gly Gly Ser Gly Gly Ser Gly Gly
65                  70                  75                  80

Ser Gly Ala Pro Ile Ser Ser His Cys Arg Leu Asp Lys Ser Asn Phe
                85                  90                  95

Gln Gln Pro Tyr Ile Thr Asn Arg Thr Phe Met Leu Ala Lys Glu Ala
            100                 105                 110

Ser Leu Ala Asp Asn Asn Thr Asp Val Arg Leu Ile Gly Glu Lys Leu
        115                 120                 125

Phe His Gly Val Ser Met Ser Glu Arg Cys Tyr Leu Met Lys Gln Val
    130                 135                 140

Leu Asn Phe Thr Leu Glu Glu Val Leu Phe Pro Gln Ser Asp Arg Phe
145                 150                 155                 160

Gln Pro Tyr Met Gln Glu Val Val Pro Phe Leu Ala Arg Leu Ser Asn
                165                 170                 175

Arg Leu Ser Thr Cys His Ile Glu Gly Asp Asp Leu His Ile Gln Arg
            180                 185                 190

Asn Val Gln Lys Leu Lys Asp Thr Val Lys Lys Leu Gly Glu Ser Gly
        195                 200                 205

Glu Ile Lys Ala Ile Gly Glu Leu Asp Leu Leu Phe Met Ser Leu Arg
    210                 215                 220

Asn Ala Cys Ile Ser Gly Gly Gly Ser Gly Gly Gly Gly Ser Gly
225                 230                 235                 240

Gly Gly Gly Ser Glu Val Gln Leu Val Glu Ser Gly Gly Gly Leu Val
                245                 250                 255

Gln Pro Gly Gly Ser Leu Arg Leu Ser Cys Ala Ala Ser Gly Ser Thr
            260                 265                 270

Trp Ser Ile Asn Thr Leu Ala Trp Tyr Arg Gln Ala Pro Gly Lys Gln
        275                 280                 285

Arg Asp Leu Val Ala Arg Ile Ser Ser Gly Gly Ser Thr Tyr Tyr Ala
    290                 295                 300

Asp Ser Val Lys Gly Arg Phe Thr Ile Ser Arg Asp Asn Ser Lys Asn
305                 310                 315                 320

Thr Leu Tyr Leu Gln Met Asn Ser Leu Arg Ala Glu Asp Thr Ala Val
                325                 330                 335

Tyr Tyr Cys Tyr Ala Gln Ser Thr Trp Tyr Pro Pro Ser Trp Gly Gln
            340                 345                 350

Gly Thr Leu Val Thr Val Ser Ser Gly Gly Gly Ser Gly Gly Gly Ser
        355                 360                 365

Gly Gly Gly Ser Gly Gly Gly Ser Ala Pro Ile Ser Ser His Cys Arg
    370                 375                 380

Leu Asp Lys Ser Asn Phe Gln Gln Pro Tyr Ile Thr Asn Arg Thr Phe
385                 390                 395                 400

Met Leu Ala Lys Glu Ala Ser Leu Ala Asp Asn Asn Thr Asp Val Arg
                405                 410                 415
```

```
Leu Ile Gly Glu Lys Leu Phe His Gly Val Ser Met Ser Glu Arg Cys
                420                 425                 430

Tyr Leu Met Lys Gln Val Leu Asn Phe Thr Leu Glu Glu Val Leu Phe
            435                 440                 445

Pro Gln Ser Asp Arg Phe Gln Pro Tyr Met Gln Glu Val Val Pro Phe
        450                 455                 460

Leu Ala Arg Leu Ser Asn Arg Leu Ser Thr Cys His Ile Glu Gly Asp
465                 470                 475                 480

Asp Leu His Ile Gln Arg Asn Val Gln Lys Leu Lys Asp Thr Val Lys
                485                 490                 495

Lys Leu Gly Glu Ser Gly Glu Ile Lys Ala Ile Gly Glu Leu Asp Leu
            500                 505                 510

Leu Phe Met Ser Leu Arg Asn Ala Cys Ile
        515                 520

<210> SEQ ID NO 93
<211> LENGTH: 522
<212> TYPE: PRT
<213> ORGANISM: Mus musculus

<400> SEQUENCE: 93

Leu Pro Val Asn Thr Arg Cys Lys Leu Glu Val Ser Asn Phe Gln Gln
1               5                   10                  15

Pro Tyr Ile Val Asn Arg Thr Phe Met Leu Ala Lys Glu Ala Ser Leu
            20                  25                  30

Ala Asp Asn Asn Thr Asp Val Arg Leu Ile Gly Glu Lys Leu Phe Arg
        35                  40                  45

Gly Val Ser Ala Lys Asp Gln Cys Tyr Leu Met Lys Gln Val Leu Asn
    50                  55                  60

Phe Thr Leu Glu Asp Val Leu Leu Pro Gln Ser Asp Arg Phe Gln Pro
65                  70                  75                  80

Tyr Met Gln Glu Val Val Pro Phe Leu Thr Lys Leu Ser Asn Gln Leu
                85                  90                  95

Ser Ser Cys His Ile Ser Gly Asp Asp Gln Asn Ile Gln Lys Asn Val
            100                 105                 110

Arg Arg Leu Lys Glu Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Val Ser Gly Gly Gly Gly Ser Gly Gly Gly Ser Gly Gly Gly Gly
145                 150                 155                 160

Gly Ser Gln Val Gln Leu Val Glu Ser Gly Gly Val Val Gln Pro
                165                 170                 175

Gly Gly Ser Leu Arg Leu Ser Cys Ala Ala Ser Gly Phe Ala Phe Arg
        180                 185                 190

Gly Phe Gly Met Ser Trp Val Arg Gln Ala Pro Gly Lys Gly Leu Glu
    195                 200                 205

Trp Val Ser Ser Ile Asn Asn Gly Gly Ser Asp Thr Tyr Tyr Ala Asp
210                 215                 220

Ser Val Lys Gly Arg Phe Thr Ile Ser Arg Asp Asn Ser Lys Asn Thr
225                 230                 235                 240

Leu Tyr Leu Gln Met Asn Ser Leu Arg Ala Glu Asp Thr Ala Val Tyr
                245                 250                 255
```

-continued

```
Tyr Cys Ala Ile Gly Gly Pro Gly Ala Ser Pro Ser Gly Gln Gly Thr
                260                 265                 270

Gln Val Thr Val Ser Ser Gly Gly Ser Gly Gly Ser Gly Gly
        275                 280                 285

Gly Ser Gly Gly Gly Ser Leu Pro Val Asn Thr Arg Cys Lys Leu Glu
    290                 295                 300

Val Ser Asn Phe Gln Gln Pro Tyr Ile Val Asn Arg Thr Phe Met Leu
305                 310                 315                 320

Ala Lys Glu Ala Ser Leu Ala Asp Asn Asn Thr Asp Val Arg Leu Ile
                325                 330                 335

Gly Glu Lys Leu Phe Arg Gly Val Ser Ala Lys Asp Gln Cys Tyr Leu
                340                 345                 350

Met Lys Gln Val Leu Asn Phe Thr Leu Glu Asp Val Leu Leu Pro Gln
                355                 360                 365

Ser Asp Arg Phe Gln Pro Tyr Met Gln Glu Val Val Pro Phe Leu Thr
    370                 375                 380

Lys Leu Ser Asn Gln Leu Ser Ser Cys His Ile Ser Gly Asp Asp Gln
385                 390                 395                 400

Asn Ile Gln Lys Asn Val Arg Arg Leu Lys Glu Thr Val Lys Lys Leu
                405                 410                 415

Gly Glu Ser Gly Glu Ile Lys Ala Ile Gly Glu Leu Asp Leu Leu Phe
                420                 425                 430

Met Ser Leu Arg Asn Ala Cys Val Gly Ser Gly Gly Ser Gly Gly Ser
                435                 440                 445

Gly Gly Ser Gly Gly Pro Glu Thr Leu Cys Gly Ala Glu Leu Val Asp
    450                 455                 460

Ala Leu Gln Phe Val Cys Gly Asp Arg Gly Phe Tyr Phe Asn Lys Pro
465                 470                 475                 480

Thr Gly Tyr Gly Ser Ser Arg Arg Ala Pro Gln Thr Gly Ile Val
                485                 490                 495

Asp Glu Cys Cys Phe Arg Ser Cys Asp Leu Arg Arg Leu Glu Met Tyr
                500                 505                 510

Cys Ala Pro Leu Lys Pro Ala Lys Ser Ala
                515                 520

<210> SEQ ID NO 94
<211> LENGTH: 522
<212> TYPE: PRT
<213> ORGANISM: Homo sapiens

<400> SEQUENCE: 94

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
                20                  25                  30

Ala Asp Asn Asn Thr Asp Val Arg Leu Ile Gly Glu Lys Leu Phe His
            35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95
```

```
Ser Thr Cys His Ile Glu Gly Asp Asp Leu His Ile Gln Arg Asn Val
            100                 105                 110

Gln Lys Leu Lys Asp Thr Val Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Ser Gly Gly Gly Ser Gly Gly Gly Ser Gly Gly Gly
145                 150                 155                 160

Gly Ser Gln Val Gln Leu Val Glu Ser Gly Gly Val Val Gln Pro
            165                 170                 175

Gly Gly Ser Leu Arg Leu Ser Cys Ala Ala Ser Gly Phe Ala Phe Arg
        180                 185                 190

Gly Phe Gly Met Ser Trp Val Arg Gln Ala Pro Gly Lys Gly Leu Glu
        195                 200                 205

Trp Val Ser Ser Ile Asn Asn Gly Gly Ser Asp Thr Tyr Tyr Ala Asp
    210                 215                 220

Ser Val Lys Gly Arg Phe Thr Ile Ser Arg Asp Asn Ser Lys Asn Thr
225                 230                 235                 240

Leu Tyr Leu Gln Met Asn Ser Leu Arg Ala Glu Asp Thr Ala Val Tyr
            245                 250                 255

Tyr Cys Ala Ile Gly Gly Pro Gly Ala Ser Pro Ser Gly Gln Gly Thr
        260                 265                 270

Gln Val Thr Val Ser Ser Gly Gly Gly Ser Gly Gly Gly Ser Gly Gly
        275                 280                 285

Gly Ser Gly Gly Gly Ser Ala Pro Ile Ser Ser His Cys Arg Leu Asp
        290                 295                 300

Lys Ser Asn Phe Gln Gln Pro Tyr Ile Thr Asn Arg Thr Phe Met Leu
305                 310                 315                 320

Ala Lys Glu Ala Ser Leu Ala Asp Asn Asn Thr Asp Val Arg Leu Ile
            325                 330                 335

Gly Glu Lys Leu Phe His Gly Val Ser Met Ser Glu Arg Cys Tyr Leu
        340                 345                 350

Met Lys Gln Val Leu Asn Phe Thr Leu Glu Glu Val Leu Phe Pro Gln
        355                 360                 365

Ser Asp Arg Phe Gln Pro Tyr Met Gln Glu Val Val Pro Phe Leu Ala
370                 375                 380

Arg Leu Ser Asn Arg Leu Ser Thr Cys His Ile Glu Gly Asp Asp Leu
385                 390                 395                 400

His Ile Gln Arg Asn Val Gln Lys Leu Lys Asp Thr Val Lys Lys Leu
            405                 410                 415

Gly Glu Ser Gly Glu Ile Lys Ala Ile Gly Glu Leu Asp Leu Leu Phe
        420                 425                 430

Met Ser Leu Arg Asn Ala Cys Ile Gly Ser Gly Gly Ser Gly Gly Ser
        435                 440                 445

Gly Gly Ser Gly Gly Pro Glu Thr Leu Cys Gly Ala Glu Leu Val Asp
        450                 455                 460

Ala Leu Gln Phe Val Cys Gly Asp Arg Gly Phe Tyr Phe Asn Lys Pro
465                 470                 475                 480

Thr Gly Tyr Gly Ser Ser Arg Arg Ala Pro Gln Thr Gly Ile Val
            485                 490                 495

Asp Glu Cys Cys Phe Arg Ser Cys Asp Leu Arg Arg Leu Glu Met Tyr
        500                 505                 510
```

```
Cys Ala Pro Leu Lys Pro Ala Lys Ser Ala
        515                 520

<210> SEQ ID NO 95
<211> LENGTH: 378
<212> TYPE: PRT
<213> ORGANISM: Mus musculus

<400> SEQUENCE: 95

Leu Pro Val Asn Thr Arg Cys Lys Leu Glu Val Ser Asn Phe Gln Gln
1               5                   10                  15

Pro Tyr Ile Val Asn Arg Thr Phe Met Leu Ala Lys Glu Ala Ser Leu
            20                  25                  30

Ala Asp Asn Asn Thr Asp Val Arg Leu Ile Gly Glu Lys Leu Phe Arg
        35                  40                  45

Gly Val Ser Ala Lys Asp Gln Cys Tyr Leu Met Lys Gln Val Leu Asn
50                  55                  60

Phe Thr Leu Glu Asp Val Leu Leu Pro Gln Ser Asp Arg Phe Gln Pro
65                  70                  75                  80

Tyr Met Gln Glu Val Val Pro Phe Leu Thr Lys Leu Ser Asn Gln Leu
                85                  90                  95

Ser Ser Cys His Ile Ser Gly Asp Asp Gln Asn Ile Gln Lys Asn Val
            100                 105                 110

Arg Arg Leu Lys Glu Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Val Ala Arg Gly Pro Thr Ile Lys Pro Cys Pro Pro Cys Lys Cys
145                 150                 155                 160

Pro Ala Pro Asn Leu Leu Gly Gly Pro Ser Val Phe Ile Phe Pro Pro
                165                 170                 175

Lys Ile Lys Asp Val Leu Met Ile Ser Leu Ser Pro Ile Val Thr Cys
            180                 185                 190

Val Val Val Asp Val Ser Glu Asp Asp Pro Asp Val Gln Ile Ser Trp
        195                 200                 205

Phe Val Asn Asn Val Glu Val His Thr Ala Gln Thr Gln Thr His Arg
210                 215                 220

Glu Asp Tyr Asn Ser Thr Leu Arg Val Val Ser Ala Leu Pro Ile Gln
225                 230                 235                 240

His Gln Asp Trp Met Ser Gly Lys Glu Phe Lys Cys Lys Val Asn Asn
                245                 250                 255

Lys Asp Leu Pro Ala Pro Ile Glu Arg Thr Ile Ser Lys Pro Lys Gly
            260                 265                 270

Ser Val Arg Ala Pro Gln Val Tyr Val Leu Pro Pro Pro Glu Glu Glu
        275                 280                 285

Met Thr Lys Lys Gln Val Thr Leu Thr Cys Met Val Thr Asp Phe Met
290                 295                 300

Pro Glu Asp Ile Tyr Val Glu Trp Thr Asn Asn Gly Lys Thr Glu Leu
305                 310                 315                 320

Asn Tyr Lys Asn Thr Glu Pro Val Leu Asp Ser Asp Gly Ser Tyr Phe
                325                 330                 335

Met Tyr Ser Lys Leu Arg Val Glu Lys Lys Asn Trp Val Glu Arg Asn
            340                 345                 350

Ser Tyr Ser Cys Ser Val Val His Glu Gly Leu His Asn His His Thr
        355                 360                 365
```

```
Thr Lys Ser Phe Ser Arg Thr Pro Gly Lys
370                 375
```